United States Patent
Badiang et al.

(10) Patent No.: US 7,279,473 B2
(45) Date of Patent: Oct. 9, 2007

(54) PYRAZOLOPYRIDAZINE DERIVATIVES

(75) Inventors: Jennifer G. Badiang, Durham, NC (US); Scott Howard Dickerson, Durham, NC (US); Philip Anthony Harris, Durham, NC (US); David Kendall Jung, Durham, NC (US); Michael Robert Peel, Durham, NC (US); Michael John Reno, Durham, NC (US); Tara Renae Rheault, Durham, NC (US); Kirk Lawrence Stevens, Durham, NC (US); Francis Xavier Tavares, Durham, NC (US); James Marvin Veal, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 332 days.

(21) Appl. No.: 10/499,179

(22) PCT Filed: Dec. 11, 2002

(86) PCT No.: PCT/US02/39672

§ 371 (c)(1),
(2), (4) Date: Nov. 19, 2004

(87) PCT Pub. No.: WO03/051886

PCT Pub. Date: Jun. 26, 2003

(65) Prior Publication Data

US 2005/0090507 A1    Apr. 28, 2005

Related U.S. Application Data

(60) Provisional application No. 60/341,798, filed on Dec. 17, 2001.

(51) Int. Cl.
*C07D 487/04* (2006.01)
*A61K 31/5025* (2006.01)

(52) U.S. Cl. .................. 514/233.2; 514/248; 544/105; 544/236

(58) Field of Classification Search ............... 544/105, 544/236; 514/233.2, 248
See application file for complete search history.

(56) References Cited

U.S. PATENT DOCUMENTS 5,498,774 A    3/1996 Mitsudera et al.

FOREIGN PATENT DOCUMENTS

| EP | 0 404 190 | 6/1990 |
|---|---|---|
| WO | 98/54093 | 12/1998 |
| WO | 99/12930 | 3/1999 |
| WO | 99/32447 | 7/1999 |
| WO | 01/14375 | 3/2001 |
| WO | 01/34605 | 5/2001 |
| WO | 02/22601 | 3/2002 |
| WO | 02/066481 | 8/2002 |

OTHER PUBLICATIONS

Blain et al., Differential Interaction of the Cyclin-dependent kinase (Cdk) Inhibitor p27kip1 with Cyclin A-Cdk2 and Cyclin D2-Cdk4, The Journal of Biological Chemistry, vol. 272, No. 41, pp. 25863-25872, 1997.*
LuValle et al., Cell Cycle Control in Growth Plate Chondrocytes, Frontiers in Bioscience 5, d493-503, May 2001.*
Simone, Oncology: Introduction, Cecil Textbook of Medicine, 20th Edition, vol. 1, pp. 1004-1010, 1996.*
Traxler, Protein Tyrosine Kinase Inhibitors in cancer treatment, Expert Opinion on Therapeutic Patents, 7(6):571-588, 1997.*
West, Solid Solutions, Solid state chemistry and it's applications, Wiley, New York, pp. 358 and 365, 1988.*
Vippagunta et al., Crystalline solids, Advanced Drug Delivery Reviews, 48 (2001), pp. 3-26, 2001.*
Ulrich, Crystallization, Kirk-Othmer Encyclopedia of Chemical Technology, vol. 8, pp. 113-120, (http://www.mrw.interscience.wiley.com/kirk/articles/crysrous.a01/sect4-fs.html) Aug. 2002.*
Teixeira et al., CDK2 is a Target for Retinoic Acid-Mediated Growth Inhibition in MCF-7 Human Breast Cancer Cells, Molecular Endocrinology, vol. 11, No. 9, pp. 1191-1202, 1997.*
Davis et al., "Prevent of Chemotherapy-Induced Alopecia in Rats by CDK Inhibitors," *Science*, 2001, V291, pp. 134-137.
Katritzki, A.R. et al., "Syntheses of 2-Alkylamino- and 2-Dialkylamino-4,6-diarylpyridines and 2,4,6-Trisubstituted Pyrimidines Using Solid-Phase-Bound Chalcones," *Journal of Combinatoral Chemistry*, 2000, V2, N2, pp. 182-185.
Henke, B.R. et al., "2-Amino-4,6-Diarylpyridines as Novel Ligands for the Estrogen Receptor," *Bioorganic & Medcinal Chemistry Letters*, 2001, V11, N14, pp. 1939-1942.
Katritzky, "Benzotriazole-assisted preparations of 2-(substituted amino)pyridines and pyrid-2-ones," *J. Org. Chem.*, 1997, V62, N18, pp. 6210-6214.
Chemical Abstracts, vol. 115, No. 3, 1991, Columbus, Ohio.
Belstein Institut zur Forderung der Chemischen Wissenschaften, Frankfurt am Main, DE; XP002203368, 1961.
Chemical Abstracts, vol. 100, No. 25, 1984, Columbus, Ohio.
Belstein Institut zur Forderung der Chemischen Wissenschaften, Frankfurt am Main, DE; XP002203369, 1971.
Belstein Institut zur Forderung der Chemischen Wissenschaften, Frankfurt am Main, DE; XP002203370, 1970.

* cited by examiner

*Primary Examiner*—Deepak Rao
(74) *Attorney, Agent, or Firm*—John L. Lemanowicz; Kathryn L. Coulter

(57) ABSTRACT

Fused pyradazine derivatives which are usefule as CDK inhibitors are described herein. The described invention alos includes methods of making such fused pyradazine derivatives as wells as methods of using the same in the treatment of hyperproliferative diseases.

36 Claims, No Drawings

PYRAZOLOPYRIDAZINE DERIVATIVES

This application is filed pursuant to 35 U.S.C. § 371 as a U.S. National Phase Application of International Application No. PCT/US02/39672 filed Dec. 11, 2002, which claims priority from U.S. 60/341,798 filed Dec. 17, 2001.

BACKGROUND OF THE INVENTION

The present invention relates to fused pyridazine derivatives, methods for the preparation of such fused pyridazines, and use of such fused pyridazines in the treatment of certain diseases or conditions. In particular, the present invention relates to fused pyridazine derivatives useful as cyclin dependent kinase inhibitors and use of the fused pyridazines in the treatment of disorders mediated by inappropriate cyclin dependent kinase activity.

Effective chemotherapy, as well as radiotherapy, for cancer treatment, which has acceptable toxicity to normal cells, is a continuing goal in the oncology field. Numerous cytotoxic agents are used in the treatment of cancer, including cytotoxic agents that adversely affect rapidly dividing cells, including normal cells, that are in the process of cell division. Typically, such agents may have effect on the cell cycle at $G_1$—the period between mitosis and DNA synthesis; S—the period of DNA synthesis; $G_2$—the pre-mitotic interval; and/or M—the period of mitosis and are termed phase specific agents. Such agents are not effective in $G_o$, the quiescent or resting cell phase. Therefore, such anti-neoplastic agents are active against cells in the process of cell division and are most effective against cancers that have a large growth fraction, that is, tumors that have a high percentage of dividing cells. Problematically, however, such agents also have an adverse effect on rapidly proliferating, normal tissues such as hair follicles and intestinal epithelium (See Goodman Et Gilman's, The Pharmacologic Basis Of Therapeutics 9$^{th}$ Ed., pages 1230-1232.) which may lead to chemotherapy-induced alopecia (CIA) or mucositis. CIA as well as mucositis are frequent emotionally and/or physically distressing side effects of cancer chemo- and radiotherapies.

Protein kinases catalyze the phosphorylation of various residues in proteins including proteins involved in the regulation of cell growth and differentiation. Protein kinases play a critical role in the control of cell growth and differentiation and are key mediators of cellular signals leading to the production of growth factors and cytokines. See, for example, Schlessinger and Ullrich, *Neuron* 1992, 9, 383. The signals mediated by protein kinases have also been shown to control growth, death and differentiation in the cell by regulating the processes of the cell cycle.

Progression through the eukaryotic cell cycle is controlled by a family of protein kinases called cyclin dependent kinases (CDKs) and their interaction with a family of proteins termed cyclins (Myerson, et al., EMBO Journal 1992, 11, 2909-17). The coordinate activation and inactivation of different cyclin/CDK complexes is necessary for normal progression through the cell cycle (Pines, Trends in Biochemical Sciences 1993, 18, 195-7; Sherr, Cell 1993, 73, 1059-1065.). Both the critical G1-S and G2-M transitions are controlled by the activation of different cyclin/CDK activities. In G1, both cyclin D/CDK4 and cyclin E/CDK2 are thought to mediate the onset of S-phase. Progression through S-phase requires the activity of cyclin A/CDK2 whereas the activation of cyclin A/cdc2 (CDK1) and cyclin B/cdc2 are required for the onset of metaphase. It is not surprising, therefore, that the loss of control of CDK regulation is a frequent event in hyperproliferative diseases and cancer. (Pines, Current Opinion in Cell Biology 1992, 4, 144-8; Lees, Current Opinion in Cell Biology 1995, 7, 773-80; Hunter and Pines, Cell 1994, 79, 573-82).

Consequently, inhibition of CDKs may prevent progression in the cell cycle in normal cells and limit the toxicity of cytotoxics which act in S-phase, G2 or mitosis. Such disruption of the cell cycle of normal proliferating cells should therefore protect proliferating cells such as hair follicles and epithelial mucosa from the effects of cytotoxic agents and thereby provide a potent treatment for side effects associated with cancer chemo- and radiotherapies.

The present inventors have discovered novel fused pyridazine derivatives, which are inhibitors of CDK, specifically CDK2 and CDK4 activity. Such pyridazine derivatives are useful in the treatment of CIA and mucositis as well as cancer.

BRIEF SUMMARY OF THE INVENTION

In one aspect of the present invention, there is provided a compound of Formula (I):

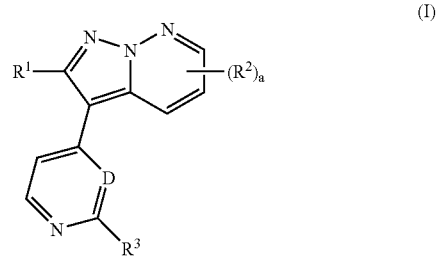

or a salt, solvate, or physiologically functional derivative thereof:

wherein:

D is N or CH $R^1$ is hydrogen, $C_1$-$C_6$ alkyl, $C_2$-$C_4$ alkenyl, $C_2$-$C_4$ alkynyl, $C_1$-$C_3$ alkoxy, halogen, —$CF_3$, hydroxy, cyano, —S(O)$_y$-$C_1$-$C_3$ alkyl, or —$NR^4R^5$;

y is 0, 1, or 2;

a is 1 or 2;

$R^2$ is hydrogen, $C_1$-$C_6$ alkyl, $C_2$-$C_6$ alkenyl, $C_2$-$C_6$ alkynyl, $C_1$-$C_6$ haloalkyl, $C_3$-$C_7$ cycloalkyl, halogen, heterocyclyl, aryl, heteroaryl, cyano, azido, nitro, —$OR^8$, —$OR^6R^8$, —$R^6R^7$, —$R^6R''$, —$OS(O)_2R^9$, —$S(O)_yR^{10}$, —$C(O)R^7$, —$C(O)OR^7$, —$C(O)NR^4R^5$, —$N(H)R'C(=NR^4)NR^4R^5$, —$OC(O)NR^4R^5$, —$OC(O)OR^7$, —$C(=NR^4)NR^4R^5$, —$NR^4R^5$, —$OC(O)R^7$, or —$N(R^8)C(O)R^8$;

$R^3$ is -(Q)$_p$-(Q$^1$)

where

Q$^1$ is O, N(R$^8$) or S(O)$_y$, p is 0 or 1, y is 0, 1, or 2 and

Q$^1$ is $C_1$-$C_6$ alkyl, $C_3$-$C_7$ cycloalkyl, $C_1$-$C_6$ haloalkyl, aryl, aryl substituted with —C(O)N(H)R$^6$NR$^4$R$^5$ or —OC(H)(OH)R$^6$NR$^4$R$^5$, heteroaryl, aralkyl, or —R$^6$NR$^4$R$^5$;

$R^4$ and $R^5$ are independently hydrogen, $C_1$-$C_3$ alkyl, $C_3$-$C_7$ cycloalkyl, —C(O)R$^9$, or $R^4$ and $R^5$, together with the nitrogen atom to which they are bound, form a heterocyclyl;

$R^6$ is alkylene, arylene, heteroarylene, $C_{3-7}$ cycloalkylene, alkenylene, $C_3$-$C_7$ cycloalkenylene, or alkynylene;

$R^7$ is hydrogen, $C_1$-$C_6$ alkyl, $C_2$-$C_6$ alkenyl, $C_2$-$C_6$ alkynyl, —NR$^4$R$^5$, aryl, aralkyl, heteroaryl, cycloalkyl, heterocyclyl, —S(O)$_y$R$^{10}$, —C(O)R$^8$, —C(O)OR$^8$, —C(O)

NR⁴R⁵, —S(O)₂NR⁴R⁵, —N(H)R'C(=NR⁴)NR⁴R⁵, —OC(O)NR⁴R⁵, —OC(O)OR⁸, —C(=NR⁴)NR⁴R⁵, —NR⁴R⁵, or —N(R⁸)C(O)R⁸;

R⁸ is hydrogen, C₁-C₆ alkyl, C₂-C₆ alkenyl, C₂-C₆ alkynyl, —NR⁴R⁵, aryl, aralkyl, heteroaryl, cycloalkyl, heterocyclyl, or —S(O)₂R⁹;

R⁹ is C₁-C₆ alkyl or C₁-C₆ haloalkyl;

R¹⁰ is hydrogen, C₁-C₆ alkyl, C₂-C₆ alkenyl, C₂-C₆ alkynyl, —NR⁴R⁵, aryl, aralkyl, heteroaryl, cycloalkyl, heterocyclyl, —C(O)R⁸, —C(O)OR⁸, —C(O)NR⁴R⁵, —N(H)R'C(=NR⁴)NR⁴R⁵, —OC(O)NR⁴R⁵, —OC(O)OR⁸, —C(=NR⁴)NR⁴R⁵, —NR⁴R⁵, or —N(R⁸)C(O)R⁸;

R' is C₁-C₃ alkylene; and

R" is —OR⁷, —OC(O)NR⁴R⁵, —OC(O)OR⁷, or —OC(O)R⁷.

In a second aspect of the present invention, there is provided a compound of Formula (II):

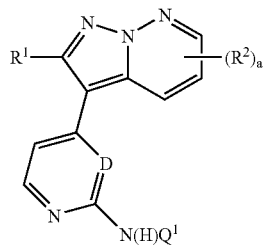

(II)

or a salt, solvate, or physiologically functional derivative thereof:
wherein:
D is N or CH;
R¹ is hydrogen, C₁-C₆ alkyl, C₂-C₄ alkenyl, C₂-C₄ alkynyl, C₁-C₃ alkoxy, —CF₃, halogen, hydroxy, cyano, —S(O)ᵧ C₁-C₃ alkyl, or —NR⁴R⁵;
y is 0, 1, or 2;
a is 1 or 2;
R² is hydrogen, C₁-C₆ alkyl, C₂-C₆ alkenyl, C₂-C₆ alkynyl, C₁-C₆ haloalkyl, C₃-C₇ cycloalkyl, halogen, heterocyclyl, aryl, heteroaryl, cyano, azido, nitro, —OR⁸, —OR⁶R⁸, —R⁶R⁷, —R⁶R", —OS(O)₂R⁹, —S(O)ᵧR¹⁰, —C(O)R⁷, —C(O)OR⁷, —C(O)NR⁴R⁵, —N(H)R'C(=NR⁴)NR⁴R⁵, —OC(O)NR⁴R⁵, —OC(O)OR⁷, —C(=NR⁴)NR⁴R⁵, —NR⁴R⁵, —OC(O)R⁷; or —N(R⁷)C(O)R⁷;
Q¹ is C₁-C₆ alkyl, C₃-C₇ cycloalkyl, C₁-C₆ haloalkyl, aryl, aryl substituted with —C(O)N(H)R⁶NR⁴R⁵ or —OC(H)(OH)R⁶NR⁴R⁵, heteroaryl, aralkyl, or —R⁶NR⁴R⁵;
R⁴ and R⁵ are independently hydrogen, C₁-C₃ alkyl, C₃-C₇ cycloalkyl, —C(O)R⁹, or R⁴ and R⁵, together with the nitrogen atom to which they are bound, form a heterocyclyl;
R⁶ is alkylene, arylene, heteroarylene, C₃-C₇ cycloalkylene, alkenylene, C₃-C₇ cycloalkenylene, or alkynylene;
R⁷ is hydrogen, C₁-C₆ alkyl, C₂-C₆ alkenyl, C₂-C₆ alkynyl, —NR⁴R⁵, aryl, aralkyl, heteroaryl, cycloalkyl, heterocyclyl, —S(O)ᵧR¹⁰, —C(O)R⁸, —C(O)OR⁸, —C(O)NR⁴R⁵, —S(O)₂NR⁴R⁵, —N(H)R'C(=NR⁴)NR⁴R⁵, —OC(O)NR⁴R⁵, —OC(O)OR⁸, —C(=NR⁴)NR⁴R⁵, —NR⁴R⁵, or —N(R⁷)C(O)R⁷;
R⁸ is hydrogen, C₁-C₆ alkyl, C₂-C₆ alkenyl, C₂-C₆ alkynyl, —NR⁴R⁵, aryl, aralkyl, heteroaryl, cycloalkyl, heterocyclyl, or —S(O)₂R⁹;
R⁹ is C₁-C₆ alkyl or C₁-C₆ haloalkyl;

R¹⁰ is hydrogen, C₁-C₆ alkyl, C₂-C₆ alkenyl, C₂-C₆ alkynyl, —NR⁴R⁵, aryl, aralkyl, heteroaryl, cycloalkyl, heterocyclyl, —C(O)R⁸, —C(O)OR⁸, —C(O)NR⁴R⁵, —N(H)R'C(=NR⁴)NR⁴R⁵, —OC(O)NR⁴R⁵, —OC(O)OR⁸, —C(=NR⁴)NR⁴R⁵, —NR⁴R⁵, or —N(R⁸)C(O)R⁸;

R' is C₁-C₃ alkylene; and

R" is —OR⁷, —OC(O)NR⁴R⁵, —OC(O)OR⁷, or —OC(O)R⁷.

In a third aspect of the present invention, there is provided a compound of Formula (III):

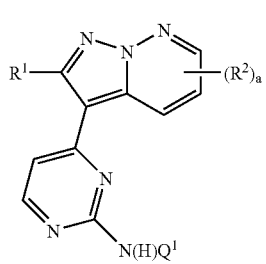

(III)

or a salt, solvate, or physiologically functional derivative thereof:
wherein:
R¹ is hydrogen, C₁-C₆ alkyl, C₂-C₄ alkenyl, C₂-C₄ alkynyl, C₁-C₃ alkoxy, —CF₃, halogen, hydroxy, cyano, —S(O)ᵧ C₁-C₃ alkyl, or —NR⁴R⁵;
y is 0, 1, or 2;
a is 1 or 2;
R² is hydrogen, C₁-C₆ alkyl, C₂-C₆ alkenyl, C₂-C₆ alkynyl, C₁-C₁ haloalkyl, —CF₃, C₃-C₇ cycloalkyl, halogen, heterocyclyl, aryl, heteroaryl, cyano, azido, nitro, —OR⁸, —OR⁶R⁸, —R⁶R⁷, —R⁶R", —OS(O)₂R⁹, —S(O)ᵧNR¹⁰, —C(O)R⁷, —C(O)OR⁷, —C(O)NR⁴R⁵, —N(H)R'C(=NR⁴)NR⁴R⁵, —OC(O)NR⁴R⁵, —OC(O)OR⁷, —C(=NR⁴)NR⁴R⁵, —NR⁴R⁵, —OC(O)R⁷, or —N(R⁷)C(O)R⁷;
Q¹ is C₁-C₆ alkyl, C₃-C₇ cycloalkyl, C₁-C₆ haloalkyl, aryl, aryl substituted with —C(O)N(H)R⁶NR⁴R⁵ or —OC(H)(OH)R⁶NR⁴R⁵, heteroaryl, aralkyl, or —R⁶NR⁴R⁵;
R⁴ and R⁵ are independently hydrogen, C₁-C₃ alkyl, C₃-C₇ cycloalkyl, —C(O)R⁹, or R⁴ and R⁵, together with the nitrogen atom to which they are bound, form a heterocyclyl;
R⁶ is alkylene, arylene, heteroarylene, C₃-C₇ cycloalkylene, alkenylene, C₃-C₇ cycloalkenylene, or alkynylene;
R⁷ is hydrogen, C₁-C₆ alkyl, C₂-C₆ alkenyl, C₂-C₆ alkynyl, —NR⁴R⁵, aryl, aralkyl, heteroaryl, cycloalkyl, heterocyclyl, —S(O)ᵧR¹⁰, —C(O)R⁸, —C(O)OR⁸, —C(O)NR⁴R⁵, —S(O)₂NR⁴R⁵, —N(H)R'C(=NR⁴)NR⁴R⁵, —OC(O)NR⁴R⁵, OC(O)OR⁸, —C(=NR⁴)NR⁴R⁵, —NR⁴R⁵, or —N(R⁷)C(O)R⁷;
R⁸ is hydrogen, C₁-C₆ alkyl, C₂-C₆ alkenyl, C₂-C₆ alkynyl, —NR⁴R⁵, aryl, aralkyl, heteroaryl, cycloalkyl, heterocyclyl, or —S(O)₂R⁹;
R⁹ is C₁-C₆ alkyl or C₁-C₆ haloalkyl;
R¹⁰ is hydrogen, C₁-C₆ alkyl, C₂-C₆ alkenyl, C₂-C₆ alkynyl, —NR⁴R⁵, aryl, aralkyl, heteroaryl, cycloalkyl, heterocyclyl, —C(O)R⁸, —C(O)OR⁸, —C(O)NR⁴R⁵, —N(H)R'C(=NR⁴)NR⁴R⁵, —OC(O)NR⁴R⁵, —OC(O)OR⁸, —C(=NR⁴)NR⁴R⁵, —NR⁴R⁵, or —N(R⁸)C(O)R⁸;
R' is C₁-C₃ alkylene; and
R" is —OR⁷, —OC(O)NR⁴R⁵, —OC(O)OR⁷, or —OC(O)R⁷.

In a fourth aspect of the present invention, there is provided a compound of Formula (IV):

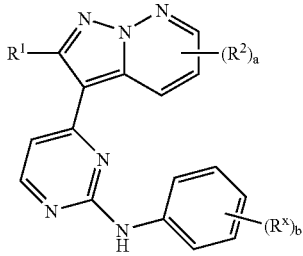

(IV)

or a salt, solvate, or physiologically functional derivative thereof:
wherein:
$R^1$ is hydrogen, $C_1$-$C_6$ alkyl, $C_2$-$C_4$ alkenyl, $C_2$-$C_4$ alkynyl, $C_1$-$C_3$ alkoxy, $C_1$-$C_6$ haloalkyl, halogen, hydroxy, cyano, —S(O)$_y$C$_1$-C$_3$ alkyl, or —NR$^4$R$^5$;
y is 0, 1, or 2;
a is 1 or 2;
$R^2$ is hydrogen, $C_1$-$C_6$ alkyl, $C_2$-$C_6$ alkenyl, $C_2$-$C_6$ alkynyl, $C_1$-$C_6$ haloalkyl, $C_3$-$C_7$ cycloalkyl, halogen, heterocyclyl, aryl, heteroaryl, cyano, azido, nitro, —OR$^8$, —OR$^6$R$^8$, —R$^6$R$^7$, —R$^6$R", —OS(O)$_2$R$^9$, —S(O)$_y$R$^{10}$, —C(O)R$^7$, —C(O)OR$^7$, —C(O)NR$^4$R$^5$, —N(H)R'C(=NR$^4$)NR$^4$R$^5$, —OC(O)NR$^4$R$^5$, —OC(O)OR$^7$, —C(=NR$^4$)NR$^4$R$^5$, —NR$^4$R$^5$, —OC(O)R$^7$, or —N(R$^7$)C(O)R$^7$;
b is 1, 2, or 3;
$R^x$ is independently selected from hydrogen, halogen, $C_1$-$C_6$ alkyl, $C_1$-$C_6$ hydroxyalkyl, —CN, —C(O)OH, —OC(O)R$^{11}$, $C_1$-$C_6$ haloalkyl, —NO$_2$, —OH, —OR$^9$, aryl, heteroaryl, heterocyclyl, —NR$^4$R$^5$, —R$^6$NR$^4$R$^5$, —C(O)N(H)R$^6$NR$^4$R$^5$, —S(O)$_y$R$^{10}$, —SO$_2$OH,
or
b is 2 and the two R$^x$ groups together with the phenyl group to which they are bound form a fused group selected from:

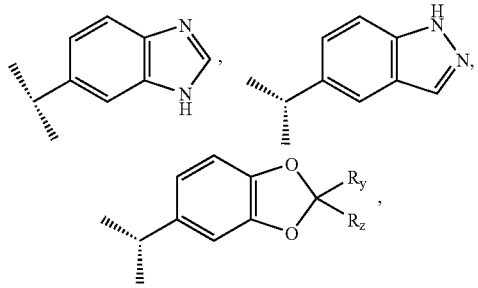

wherein R$_y$ and R$_z$ are independently selected from hydrogen and halogen,

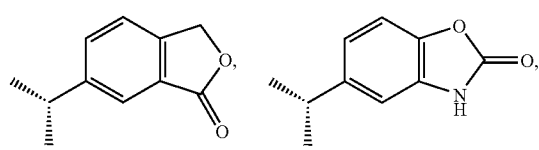

-continued

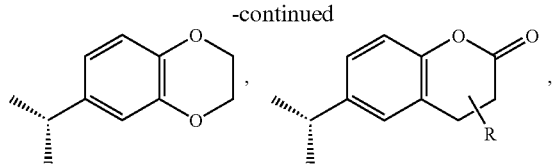

wherein R is selected from —CF3, halogen, or hydrogen;
$R^4$ and $R^5$ are independently hydrogen, $C_1$-$C_3$ alkyl, $C_3$-$C_7$ cycloalkyl, —C(O)R$^9$, or R$^4$ and R$^5$, together with the nitrogen atom to which they are bound, form a heterocyclyl;
$R^6$ is alkylene, arylene, heteroarylene, $C_3$-$C_7$ cycloalkylene, alkenylene, $C_3$-$C_7$ cycloalkenylene, or alkynylene;
$R^7$ is hydrogen, $C_1$-$C_6$ alkyl, $C_2$-$C_6$ alkenyl, $C_2$-$C_6$ alkynyl, —NR$^4$R$^5$, aryl, aralkyl, heteroaryl, cycloalkyl, heterocyclyl, —S(O)$_y$R$^{10}$, —C(O)R$^8$, —C(O)OR$^8$, —C(O)NR$^4$R$^5$, —S(O)$_2$NR$^4$R$^5$, —N(H)R'C(=NR$^4$)NR$^4$R$^5$, —OC(O)NR$^4$R$^5$, —OC(O)OR$^8$, —C(=NR$^4$)NR$^4$R$^5$, —NR$^4$R$^5$, or —N(R$^7$)C(O)R$^7$;
$R^8$ is hydrogen, $C_1$-$C_6$ alkyl, $C_2$-$C_6$ alkenyl, $C_2$-$C_6$ alkynyl, —NR$^4$R$^5$, aryl, aralkyl, heteroaryl, cycloalkyl, heterocyclyl, or —S(O)$_2$R$^9$;
$R^9$ is $C_1$-$C_6$ alkyl or $C_1$-$C_6$ haloalkyl;
$R^{10}$ is hydrogen, $C_1$-$C_6$ alkyl, $C_2$-$C_6$ alkenyl, $C_2$-$C_6$ alkynyl, —NR$^4$R$^5$, aryl, aralkyl, heteroaryl, cycloalkyl, heterocyclyl, —C(O)R$^8$, —C(O)OR$^8$, —C(O)NR$^4$R$^5$, —N(H)R'C(=NR$^4$)NR$^4$R$^5$, —OC(O)NR$^4$R$^5$, —OC(O)OR$^8$, —C(=NR$^4$)NR$^4$R, —NR$^4$R$^5$, or —N(R$^8$)C(O)R$^8$;
$R^{11}$ is $C_1$-$C_6$ alkyl;
R' is $C_1$-$C_3$ alkylene; and
R" is —OR$^7$, —OC(O)NR$^4$R$^5$, —OC(O)OR$^7$, or —OC(O)R$^7$.

In a fifth aspect of the present invention, there is provided a compound of Formula (IVa):

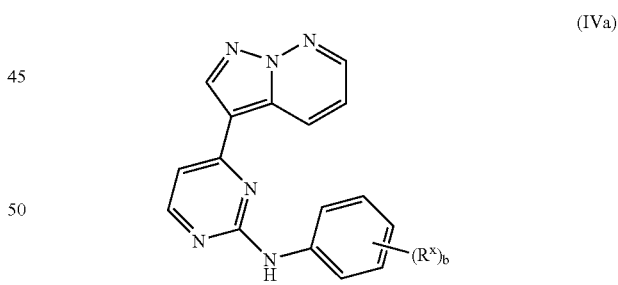

(IVa)

or a salt, solvate, or physiologically functional derivative thereof:
b is 1, 2, or 3;
y is 0, 1 or 2;
$R^x$ is independently selected from hydrogen, halogen, $C_1$-$C_6$ alkyl, $C_1$-$C_6$ hydroxyalkyl, —CN, —C(O)OH, —OC(O)R$^{11}$, $C_1$-$C_6$ haloalkyl, —NO$_2$, —OH, —OR$^9$, aryl, heteroaryl, heterocyclyl, —NR$^4$R$^5$, —R$^6$NR$^4$R$^5$, —C(O)N(H)R$^6$NR$^4$R$^5$, —S(O)$_y$R$^{10}$, —SO$_2$OH,
or
b is 2 and the two R$^x$ groups together with the phenyl group to which they are bound form a fused group selected from:

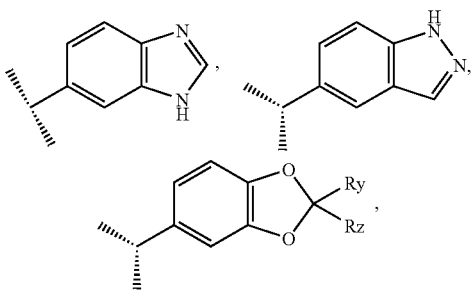

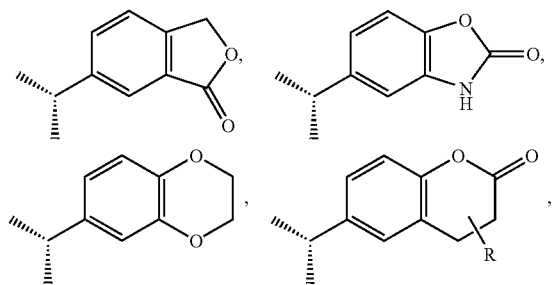

wherein $R_y$ and $R_z$ are independently selected from hydrogen and halogen,

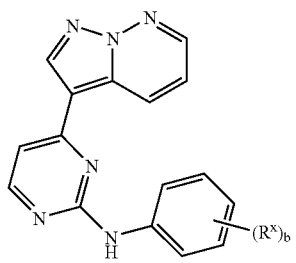

wherein R is selected from —CF3, halogen, or hydrogen;
$R^4$ and $R^5$ are independently hydrogen, $C_1$-$C_3$ alkyl, $C_3$-$C_7$ cycloalkyl, —C(O)$R^9$, or $R^4$ and $R^5$, together with the nitrogen atom to which they are bound, form a heterocyclyl;
$R^6$ is alkylene, arylene, heteroarylene, $C_3$-$C_7$ cycloalkylene, alkenylene, $C_3$-$C_7$ cycloalkenylene, or alkynylene;
$R^9$ is $C_1$-$C_6$ alkyl or $C_1$-$C_6$ haloalkyl;
$R^{10}$ is $NH_2$, $C_1$-$C_6$ alkyl, $C_1$-$C_6$ hydroxyalkyl, aryl, heteroaryl, or heterocyclyl; and
$R^{11}$ is $C_1$-$C_6$ alkyl.

In a sixth aspect of the present invention, there is provided a compound of Formula (IVa):

(IVa)

or a salt, solvate, or physiologically functional derivative thereof:
b is 1, 2, or 3;
y is 0, 1, or 2;
$R^x$ is independently selected from hydrogen, halogen, $C_1$-$C_6$ alkyl, $C_1$-$C_6$ hydroxyalkyl, —CN, —C(O)OH, —OC(O)$R^{11}$, $C_1$-$C_6$ haloalkyl, —$NO_2$, —OH, —O$R^9$, aryl, heteroaryl, heterocyclyl, —$NR^4R^5$, —$R^6NR^4R^5$, —C(O)N(H)$R^6NR^4R^5$, —S(O)$_y R^{10}$, —$SO_2OH$;

$R^4$ and $R^5$ are independently hydrogen, $C_1$-$C_3$ alkyl, $C_3$-$C_7$ cycloalkyl, —C(O)$R^9$, or $R^4$ and $R^5$, together with the nitrogen atom to which they are bound, form a heterocyclyl;
$R^6$ is alkylene, arylene, heteroarylene, $C_3$-$C_7$ cycloalkylene, alkenylene, $C_3$-$C_7$ cycloalkenylene, or alkynylene;
$R^9$ is $C_1$-$C_6$ alkyl or $C_1$-$C_6$ haloalkyl;
$R^{10}$ is $NH_2$, $C_1$-$C_6$ alkyl, $C_1$-$C_6$ hydroxyalkyl, aryl, heteroaryl, or heterocyclyl; and
$R^{11}$ is $C_1$-$C_6$ alkyl.

In a seventh aspect of the present invention, there is provided a pharmaceutical composition including a therapeutically effective amount of a compound of formula (I), or a salt, solvate, or a physiologically functional derivative thereof and one or more of pharmaceutically acceptable carriers, diluents and excipients.

In an eighth aspect of the present invention, there is provided a method of treating a disorder in a mammal, said disorder being mediated by inappropriate CDK activity, including: administering to said mammal a therapeutically effective amount of a compound of formula (I) or a salt, solvate or a physiologically functional derivative thereof.

In a ninth aspect of the present invention, there is provided a compound of formula (I), or a salt, solvate, or a physiologically functional derivative thereof for use in therapy.

In a tenth aspect of the present invention, there is provided the use of a compound of formula (I), or a salt, solvate, or a physiologically functional derivative thereof in the preparation of a medicament for use in the treatment of a disorder mediated by inappropriate CDK activity.

In an eleventh aspect of the present invention, there is provided a pharmaceutical composition including a therapeutically effective amount of a compound of formula (I), or a salt, solvate, or a physiologically functional derivative thereof and one or more of pharmaceutically acceptable carriers, diluents and excipients for preventing or reducing the severity of epithelial cytotoxicity in a subject receiving cytotoxic therapy.

In a twelfth aspect of the present invention, there is provided a a method of preventing or reducing the severity of epithelial cytotoxicity in a patient receiving cytotoxic therapy, comprising administering to said patient a therapeutically effective amount of a compound of formula (I) or a salt, solvate, or physiologically functional derivative thereof.

In a thirteenth aspect of the present invention, there is provided a method of treating cancer in a mammal, including administering to said mammal a therapeutically effective amount of a compound of formula (I), or salt, solvate or physiologically functional derivative thereof.

In a fourteenth aspect of the present invention, there is provided a method of treating cancer in a mammal, including administering to said mammal therapeutically effective amounts of (i) a compound of formula (I), or salt, solvate or physiologically functional derivative thereof and (ii) at least one additional anti-cancer therapy.

DETAILED DESCRIPTION OF THE INVENTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder; The term also includes within its scope amounts effective to enhance normal physiological function.

As used herein, the term "lower" refers to a group having between one and six carbons.

As used herein, the term "alkyl" refers to a straight or branched chain hydrocarbon having from one to twelve carbon atoms, optionally substituted with substituents selected from the group consisting of lower alkyl, lower haloalkyl, lower alkoxy, lower alkylsulfanyl, lower alkylsulfenyl, lower alkylsulfonyl, oxo, mercapto, amino optionally substituted by alkyl, carboxy, carbamoyl optionally substituted by alkyl, carboxamide optionally substituted by alkyl, aminosulfonyl optionally substituted by alkyl, nitro, or lower haloalkyl such as lower perfluoroalkyl, multiple degrees of substitution being allowed. Examples of "alkyl" as used herein include, but are not limited to, methyl, ethyl, propyl, n-butyl, n-pentyl, isobutyl, isopropyl, and the like.

As used herein, the terms "$C_1$-$C_3$ alkyl" and "$C_1$-$C_6$ alkyl" refer to an alkyl group, as defined above, which contains at least 1, and at most 3 or 6, carbon atoms respectively. Examples of "$C_1$-$C_3$ alkyl" and "$C_1$-$C_6$ alkyl" groups useful in the present invention include, but are not limited to, methyl, ethyl, propyl, isopropyl, isobutyl and n-butyl.

As used herein, the term "alkylene" refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, carboxamide optionally substituted by alkyl, aminosulfonyl optionally substituted by alkyl, nitro, cyano, halogen and lower haloalkyl such as lower perfluoroalkyl, multiple degrees of substitution being allowed. Examples of "alkylene" as used herein include, but are not limited to, methylene, ethylene, n-propylene, n-butylene, and the like.

As used herein, the terms "$C_1$-$C_3$ alkylene" and "$C_1$-$C_4$ alkylene" refer to an alkylene group, as defined above, which contains at least 1, and at most 3 or 4, carbon atoms respectively. Examples of "$C_1$-$C_3$ alkylene" and "$C_1$-$C_4$ alkylene" groups useful in the present invention include, but are not limited to, methylene, ethylene, n-propylene, isopropylene, and n-butylene.

As used herein, the term "alkenyl" refers to a hydrocarbon radical having from two to ten carbons and at least one carbon-carbon double bond, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, carboxamide optionally substituted by alkyl, aminosulfonyl optionally substituted by alkyl, nitro, cyano, halogen and lower haloalkyl such as lower perfluoroalkyl, multiple degrees of substitution being allowed. Examples of "alkenyl" as used herein include, ethenyl, propenyl, 1-butenyl, 2-butenyl, and isobutenyl.

As used herein, the terms "$C_2$-$C_4$ alkenyl" and "$C_2$-$C_6$ alkenyl" refers to an alkenyl group as defined above containing at least 2, and at most 4 or 6, carbon atoms respectively. Examples of "$C_2$-$C_4$ alkenyl" and "$C_2$-$C_6$ alkenyl" groups useful in the present invention include, but are not limited to, ethenyl, propenyl, 1-butenyl, 2-butenyl, and isobutenyl.

As used herein, the term "alkenylene" refers to an straight or branched chain divalent hydrocarbon radical having from two to ten carbon atoms and one or more carbon-carbon double bonds, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, carboxamide optionally substituted by alkyl, aminosulfonyl optionally substituted by alkyl, nitro, cyano, halogen and lower haloalkyl such as lower perfluoroalkyl, multiple degrees of substitution being allowed. Examples of "alkenylene" as used herein include, but are not limited to, ethene-1,2-diyl, propene-1,3-diyl, butene-1,2-diyl, and the like.

As used herein, the term "$C_2$-$C_3$ alkenylene" refers to an alkenylene group as defined above containing at least 2, and at most 3, carbon atoms. Examples of "$C_2$-$C_3$ alkenylene" groups useful in the present invention include, but are not limited to, ethene-1,2-diyl, propene-1,3-diyl, and the like.

As used herein, the term "alkynyl" refers to a hydrocarbon radical having from two to ten carbons and at least one carbon-carbon triple bond, optionally substituted with substituents selected from the group which includes lower alkyl, lower alkoxy, lower alkylsulfanyl, lower alkylsulfenyl, lower alkylsulfonyl, oxo, aryl, hydroxy, mercapto, amino optionally substituted by alkyl, carboxy, carbamoyl optionally substituted by alkyl, carboxamide optionally substituted by alkyl, aminosulfonyl optionally substituted by alkyl, nitro, cyano, halogen and lower haloalkyl such as lower perfluoroalkyl, multiple degrees of substitution being allowed. Examples of "alkynyl" as used herein, include but are not limited to acetylenyl, propynyl, 1-butynyl, 2-butynyl, 1-pentynyl, and 1-hexynyl.

As used herein, the terms "$C_2$-$C_4$ alkynyl" and "$C_2$-$C_6$ alkynyl" refers to an alkynyl group as defined above containing at least 2, and at most 4 or 6, carbon atoms respectively. Examples of "$C_2$-$C_4$ alkynyl" and "$C_2$-$C_6$ alkynyl" groups useful in the present invention include, but are not limited to, acetylenyl, propynyl, 1-butynyl, 2-butynyl, 1-pentynyl, and 1-hexynyl.

As used herein, the term "alkynylene" refers to a straight or branched chain divalent hydrocarbon radical having from two to ten carbon atoms and one or more carbon-carbon triple bonds, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, carboxamide optionally substituted by alkyl, aminosulfonyl optionally substituted by alkyl, nitro, cyano, halogen and lower haloalkyl such as lower perfluoroalkyl, multiple degrees of substitution being allowed. Examples of "alkynylene" as used herein include, but are not limited to, ethyne-1,2-diyl, propyne-1,3-diyl, and the like.

As used herein, the terms "$C_2$-$C_6$ alkynylene", refers to an alkynylene group as defined above containing at least 2, and at most 6, carbon atoms. Examples of "$C_2$-$C_6$ alkynylene" groups useful in the present invention include, but are not limited to, ethyne-1,2-diyl, propyne-1,3-diyl, and the like.

As used herein, the term "halogen" or "halo" refers to fluoro (—F), chloro (—Cl), bromo (—Br), or iodo (—I).

As used herein, the term "$C_1$-$C_6$ haloalkyl" refers to a straight or branched chain hydrocarbon containing at least 1, and at most 6, carbon atoms substituted with at least one halogen, halogen being as defined herein. Examples of branched or straight chained "$C_1$-$C_6$ haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

As used herein, the term "$C_1$-$C_6$ hydroxyalkyl" refers to a straight or, branched chain hydrocarbon containing at least 1, and at most 6, carbon atoms substituted with at least one hydroxy, hydroxy being as defined herein. Examples of branched or straight chained "$C_1$-$C_6$ hydroxyalkyl" groups useful in the present invention include, but are not limited to, methyl, ethyl, propyl, isopropyl, isobutyl and n-butyl substituted independently with one or more hydroxy groups.

As used herein, the term "cycloalkyl" refers to a non-aromatic cyclic hydrocarbon ring having from three to twelve carbon atoms, which optionally includes a $C_1$-$C_4$ alkylene linker through which it may be attached. Exemplary "cycloalkyl" groups include, but are not limited to, cyclopropyl, cyclobutyl, cyclopentyl, cyclohexyl and cycloheptyl.

As used herein, the term "$C_3$-$C_7$ cycloalkyl" refers to a cycloalkyl group as defined above having from three to seven carbon atoms, which also optionally includes a $C_1$-$C_4$ alkylene linker through which it may be attached. Exemplary "$C_3$-$C_7$ cycloalkyl" groups include, but are not limited to, cyclopropyl, cyclobutyl, cyclopentyl, cyclohexyl and cycloheptyl.

As used herein, the term "$C_3$-$C_7$ cycloalkylene" refers to a non-aromatic alicyclic divalent hydrocarbon radical having from three to seven carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, carboxamide optionally substituted by alkyl, aminosulfonyl optionally substituted by alkyl, nitro, cyano, halogen, lower haloalkyl such as lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "$C_3$-$C_7$ cycloalkenyl" refers to a non-aromatic cyclic hydrocarbon ring having from three to seven carbon atoms, and one or more carbon—carbon double bonds, which optionally includes a $C_1$-$C_4$ alkylene linker through which it may be attached. Exemplary "$C_3$-$C_7$ cycloalkenyl" groups include, but are not limited to, cyclobutenyl, cyclopentenyl, cyclohexenyl and cycloheptenyl.

As used herein, the term "$C_3$-$C_7$ cycloalkenylene" refers to a non-aromatic alicyclic divalent hydrocarbon radical having from three to seven carbon atoms, and one or more carbon-carbon double bonds optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, carboxamide optionally substituted by alkyl, aminosulfonyl optionally substituted by alkyl, nitro, cyano, halogen, lower haloalkyl such as lower perfluoroalkyl, multiple degrees of substitution being allowed.

Examples of "cycloalkenylene" as used herein include, but are not limited to, 4,5-cyclopentene-1,3-diyl, 3,4-cyclohexene-1,1-diyl, and the like.

As used herein, the term "heterocyclic" or the term "heterocyclyl" refers to a three to twelve-membered heterocyclic, non-aromatic, ring being unsaturated or having one or more degrees of unsaturation containing one or more heteroatomic substitutions selected from S, SO, $SO_2$, O, or N, said ring being optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, carboxamide optionally substituted by alkyl, aminosulfonyl optionally substituted by alkyl, nitro, cyano, halogen, or lower haloalkyl such as lower perfluoroalkyl, multiple degrees of substitution being allowed. Such a ring may be optionally fused to one or more of another "heterocyclic" ring(s), cycloalkyl ring(s), or aryl ring(s). Examples of "heterocyclic" include, but are not limited to, tetrahydrofuranyl, pyranyl, 1,4-dioxanyl, 1,3-dioxanyl, 1,3-benzodioxol-5-yl, 2,3-dihydro-1,4-benzodioxin-6-yl, piperidinyl, pyrrolidinyl, piperizinyl, 4-methyl-1-piperizinyl, 2-pyrrolidinone, morpholinyl, 4-morpholinyl propyl, tetrahydrothiopyranyl, tetrahydrothiophenyl, and the like.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include lower alkyl, lower alkoxy, lower haloalkoxy, lower alkylsulfanyl, lower alkylsulfenyl, lower alkylsulfonyl, arylsulfanyl, heterocyclylsulfonyl, sulfo, oxo, hydroxy, mercapto, amino optionally substituted by alkyl or acyl, carboxy, carbamoyl optionally substituted by alkyl, carboxamide optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower haloalkyl such as lower perfluoroalkyl, heterocyclyl, heteroaryl, or aryl, multiple degrees of substitution being allowed. Examples of "aryl" groups include, but are not limited to, phenyl, 2-naphthyl, 1-naphthyl, biphenyl, as well as substituted derivatives thereof.

As used herein, the term "arylene" refers to a benzene ring diradical or to a benzene ring system diradical fused to one or more optionally substituted benzene rings, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, carboxamide optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower haloalkyl such as lower perfluoroalkyl, heteroaryl and aryl, multiple degrees of substitution being allowed. Examples of "arylene" include, but are not limited to, benzene-1,4-diyl, naphthalene-1,8-diyl, anthracene-1,4-diyl, and the like.

As used herein, the term "aralkyl" refers to an aryl or heteroaryl group, as defined herein, attached through a lower alkylene linker, wherein lower alkylene is as defined herein. Examples of "aralkyl" include, but are not limited to, benzyl, phenylpropyl, 2-pyridylmethyl, 3-isoxazolylmethyl, 5-methyl-3-isoxazolylmethyl, and 2-imidazoyly ethyl.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen heteroatoms, where N-oxides and sulfur oxides and dioxides are permissible heteroatom substitutions and may be optionally substituted with up to three members selected from a group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, carboxamide optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower haloalkyl such as lower perfluoroalkyl, heteroaryl, or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, is oxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzimidazolyl, benzoxazolyl, benzothiophenyl, indolyl, indazolyl, and substituted versions thereof.

As used herein, the term "heteroarylene" refers to a five to seven membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of: lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, carboxamide optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower haloalkyl such as lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophen-2,4-diyl, 1,3,4-oxadiazol-2,5-diyl, 1,3,4-thiadiazol-2,5-diyl, 1,3-thiazol-2,4-diyl, 1,3-thiazol-2,5-diyl, pyridin-2,4-diyl, pyridin-2,3-diyl, pyridin-2,5-diyl, pyrimidin-2,4-diyl, quinolin-2,3-diyl, and the like.

As used herein, the term "hydroxy" refers to the group —OH.

As used herein, the term "alkoxy" refers to the group $R_aO$—, where $R_a$ is alkyl as defined above and the terms "$C_1$-$C_3$ alkoxy" and "$C_1$-$C_6$ alkoxy" refer to the group $R_aO$—, where $R_a$ is $C_1$-$C_3$ alkyl or $C_1$-$C_6$ alkyl respectively as defined above.

As used herein, the term "haloalkoxy" refers to the group $R_aO$—, where $R_a$ is haloalkyl as defined above and the terms "$C_1$-$C_3$ haloalkoxy" and "$C_1$-$C_6$ haloalkoxy" refer to the group $R_aO$—, where $R_a$ is $C_1$-$C_3$ haloalkyl or $C_1$-$C_6$ haloalkyl respectively as defined above.

As used herein the term "aralkoxy" refers to the group $R_bR_aO$—, where $R_a$ is alkylene and $R_b$ is aryl, both as defined above.

As used herein, the term "alkylsulfanyl" refers to the group $R_aS$—, where $R_a$ is alkyl as defined above.

As used herein, the term "arylsulfanyl" refers to the group $R_aS$—, where $R_a$ is aryl as defined above.

As used herein, the term "alkylsulfenyl" refers to the group $R_aS(O)$—, where $R_a$ is alkyl as defined above.

As used herein, the term "alkylsulfonyl" refers to the group $R_aS(O)_2$—, where $R_a$ is alkyl as defined above.

As used herein, the term "heterocyclylsulfonyl" refers to the group $R_aS(O)_2$—, where $R_a$ is heterocyclyl as defined above.

As used herein, the term "oxo" refers to the group =O.

As used herein, the term "mercapto" refers to the group —SH.

As used herein, the term "carboxy" refers to the group —COOH.

As used herein, the term "cyano" refers to the group —CN.

As used herein the term "cyanoalkyl" refers to the group —$R_a$CN wherein $R_a$ is $C_1$-$C_3$ alkylene as defined above. Exemplary "cyanoalkyl" groups useful in the present invention include, but are not limited to, cyanomethyl, cyanoethyl, and cyanopropyl.

As used herein the term "nitro" refers to the group —$NO_2$.

As used herein the term "azido" refers to the group —$N_3$.

As used herein, the term "aminosulfonyl" refers to the group —$SO_2NH_2$.

As used herein, the term "carbamoyl" refers to the group —OC(O)NHR$_a$, where $R_a$ is hydrogen or alkyl as defined herein.

As used herein, the term "carboxamide" refers to the group —C(O)NH$_2$.

As used herein, the term "sulfanyl" shall refer to the group —S—.

As used herein, the term "sulfenyl" shall refer to the group —S(O)—.

As used herein, the term "sulfonyl" shall refer to the group —S(O)$_2$— or —SO$_2$—.

As used herein, the term "sulfo" shall refer to the group —S(O)$_2$OH.

As used herein, the term "acyl" refers to the group $R_aC(O)$—, where $R_a$ is alkyl, cycloalkyl, or heterocyclyl as defined herein.

As used herein, the term "aroyl" refers to the group $R_aC(O)$—, where $R_a$ is aryl as defined herein.

As used herein, the term "heteroaroyl" refers to the group $R_aC(O)$—, where $R_a$ is heteroaryl as defined herein.

As used herein, the term "alkoxycarbonyl" refers to the group $R_aOC(O)$—, where $R_a$ is alkyl as defined herein.

As used herein, the term "acyloxy" refers to the group $R_aC(O)O$—, where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the, group $R_aC(O)O$—, where $R_a$ is heteroaryl as defined herein.

As used herein, the term "optionally" means that the subsequently described event(s) may or may not occur, and includes both event(s), which occur, and events that do not occur.

As used herein, the term "physiologically functional derivative" refers to any pharmaceutically acceptable derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I) (II), (III), (IV), or (IVa) or a salt or physiologically functional derivative thereof and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

The compounds of formulae (I), (II), (III), (IV), or (IVa) have the ability to, crystallize in more than one form, a characteristic, which is known as polymorphism, and it is understood that such polymorphic forms ("polymorphs") are within the scope of formulae (I), (II), (III), (IV), and (IVa). Polymorphism generally can occur as a response to changes in temperature or pressure or both and can also result from variations in the crystallization process. Polymorphs can be distinguished by various physical characteristics known in the art such as x-ray diffraction patterns, solubility, and melting point.

As used herein, the term "substituted" refers to substitution with the named substituent or substituents, multiple degrees of substitution being allowed unless otherwise stated.

Certain of the compounds described herein may contain one or more chiral atoms, or may otherwise be capable of existing as two enantiomers. Accordingly, the compounds of this invention may include mixtures of enantiomers as well as purified enantiomers or enantiomerically enriched mixtures. Also included within the scope of the invention are the individual isomers of the compounds represented by formula (I), (II), (III), (IV), and (IVa) above as well as any wholly or partially equilibrated mixtures thereof. The present invention also covers the individual isomers of the compounds represented by the formulas above as mixtures with isomers thereof in which one or more chiral centers are inverted.

It is to be understood that the following embodiments refer to compounds within the scope of formula (I), formula (II), formula (III), formula (IV), and formula (IVa) as defined above unless specifically limited by the definition of each formula or specifically limited otherwise. It is also understood that the, embodiments of the present invention described herein, including uses and compositions, while typically described in terms of formula (I) are also applicable to compounds of formula (II), formula (III), formula (IV) and formula (IVa).

It is also understood that the recited "aryl", "heteroaryl", or "heterocycyl" groups may optionally be substituted as indicated above in the definitions for "aryl", "heteroaryl", and "heterocyclyl" respectively. Furthermore, such "aryl", "heteroaryl", and "heterocyclyl" groups may be substituted as specifically indicated with additional groups other than those recited in said definitions.

In one embodiment, D is N. In another embodiment, D is CH.

In one embodiment, $R^1$ is hydrogen or $C_1$-$C_6$ alkyl. In a preferred embodiment, $R^1$ is hydrogen. In another embodiment, $R^1$ is $C_1$-$C_6$ alkyl, preferably methyl, ethyl, or n-butyl.

In one embodiment, $R^2$ is hydrogen, $C_1$-$C_6$ alkenyl, heterocyclyl, aryl, heteroaryl, —$OR^8$, $S(O)_yR^{10}$, and —$NR^4R^5$. In a preferred embodiment, $R^2$ is hydrogen, heterocyclyl, aryl, heteroaryl, or —$OR^8$. In a more preferred embodiment, $R^2$ is hydrogen. In another embodiment, $R^2$ is —$OR^8$, wherein $R^8$ is hydrogen, methyl and isopropyl.

In an alternative embodiment, $R^2$ is heterocyclyl, preferably morpholinyl or pyrrolidinyl; aryl, preferably phenyl; or heteroaryl, preferably pyridinyl or thienyl.

In one embodiment, Q is $N(R^8)$, p is 1, and $Q^1$ is $C_1$-$C_6$ alkyl, $C_3$-$C_7$ cycloalkyl, $C_1$-$C_6$ haloalkyl, or aryl. In a preferred embodiment, Q is $N(R^8)$, p is 1, and $Q^1$ is $C_3$-$C_7$ cycloalkyl. In a more preferred embodiment, Q is $N(R^8)$, p is 1, and $Q^1$ is cyclopropyl.

In another embodiment, Q is $N(R^8)$, p is 1, and $Q^1$ is aryl. In a preferred embodiment, Q is $N(R^8)$, p is 1, and $Q^1$ is phenyl or phenyl substituted with at least one of $C_1$-$C_6$ alkyl, halogen, cyano, carboxy, $C_1$-$C_6$ haloalkyl, $C_1$-$C_6$ alkoxy, nitro, heteroaryl, or heterocyclyl.

In one embodiment Q is $S(O)_y$, p is 1, y is 0, and $Q^1$ is $C_1$-$C_6$ alkyl, preferably methyl. In another embodiment Q is 0, p is 1, and $Q^1$ is $C_1$-$C_6$ alkyl, preferably isopropyl.

In one embodiment, the compound of formula (I) is a compound of Formula (II):

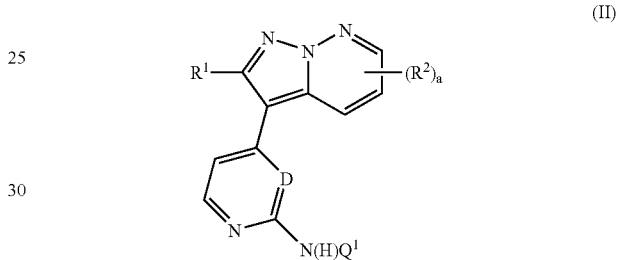

(II)

or a salt, solvate, or physiologically functional derivative thereof.

In one embodiment, the compound of formula (I) is a compound of formula (III):

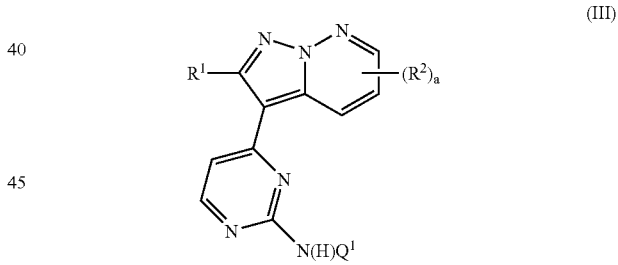

(III)

or a salt, solvate, or physiologically functional derivative thereof.

In another embodiment, the compound of formula (I) is a compound of formula (IV):

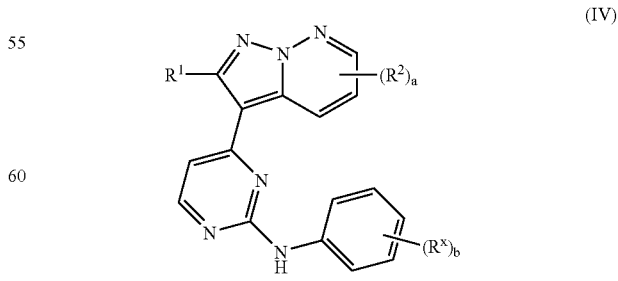

(IV)

or a salt, solvate, or physiologically functional derivative thereof, wherein b is 1, 2, or 3 and $R^x$ is hydrogen, halogen, $C_1$-$C_6$ alkyl, $C_1$-$C_6$ hydroxyalkyl, —CN, —C(O)OH, —OC(O)$R^{11}$, $C_1$-$C_6$ haloalkyl, —NO$_2$, —OH, —OR$^9$, aryl, heteroaryl, heterocyclyl, —NR$^4$R$^5$, —R$^6$NR$^4$R$^5$, —C(O)N(H)R$^6$NR$^4$R$^5$, —S(O)$_y$R$^{10}$, or —SO$_2$OH; preferably, b is 1 or 2 and R$^x$ is halogen, $C_1$-$C_6$ alkyl, $C_1$-$C_6$ hydroxyalkyl, —CN, $C_1$-$C_6$ haloalkyl, —NO$_2$, heterocyclyl, or —NR$^4$R$^5$; more preferably, b is 1 and R$^x$ is —CH$_3$, —CH$_2$CH$_3$, —CF$_3$, —CN, or —NO$_2$; alternatively b is 2 and the two R$^x$ groups together with the phenyl group to which they are bound form a fused group selected from:

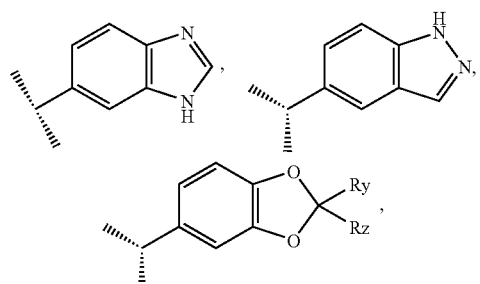

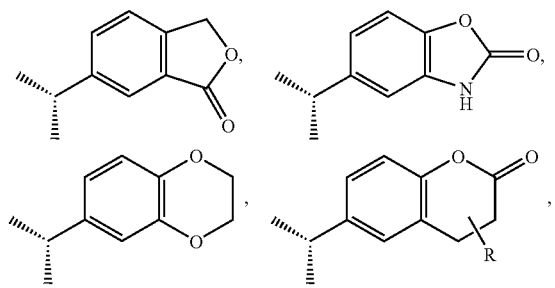

wherein R$_y$ and R$_z$ are independently selected from hydrogen and halogen,

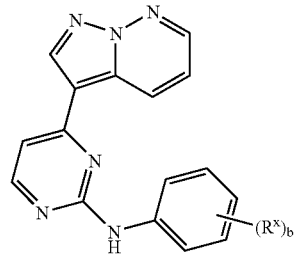

wherein R is selected from —CF$_3$, halogen, or hydrogen.

In another embodiment, the compound of formula (I) is a compound of formula (IVa):

(IVa)

[structure]

or a salt, solvate, or physiologically functional derivative thereof, wherein, b is 1, 2, or 3 and R$^x$ is hydrogen, halogen, $C_1$-$C_6$ alkyl, $C_1$-$C_6$ hydroxyalkyl, —CN, —C(O)OH, —OC(O)R$^{11}$, $C_1$-$C_6$ haloalkyl, —NO$_2$, —OH, —OR$^9$, aryl, heteroaryl, heterocyclyl, —NR$^4$R$^5$, —R$^6$NR$^4$R$^5$, —C(O)N(H)R$^6$NR$^4$R$^5$, —S(O)$_y$R$^{10}$, or —SO$_2$OH; preferably, b is 1 or 2 and R$^x$ is halogen, $C_1$-$C_6$ alkyl, $C_{1-6}$ hydroxyalkyl, —CN, $C_1$-$C_6$ haloalkyl, —NO$_2$, heterocyclyl, or —NR$^4$R$^5$; more preferably, b is 1 and R$^x$ is —CH$_3$, —CH$_2$CH$_3$, —CF$_3$, —CN, or —NO$_2$; alternatively b is 2 and the two R$^x$ groups together with the phenyl group to which they are bound form a fused group selected from:

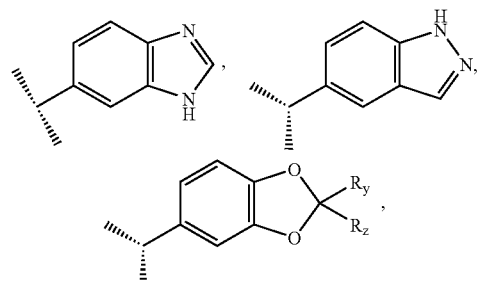

wherein R$_y$ and R$_z$ are independently selected from hydrogen and halogen,

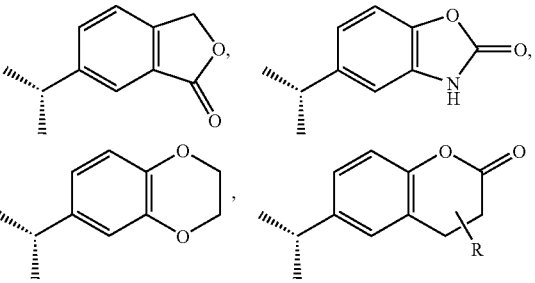

wherein R is selected from —CF$_3$, halogen, or hydrogen;

In another embodiment, the compound of formula (I) is a compound of Formula (IVa):

(IVa)

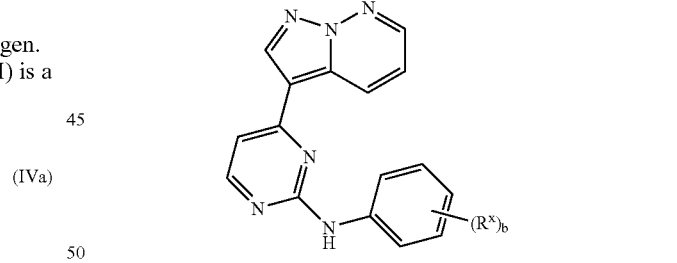

or a salt, solvate, or physiologically functional derivative thereof, wherein b is 1, 2, or 3; y is 0, 1, or 2; and R$^x$ is independently selected from hydrogen, halogen, $C_1$-$C_6$ alkyl, $C_1$-$C_6$ hydroxyalkyl, —CN, —C(O)OH, —OC(O)R$^{11}$, $C_1$-$C_6$ haloalkyl, —NO$_2$, —OH, —OR$^9$, aryl, heteroaryl, heterocyclyl, —NR$^4$R$^5$, —R$^6$NR$^4$R$^5$, —C(O)N(H)R$^6$NR$^4$R$^5$, —S(O)$_y$R$^{10}$, —SO$_2$OH; preferably b is 1 or 2 and R$^x$ is independently selected from hydrogen, halogen, $C_1$-$C_6$ alkyl, —CN, —C(O)OH, —$C_1$-$C_6$ haloalkyl, —NO$_2$, —OH, —OR$^9$; more preferably preferably b is 1 or 2 and R$^x$ is independently selected from hydrogen, halogen, —CN, —$C_1$-$C_6$ haloalkyl, or —NO$_2$; most preferably preferably b is 1 and R$^x$ is selected from —F, —CH$_3$, —CN, —CF$_3$, or —NO$_2$.

Specific examples of compounds of the present invention include the following:

N-cyclopropyl-4-pyrazolo[1,5-b]pyridazin-3-yl-2-pyrimidinamine;
N-cyclopropyl-N-methyl-4-pyrazolo[1,5-b]pyridazin-3-yl-2-pyrimidinamine;
4-pyrazolo[1,5-b]pyridazin-3-yl-N-(2,2,2-trifluoroethyl)-2-pyrimidinamine;
N-phenyl-4-pyrazolo[1,5-b]pyridazin-3-yl-2-pyrimidinamine;
N-(4-chlorophenyl)-4-pyrazolo[1,5-b]pyridazin-3-yl-2-pyrimidinamine;
N-(4-fluorophenyl)-4-pyrazolo[1,5-b]pyridazin-3-yl-2-pyrimidinamine;
3-[(4-pyrazolo[1,5-b]pyridazin-3-yl-2-pyrimidinyl)amino]benzonitrile;
4-[(4-pyrazolo[1,5-b]pyridazin-3-yl-2-pyrimidinyl)amino]benzoic acid;
4-pyrazolo[1,5-b]pyridazin-3-yl-N-[3-(trifluoromethyl)phenyl]-2-pyrimidinamine;
N-(3-nitrophenyl)-4-pyrazolo[1,5-b]pyridazin-3-yl-2-pyrimidinamine;
N-(2-chlorophenyl)-4-pyrazolo[1,5-b]pyridazin-3-yl-2-pyrimidinamine;
N-(4-methoxyphenyl)-4-pyrazolo[1,5-b]pyridazin-3-yl-2-pyrimidinamine;
4-pyrazolo[1,5-b]pyridazin-3-yl-N-(3,4,5-trimethoxyphenyl)-2-pyrimidinamine;
N-[3-(1,3-oxazol-5-yl)phenyl]-4-pyrazolo[1,5-b]pyridazin-3-yl-2-pyrimidinamine;
N-(4-pyrazolo[1,5-b]pyridazin-3-yl-2-pyrimidinyl)-1H-benzimidazol-6-amine;
N-(4-pyrazolo[1,5-b]pyridazin-3-yl-2-pyrimidinyl)-1,3-benzoxazol-2-amine;
N-(6-chloro-1H-benzimidazol-2-yl)-N-(4-pyrazolo[1,5-b]pyridazin-3-yl-2-pyrimidinyl)amine;
N-(+chlorobenzyl)-4-pyrazolo[1,5-b]pyridazin-3-yl-2-pyrimidinamine;
$N^1,N^1$-dimethyl-$N^3$-(4-pyrazolo[1,5-b]pyridazin-3-yl-2-pyrimidinyl)-1,3-propanediamine methanesulfonate;
N-[3-(4-morpholinyl)propyl]-pyrazolo[1,5-b]pyridazin-3-yl-2-pyrimidinamine;
N-[3-(4-methyl-1-piperazinyl)propyl]-4-pyrazolo[1,5-b]pyridazin-3-yl-2-pyrimidinamine;
1-{3-[(4-pyrazolo[1,5-b]pyridazin-3-yl-2-pyrimidinyl)amino]propyl}-2-pyrrolidinone;
N-[3-chloro-4-(4-methyl-1-piperazinyl)phenyl]-4-pyrazolo[1,5-b]pyridazin-3-yl-2-S pyrimidinamine;
N-[4-(4-methyl-1-piperazinyl)phenyl]-4-pyrazolo[1,5-b]pyridazin-3-yl-2-pyrimidinamine;
N-[3-methyl-4-(4-methyl-1-piperazinyl)phenyl]-4-pyrazolo[1,5-b]pyridazin-3-yl-2-pyrimidinamine;
N-[4-(4-methyl-1-piperazinyl)-3-(trifluoromethyl)phenyl]-4-pyrazolo[1,5-b]pyridazin-3-yl-2-pyrimidinamine;
N-[3-chloro-4-(4-morpholinyl)phenyl]-4-pyrazolo[1,5-b]pyridazin-3-yl-2-pyrimidinamine;
N-{4-[(diethylamino)methyl]phenyl}-4-pyrazolo[1,5-b]pyridazin-3-yl-2-pyrimidinamine;
N-[2-(diethylamino)ethyl]-4-[(4-pyrazolo[1,5-b]pyridazin-3-yl-2-pyrimidinyl)amino]benzamide;
N-cyclopropyl-4-(2-methylpyrazolo[1,5-b]pyridazin-3-yl)-2-pyrimidinamine;
N-cyclopropyl-4-(2-ethylpyrazolo[1,5-b]pyridazin-3-yl)-2-pyrimidinamine;
4-(2-butylpyrazolo[1,5-b]pyridazin-3-yl)-N-cyclopropyl-2-pyrimidinamine;
N-[4-(4-methyl-1-piperazinyl)phenyl]-4-(2-methylpyrazolo[1,5-b]pyridazin-3-yl)-2-pyrimidinamine;
4-(2-ethylpyrazolo[1,5-b]pyridazin-3-yl)-N-[4-(4-methyl-1-piperazinyl)phenyl]-2-pyrimidinamine;
4-(2-butylpyrazolo[1,5-b]pyridazin-3-yl)-N-[4-(4-methyl-1-piperazinyl)phenyl]-2-pyrimidinamine;
N-cyclopropyl-4-(6-methoxypyrazolo[1,5-b]pyridazin-3-yl)-2-pyrimidinamine;
4-(6-methoxypyrazolo[1,5-b]pyridazin-3-yl)-N-[4-(4-methyl-1-piperazinyl)phenyl]-2-pyrimidinamine;
3-[2-(cyclopropylamino)-4-pyrimidinyl]pyrazolo[1,5-b]pyridazin-6-ol;
N-cyclopropyl-4-(6-isopropoxypyrazolo[1,5-b]pyridazin-3-yl)-2-pyrimidinamine;
N-[4-(6-isopropoxypyrazolo[1,5-b]pyridazin-3-yl)-2-pyrimidinyl]-N-[4-(4-methyl-1-piperazinyl)phenyl]amine;
3-[2-(cyclopropylamino)-4-pyrimidinyl]pyrazolo[1,5-b]pyridazin-6-yl trifluoromethanesulfonate;
4-[6-(2-chlorophenyl)pyrazolo[1,5-b]pyridazin-3-yl]-N-cyclopropyl-2-pyrimidinamine;
N-cyclopropyl-4-[6-(2-thienyl)pyrazolo[1,5-b]pyridazin-3-yl]-2-pyrimidinamine;
N-cyclopropyl-4-[6-(4-fluorophenyl)pyrazolo[1,5-b]pyridazin-3-yl]-2-pyrimidinamine;
N-cyclopropyl-4-(6-vinylpyrazolo[1,5-b]pyridazin-3-yl)-2-pyrimidinamine;
N-cyclopropyl-4-[6-(4-morpholinyl)pyrazolo[1,5-b]pyridazin-3-yl]-2-pyrimidinamine; N-cyclopentyl-3-[2-(cyclopropylamino)-4-pyrimidinyl]pyrazolo[1,5-b]pyridazin-6-amine;
N-cyclopropyl-4-[6-(1-pyrrolidinyl)pyrazolo[1,5-b]pyridazin-3-yl]-2-pyrimidinamine;
N-cyclopropyl-4-[6-(2-fluoro-4-pyridinyl)pyrazolo[1,5-b]pyridazin-3-yl]-2-pyrimidinamine;
N-cyclopropyl-4-[6-(phenylsulfanyl)pyrazolo[1,5-b]pyridazin-3-yl]-2-pyrimidinamine;
4-[6-(4-fluorophenyl)pyrazolo[1,5-b]pyridazin-3-yl]-N-(4-methoxyphenyl)-2-pyrimidinamine;
4-[6-(4-fluorophenyl)pyrazolo[1,5-b]pyridazin-3-yl]-N-[4-(4-methyl-1-piperazinyl)phenyl]-2-pyrimidinamine;
$N^1,N^1$-dimethyl-$N^4$-{4-[6-(4-morpholinyl)pyrazolo[1,5-b]pyridazin-3-yl]-2-pyrimidinyl}-1,4-benzenediamine;
1-(dimethylamino)-3-[4-({4-[6-(4-morpholinyl)pyrazolo[1,5-b]pyridazin-3-yl]-2-pyrimidinyl}amino)phenoxy]-2-propanol;
N-(1,3-benzodioxol-5-yl)-4-pyrazolo[1,5-b]pyridazin-3-yl-2-pyrimidinamine;
N-(2,3-dihydro-1,4-benzodioxin-6-yl)-4-pyrazolo[1,5-b]pyridazin-3-yl-2-pyrimidinamine;
N-[3-methoxy-5-(trifluoromethyl)phenyl]-4-pyrazolo[1,5-b]pyridazin-3-yl-2-pyrimidinamine;
4-[(4-pyrazolo[1,5-b]pyridazin-3-yl-2-pyrimidinyl)amino]benzonitrile;
N-(4-nitrophenyl)-4-pyrazolo[1,5-b]pyridazin-3-yl-2-pyrimidinamine;
N-(3-methoxyphenyl)-4-pyrazolo[1,5-b]pyridazin-3-yl-2-pyrimidinamine;
N-(3,5-dimethylphenyl)-4-pyrazolo[1,5-b]pyridazin-3-yl-2-pyrimidinamine;
N-(4-aminosulfonylphenyl)-4-pyrazolo[1,5-b]pyridazin-3-yl-2-pyrimidinamine; and
N-(4-methylsulfonylphenyl)-4-pyrazolo[1,5-b]pyridazin-3-yl-2-pyrimidinamine; or salts, solvates, and physiologically functional derivatives thereof.

Additional examples of compounds of the present invention, which can be prepared according to the Schemes and Examples following are depicted in Table I:

TABLE 1

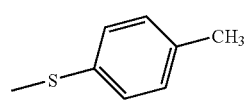

(IVc)

| # | A | D | E | J |
|---|---|---|---|---|
| 62 | —CF₃ | —H | —H | —H |
| 63 | —SO₂NH₂ | —H | —H | —H |
| 64 | —H | —H | —CF₃ | —H |
| 65 | —H | —F | —H | —H |
| 66 | —H | —CH₃ | —H | —H |
| 67 | —H | —CH₃ | —N(H)C(O)CH₃ | —H |
| 68 | —H | —CH₂CH3 | —H | —H |
| 69 | —H | —CH(CH₃)CH₃ | —H | —H |
| 70 | —H | —C(CH₃)₃ | —H | —H |
| 71 | —H | —C(O)OH | —H | —H |
| 72 | —H | —CH(OH)CH₃ | —H | —H |
| 73 | —H | —S(O)₂NH₂ | —H | —H |
| 74 | —H | —S(O)₂CH₂CH₂OH | —H | —H |
| 75 | —H | —S(O)₂OH | —Cl | —H |
| 76 | —H | —OCF₃ | —H | —H |
| 77 | —H | —OCF₂CF₂H | —H | —H |
| 78 | —H | —N(CH₃)₂ | —H | —H |
| 79 | —Cl | —H | —S(O)₂CH₃ | —H |
| 80 | —F | —NO₂ | —H | —H |
| 81 | —H | —NO₂ | —F | —H |
| 82 | —H | —NO₂ | —OH | —H |
| 83 | —H | —NO₂ | —C(O)OH | —H |
| 84 | —H | —NO₂ | —S(O)₂OH | —H |
| 85 | —H | —NO₂ | —CF₃ | —H |
| 86 | —H | —NO₂ | —H | —OCH₃ |
| 87 | —H | —NO₂ | —H | —C(O)OH |
| 88 | —H | —NO₂ | —H | —H |
| 89 | —H | —CN | —CH₃ | —H |
| 90 | —H | —CN | —Cl | —H |
| 91 | —H | —CN | —F | —H |
| 92 | —H | —CN | 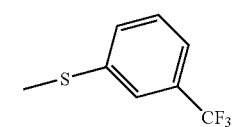 | —H |
| 93 | —H | —CN | 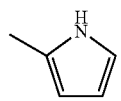 | —H |
| 94 | —H | —CN | —OH | —H |
| 95 | —H | —CN | —H | —CF₃ |
| 96 | —H | —CN | (2-methylpyrrole) | —H |
| 97 | —H | —CF₃ | —F | —H |
| 98 | —H | —CF₃ | —NO₂ | —H |
| 99 | —H | —CF₃ | —CN | —H |
| 100 | —H | —CF₃ | —OCH₃ | —H |
| 101 | —H | —CF₃ | —CH₃ | —H |
| 102 | —H | —CF₃ | —OH | —H |
| 103 | —H | —CF₃ | —H | —F |
| 104 | —H | —CF₃ | —H | —C(O)OH |
| 105 | —H | —CF₃ | —H | —NO₂ |
| 106 | —H | —CF₃ | —H | —OH |

TABLE 1-continued (IVc)

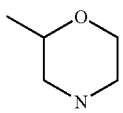

| # | A | D | E | J |
|---|---|---|---|---|
| 107 | —H | —CF₃ | —H | —OC(O)CH₃ |
| 108 | —Cl | —CF₃ | —H | —H |
| 109 | —CH₃ | —CF₃ | —H | —H |
| 110 | —H | —CF3 | 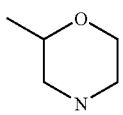 | —H |
| 111 | —H | —C(O)OH | 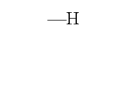 | —H |
| 112 | —H | —S(O)₂— 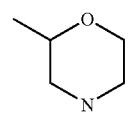 | —H | (morpholine structure) |

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, of a compound of the formula (I) depending on the condition being treated, the route of administration and the age, weight and condition of the patient. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt ard/or an absorption agent such as bentonite, kaolin or dicalcium phosphate. The powder mixture can be granulated by wetting with a binder, such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiological functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For treatments of the eye or other external tissues, for example mouth and skin, he formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in anti-cancer therapy, combination with other chemotherapeutic, hormonal or antibody agents is envisaged as well as combination with surgical therapy and radiotherapy. Combination therapies according to the present invention thus comprise the administration of at least one compound of formula (I) or a pharmaceutically acceptable salt or solvate thereof, or a physiologically functional derivative thereof, and the use of at least one other cancer treatment method. Preferably, combination therapies according to the present invention comprise the administration of at least one compound of formula (I) or a pharmaceutically acceptable salt or solvate thereof, or a physiologically functional derivative thereof, and at least one other pharmaceutically active agent, preferably an anti-neoplastic agent. The compound(s) of formula (I) and the other pharmaceutically active agent(s) may be administered together or separately and, when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of the Formula (I) or salts, solvates, or physiologically functional derivatives thereof and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I) or (II) or salts, solvates, or physiologically functional derivatives thereof with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may induce anti-neoplastic effects in a cell-cycle specific manner, i.e., are phase specific and, act at a specific phase of the cell cycle, or bind DNA and act in a non cell-cycle specific manner, i.e., are non-cell cycle specific and operate by other mechanisms.

Anti-neoplastic agents useful in combination with the compounds and salts, solvates or physiologically functional derivatives thereof of formula I include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine and thioguanine; and camptothecins such as 9-amino camptothecin, topotecan, irinotecan, CPT-11 and the various optical forms of 7-(4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumour antibiotics such as doxorubicin, daunomycin, epirubicin, idarubicin, mitomycin-C, dacttinomycin and mithramycin; and platinum coordination complexes such as cisplatin, carboplatin, and oxaliplatin; and (3) other chemotherapeutic agents including, but not limited to, anti-estrogens such as tamoxifen, toremifene, raloxifene, droloxifene and iodoxyfene; progerstrogens such as megestrol acetate; aromatase inhibitors such as anastrozole, letrazole, vorazole, and exemestane; antiandrogens such as flutamide, nilutamide, bicalutamide, and cyproterone acetate; LHRH agonists and antagagonists such as goserelin acetate and luprolide, testosterone 5α-dihydroreductase inhibitors such as finasteride; metalloproteinase inhibitors such as marimastat; antiprogestogens; urokinase plasminogen activator receptor function inhibitors; cyclooxygenase type 2 (COX-2) inhibitors such as celecoxib; angiogenic inhibiting agents such as VEGFR inhibitors and TIE-2 inhibitors; growth factor function inhibitors such as inhibitors of the functions of hepatocyte growth factor; erb-B2, erb-B4, epidermal growth factor recentor (EGFr), platelet derived growth factor receptor (PDGFr), vascular endothelial growth factor receptor (VEGFR) and TIE-2; and other tyrosine kinase inhibitors such as cyclin dependent inhibitors such as CDK2 and CDK4 inhibitors other than those described in the present invention.

In another embodiment, therapeutically effective amounts of the compounds of formula I or salts, solvates or physiologically derived derivatives thereof and agents which inhibit growth factor receptor function may be administered in combination to a mammal for treatment of a disorder mediated by inappropriate CDK activity, for instance in the treatment of cancer. Such growth factor receptors include, for example, EGFr, PDGFr, erb-B2, VEGFr, or TIE-2. Growth factor receptors and agents that inhibit growth factor receptor function are described, for instance, in Kath, John C., Exp. Opin. Ther. Patents (2000) 10(6):803-818 and in Shawver et al DDT Vol 2, No. 2 February 1997.

In one aspect of the present invention, there is provided a method of preventing or reducing the severity of epithelial cytotoxicity in a patient receiving cytotoxic therapy, comprising administering to said patient a therapeutically effective amount of a compound of formula (I) or a salt, solvate, or physiologically functional derivative thereof.

In one aspect of the present invention, there is provided a method of treating cancer in a mammal, including administering to said mammal therapeutically effective amounts of (i) a compound of formula (I), or salt, solvate or physiologically functional derivative thereof and (ii) at least one additional anti-cancer therapy. In one embodiment, the anti-cancer therapy is cytotoxic.

The compounds of formula (I) and salts, solvates and physiological functional derivatives thereof, are believed to have anticancer activity as a result of inhibition of the protein kinase CDK2 and/or CDK4 and its effect on selected cell lines whose growth is dependent on CDK2 and/or CDK4 kinase activity.

The present invention thus also provides compounds of formula (I) and pharmaceutically acceptable salts or solvates thereof, or physiologically functional derivatives thereof, for use in medical therapy, and particularly in the treatment of disorders mediated by inappropriate CDK activity.

The inappropriate CDK activity referred to herein is any CDK activity, that deviates from the normal CDK activity expected in a particular mammalian subject. Inappropriate CDK activity may take the form of, for instance, an abnormal increase in activity; or an aberration in the timing and or control of CDK activity. Such inappropriate activity may result then, for example, from overexpression or mutation of the protein kinase or ligand leading to inappropriate or uncontrolled activation of the receptor. Furthermore, it is also understood that unwanted CDK activity may reside in an abnormal source, such as a malignancy. That is, the level of CDK activity does not have to be abnormal to be considered inappropriate, rather the activity derives from an abnormal source.

The present invention is directed to methods of regulating, modulating, or inhibiting CDK2 and/or CDK4 for the prevention and/or treatment of disorders related to unregulated CDK activity. In particular, the compounds of the present invention can also be used in the treatment of certain forms of cancer. Furthermore, the compounds of the present invention can be used to provide additive or synergistic effects with certain existing cancer chemotherapies and radiation, and/or be used to provide protection from the epithelial cytotoxic effects of certain existing cancer chemotherapies and radiation.

A further aspect of the invention provides a method of treatment of a mammal suffering from a disorder mediated by inappropriate CDK activity, including susceptible malignancies, which includes administering to said subject an effective amount of a compound of formula (I) or a pharmaceutically acceptable salt, solvate, or a physiologically functional derivative thereof. In a preferred embodiment, the disorder is cancer. In one embodiment the CDK is CDK2. In another embodiment, the CDK is CDK4. In another embodiment, the CDK is CDK2 and CDK4.

A further aspect of the invention provides a method of treatment of a mammal suffering from cancer, which includes administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by inappropriate CDK activity. In a preferred embodiment, the disorder is cancer. In one embodiment the CDK is CDK2. In another embodiment, the CDK is CDK4. In another embodiment, the CDK is CDK2 and CDK4.

A further aspect of the present invention provides the use of a compound of formula (I), or a pharmaceutically acceptable salt or solvate thereof, or a physiologically functional derivative thereof, in the preparation of a medicament for the treatment of cancer and malignant tumours.

The mammal requiring treatment with a compound of the present invention is typically a human being.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

Compounds of general formula (I) may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (T. W. Green and P. G. M. Wuts (1991) *Protecting Groups in Organic Synthesis*, John Wiley Et Sons). These groups are removed at a convenient stage of the compound synthesis using methods that are readily apparent to those skilled in the art. The selection of processes as well as the reaction conditions and order of their execution shall be consistent with the preparation of compounds of Formula (I). Those skilled in the art will recognize if a stereocenter exists in compounds of Formula (I). Accordingly, the present invention includes both possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L Elied, S. H. Wilen, and L N. Mander (Wiley-Interscience, 1994).

A general method for preparing compounds of the general formula (I) involves the reaction of a compound of general formula (A) with a compound of general formula (B). Formula (A) and formula (B) are depicted in Scheme 1.

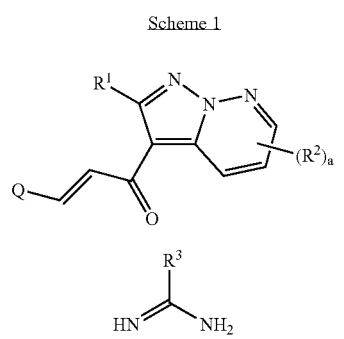

Q is alkyloxy, alkylthio or dialkylamino and integer a, and groups $R^1$, $R^2$, and $R^3$ are as defined above.

The general method can be readily carried out by mixing a compound of general formula (A) with a compound of general formula (B) in a suitable solvent, optionally in the presence of a base, and heating the reaction mixture to about 50-200° C. Typically the solvent is a lower alcohol such as methanol, ethanol, isopropanol, 2-butoxyethanol and the like, and the base can be, for example, a sodium alkoxide, potassium carbonate or an amine base such as triethylamine.

As shown in Scheme 2, compounds of general formula (A) may be conveniently prepared by reacting a compound of general formula (C) with a dimethylformamide dialkylacetal, to give compounds of formula (A) wherein Q is $Me_2N$, or with a trialkyl orthoformate or a dialkoxymethyl acetate, to give compounds of formula (A) wherein Q is an alkoxy group. Conveniently, the dimethylformamide dialkylacetal is dimethylformamide dimethyl acetal or dimethylformamide di-tert-butyl acetal and the reaction is carried out by mixing the compound of general formula (C) with the dimethylformamide dialkylacetal and optionally heating the reaction. Preferred trialkyl orthoformates include trimethyl orthoformate and triethyl orthoformate. In a similar manner, diethoxymethyl acetate can be employed to prepare compounds of general formula (A) wherein Q is EtO—. Integer a and groups $R^1$ and $R^2$ are as defined above.

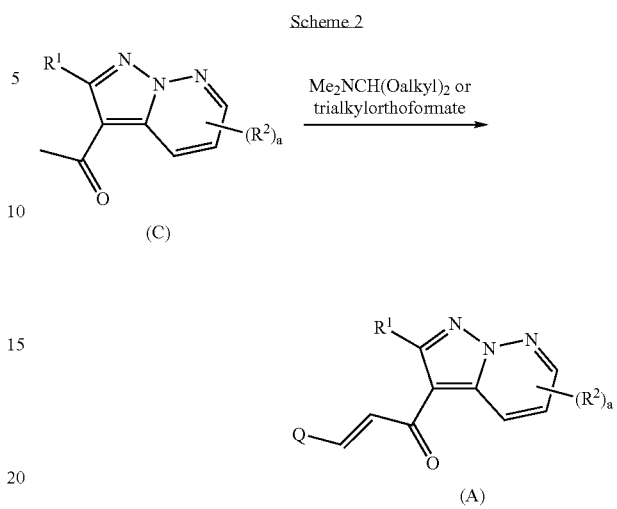

Compounds of general formula (C) can be prepared according to Scheme 3 from compounds of general formula (D) and general formula (E) by a cycloaddition procedure. Typically the cycloaddition procedure is carried out by combining compounds of general formula (D) with compounds of general formula (E) in a suitable solvent and treating the mixture with a base. Optionally the reaction can be heated. Preferably the solvent is dichloromethane, chloroform, acetonitrile, diethyl ether and the like, and the base is an amine such as triethylamine, diisopropylethylamine or diazabicycloundecene (DBU). In another preferred method, compounds of general formula (D) and (E) are combined in a mixture of solvents and treated with a base. Preferably the solvent mixtures are DMSO and water or methanol and water, and the base is sodium hydroxide or potassium hydroxide. The groups $R^1$ and $R^2$, and integer a are as defined above.

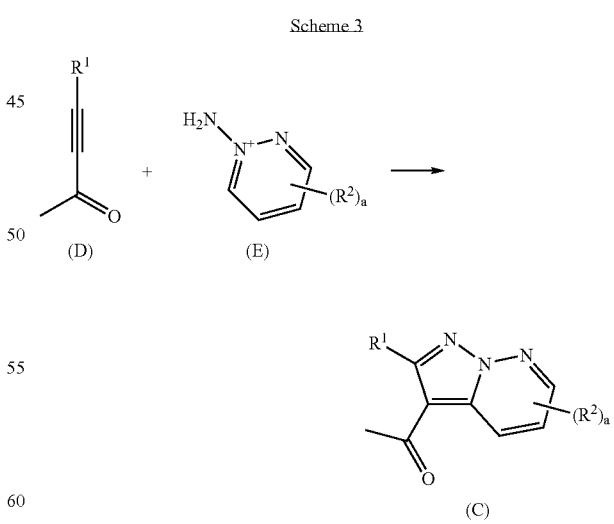

Compounds of general formula (D) are known in the literature and can be prepared as shown in Scheme 4 by oxidation of alcohols of general formula (F) under conditions typically employed for the oxidation of propargylic alcohols. Group $R^1$ is as defined above.

Scheme 4

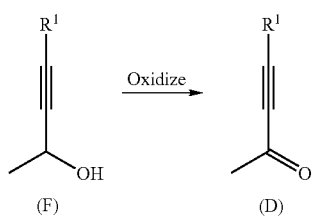

Alternatively, compounds of general formula (D) can be prepared according to Scheme 5 by reaction of an ethyne of general formula (G) with a suitable base to form the ethynyl anion and treatment of said anion with dimethyl acetamide. Preferably the base is an alkyl lithium, such as n-butyl lithium, or a lithium dialkylamide, such as lithium diisopropylamide (LDA). $R^1$ is as defined above.

Scheme 5

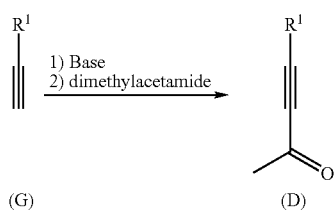

As shown in Scheme 6, compounds of general formula (E) are N-aminopyridazines and are conveniently prepared by treatment of a pyridazine of general formula (H) with an aminating reagent. Conveniently the aminating reagent is O-mesitylenesulfonylhydroxylamine (MSH) or hydroxylamine-O-sulfonic acid (HOSA). Preferably the aminating agent is hydroxylamine-o-sulfonic acid in water with the addition of a buffer to control the pH of the reaction medium. Integer a and $R^2$ are as defined above.

Scheme 6

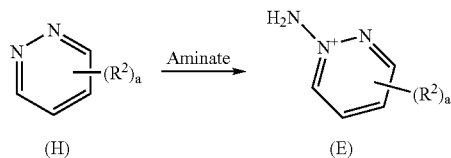

As shown in Scheme 7, compounds of general formula (I) can be converted to alternate compounds of general formula (I). For example, compounds of general formula (J), wherein an $R^2$ group is a methoxy (OMe) substituent and is located at position 6, using the numbering system described below, can be converted to compounds of general formula (K) wherein an $R^2$ is a hydroxyl group at position 6. Said conversion can be carried out by treatment of a compound of general formula (J) with an acid or a base in a suitable solvent and optionally heating the mixture. Preferably the base is an amine such as morpholine. Preferably the acid is aqueous hydrogen iodide. Integer a, and groups $R^1$, $R^2$, and $R^3$ are as defined above.

Scheme 7

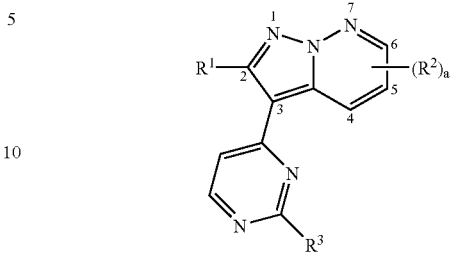

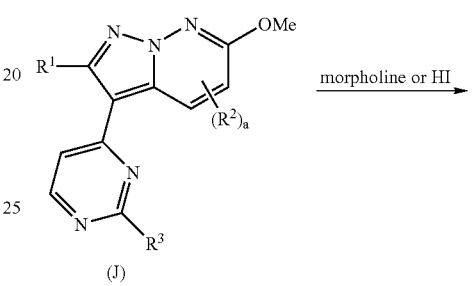

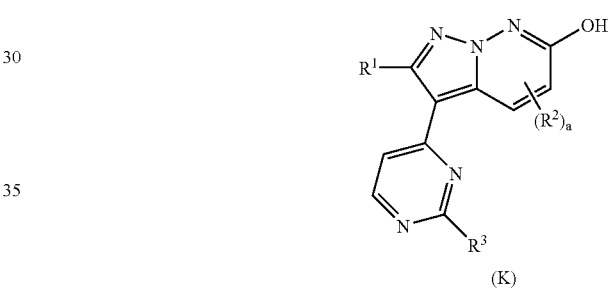

The alcohol function in compounds of general formula (K) can be further transformed according to Scheme 8 by treatment with, for example, trifluoromethanesulfonic anhydride or N-phenyltrifluoromethylsulfonimide to afford a triflate. Said triflates are known in the literature as leaving groups and can be readily displaced by treatment with an amine in a suitable solvent to give compounds of general formula (L). Integer a, and groups $R^1$, $R^2$, $R^3$, $R^4$, and $R^5$ are as defined above.

Scheme 8

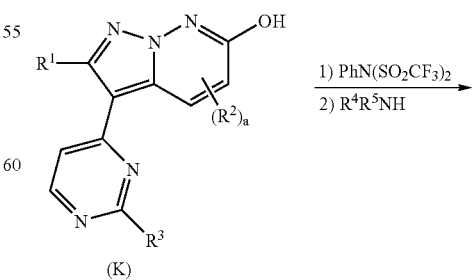

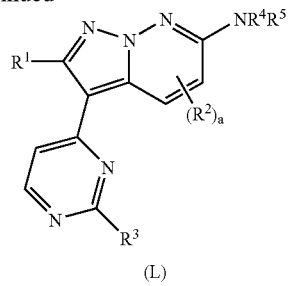

(L)

Compounds of general formula (C) are similarly converted to alternate compounds of general formula (C).

In Scheme 9, compounds of general formula (M) in which an $R^2$ group is a methoxy substituent, and is located at position 6, can be converted to the corresponding hydroxy compound, of general formula (N), by treatment with an amine such as morpholine or an acid such as aqueous hydrogen iodide. Said hydroxy derivatives of general formula (N) can be converted to triflates, of general formula (O), by treatment with a trifluoromethanesulfonylating agent such as trifluoromethanesulfonic anhydride or N-phenyltrifluoromethanesulfonimide. Triflates of general formula (O) can be converted to amino, thio or ether derivatives by treatment with amines, thiols or alcohols respectively, optionally in the presence of a metal catalyst. Alternatively, triflates such as those of general formula (O) can be reacted with a transition metal catalyst and a coupling partner to give compounds of general formula (P). Preferably the transition metal catalyst is a palladium or nickel complex. More preferably the catalyst is a palladium complex such as tetrakis(triphenylphosphine)palladium(0). Coupling partners can be derivatives of tin, boron, zinc, aluminum, copper, magnesium, zirconium, and the like. Preferred coupling partners include triaklyltin derivatives or boron containing derivatives. Such reactions are well documented in the literature and are commonly referred to as Stille couplings and Suzuki couplings respectively. Under said conditions, triflates such as those of general formula (O) can be converted to compounds of general formula (P) wherein the group A can represent an aryl, heteroaryl, ethenyl, ethynyl and the like. It will be appreciated by one skilled in the art that the aryl, heteroaryl, ethenyl, or ethynyl group can be suitably substituted. Integer a, and groups $R^1$ and $R^2$ are as defined above.

Scheme 9

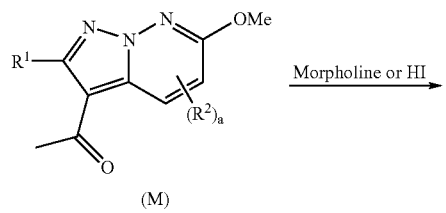

(M)

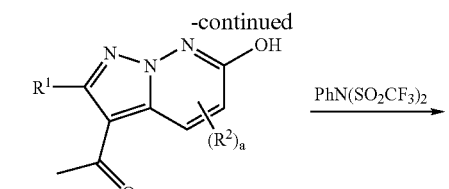

(N)

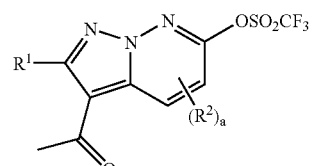

(O)

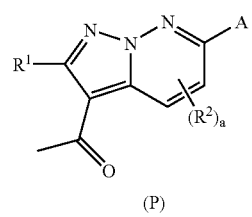

(P)

As shown in Scheme 10, another method for the conversion of compounds of general formula (I) to alternative compounds of formula (I), compounds of general formula (Q), wherein $R^3$ is an alkylthio group, which can be reacted with an amine in a suitable solvent and optionally heated to give compounds of general formula (R). Preferred solvent for effecting the reaction include lower alcohols, such as methanol, ethanol and isopropanol. Even more preferably the reaction is heated to about 150° C. in a sealed vessel.

A still more preferred method involves the oxidation of compounds of general formula (R) to the corresponding sulfoxide (S) or sulfone (T), followed by reaction with an amine in a suitable solvent with optional heating. Preferred methods for effecting said oxidation involve the use of reagents typically employed for the oxidation of sulfur compounds such as hydrogen peroxide or m-chloroperoxybenzoic acid in an inert solvent such as dichloromethane, acetonitrile and the like. Preferred solvent for effecting the reaction with an amine include lower alcohols, such as methanol, ethanol and isopropanol. Even more preferably the reaction is heated to about 150° C. in a sealed vessel. Integer a and groups $R^1$, $R^2$, $R^5$, and $R^7$ are as defined above.

Scheme 10

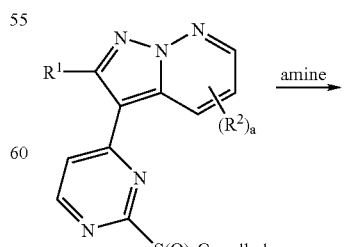

n = 0, (Q)
n = 1, (S)
n = 2, (T)

-continued

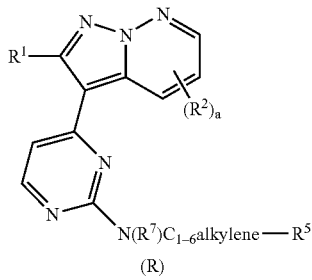

As shown in Scheme 11, compounds of general formula (Q) can be conveniently prepared by treating a mixture of compounds of general formula (U) and compounds of general formula (E) in a suitable solvent with a base and optionally heating the reaction mixture. Preferably the solvent is a halogenated solvent, such as dichloromethane, and the base is an amine, such as triethylamine, diazabicycloundecene (DBU) and the like, or an alkali metal hydroxide, such as sodium hydroxide or potassium hydroxide. Integer a and groups $R^1$ and $R^2$ are as defined above.

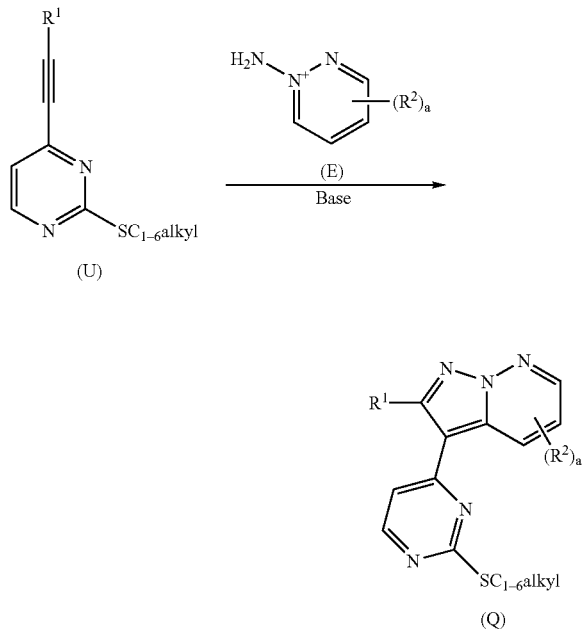

As shown in Scheme 12, compounds of general formula (U) can be conveniently prepared by treating a compound of general formula (V), wherein B is a halogen such as iodide, bromide or chloride, or a triflate, with an ethyne of general formula (G) in a suitable solvent in the presence of a palladium catalyst and optionally heating the reaction mixture. Preferably B is iodide and the palladium catalyst is tetrakis(triphenylphosphine)palladium(0), dichlorobis(triphenylphosphine)palladium(II), and the like. Preferred solvents include dichloromethane, tetrahydrofuran and the like. Compounds of general formula (V) are known in the literature.

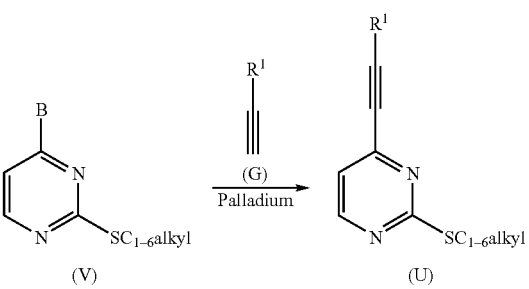

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society or the Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| i.v. (intravenous); | Hz (Hertz); |
| MHz (megahertz); | mol (moles); |
| mmol (millimoles); | RT (room temperature); |
| min (minutes); | h (hours); |
| mp (melting point); | TLC (thin layer chromatography); |
| $T_r$ (retention time); | RP (reverse phase); |
| MeOH (methanol); | I-PrOH (isopropanol); |
| TEA (triethylamine); | TFA (trifluoroacetic acid); |
| TFAA (trifluoroacetic anhydride); | THF (tetrahydrofuran); |
| DMSO (dimethylsulfoxide); | EtOAc (ethyl acetate); |
| DME (1,2-dimethoxyethane); | DCM (dichloromethane); |
| DCE (dichloroethane); | DMF (N,N-dimethylformamide); |
| DMPU (N,N'-dimethylpropyleneurea); | (CDI (1,1-carbonyldiimidazole); |
| IBCF (isobutyl chloroformate); | |
| HOSu (N-hydroxysuccinimide); | HOAc (acetic acid); |
| mCPBA (meta-chloroperbenzoic acid; | HOBT (1-hydroxybenzotriazole); EDC |
| BOC (tert-butyloxycarbonyl); | (ethylcarbodiimide hydrochloride); FMOC (9-fluorenylmethoxycarbonyl); |
| DCC (dicyclohexylcarbodiimide); | CBZ (benzyloxycarbonyl); |
| Ac (acetyl); | atm (atmosphere); |
| TMSE (2-(trimethylsilyl)ethyl); | TMS (trimethylsilyl); |
| TIPS (triisopropylsilyl); | TBS (t-butyldimethylsilyl); |
| DMAP (4-dimethylaminopyridine); | Me (methyl); |
| HPLC (high pressure liquid chromatography); | |
| BOP (bis(2-oxo-3-oxazolidinyl)phosphinic chloride); | |
| TBAF (tetra-n-butylammonium fluoride); | |

-continued

Et (ethyl);
HOSA (hydroxylamine sulfonic acid);
DIEA (diisopropylethylamine).
tBu (tert-butyl);
DEAD (diethylazodicarboxylate);

All references to ether are to diethyl ether; brine refers to a saturated aqueous solution of NaCl. Unless otherwise indicated, all temperatures are expressed in ° C. (degrees Centigrade). All reactions conducted under an inert atmosphere at room temperature unless otherwise noted.

$^1$H NMR spectra were recorded on a Varian VXR-300, a Varian Unity-300, a Varian Unity-400 instrument, or a General Electric QE-300. Chemical shifts are expressed in parts per million (ppm, δ units)) relative to Me$_4$Si. Coupling constants are in units of hertz (Hz). Splitting patterns describe apparent multiplicities and are designated as s (singlet), d (doublet), t (triplet), q (quartet), m (multiplet), br (broad).

Low-resolution mass spectra (MS) were recorded via LCMS on a Micromass ZQ, ZMD, or QuattroMicro spectrometer; high resolution MS were obtained using a JOEL SX-102A spectrometer. All mass spectra were taken under electrospray ionization (ESI), chemical ionization (CI), electron impact (EI), atmospheric pressure chemical ionization (APCI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid or p-anisaldehyde solution. Flash column chromatography was performed on silica gel (230-400 mesh, Merck). Optical rotations were obtained using a Perkin Elmer Model 241 Polarimeter. Melting points were determined using a Mel-Temp II apparatus and are uncorrected.

The following examples describe the syntheses of intermediates particularly useful in the synthesis of compounds of Formula (I), (II), and (III):

Example 1

N-Cyclopropyl-4-pyrazolo[1,5-b]pyridazin-3-yl-2-pyrimidinamine

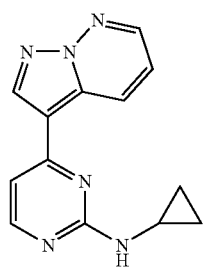

a) To a solution of (2E)-3-(dimethylamino)-1-pyrazolo[1,5-b]pyridazin-3-yl-2-propen-1-one (43 mg, 0.20 mmol) in DMF (2 mL) was added N-cyclopropylguanidine.0.5H$_2$SO$_4$ (160 mg, 0.80 mmol) and potassium carbonate (110 mg, 0.80 mmol). The reaction was heated at an oil bath temperature of 165° C. for about 18 hours. The mixture was cooled to RT and the solvent was removed in vacuo. The residue was dissolved in chloroform and filtered. The filtrate was purified by flash column chromatography (0-10% gradient MeOH/CH$_2$Cl$_2$) to give the title compound as a yellow solid (38 mg, 75%). $^1$H-NMR (400 MHz, d$^6$-DMSO) δ 9.13 (dd, 1H, J=9.0, 1.6 Hz), 8.77 (s, 1H), 8.53 (dd, 1H, J=4.4, 1.6 Hz), 8.24 (d, 1H, J=5.2 Hz), 7.38 (m, 1H), 7.10 (d, 1H, J=5.2 Hz), 2.72 (m, 1H), 0.71 (m, 2H), 0.47 (m, 2H), MS (ESI) (M+H)$^+$ 253.

b) (2E)-3-(Dimethylamino)-1-pyrazolo[1,5-b]pyridazin-3-yl-2-propen-1-one. To a solution of 1-pyrazolo[1,5-b]pyridazin-3-ylethanone (8.5 g, 52.7 mmol) in DMF (100 mL) was added dimethylformamide di-tert-butylacetal (16.1 g, 79.2 mmol). The reaction was heated at an oil bath temperature of 100° C. for about 4 hours. The solvent was removed in vacuo. The residue was triturated with diethylether to give the title compound as a brown solid (8 g, 70%). $^1$H-NMR (300 MHz, d$^6$-DMSO) δ 8.76 (dd, 1H, J=10.0, 2.0 Hz), 8.74 (s, 1H), 8.61 (dd, 1H, J=4.0, 2.0 Hz), 7.74 (d, 1H, J=12 Hz), 7.44 (dd, 1H, J=10.0, 4.0 Hz), 5.87 (d, 1H, J=12 Hz), 3.18 (bs, 3H), 2.97 (bs, 3H); MS (ESI) (M+H)$^+$ 217.

c) 1-Pyrazolo[1,5-b]pyridazin-3-ylethanone. To a slurry of 1-aminopyridazinium iodide (16 g, 72 mmol) in CH$_2$Cl$_2$ (200 mL) was added 3-butyne-2-one (2.4 g, 36 mmol). The reaction flask was cooled in an ice bath at 4° C. and a solution of KOH (5.0 g, 89 mmol) in water (100 mL) was added in one portion. The mixture was stirred at RT for about 4 hours. The organic layer was separated and the aqueous layer was extracted with CH$_2$Cl$_2$ (2×200 mL). The combined organic layers were dried (MgSO$_4$), filtered and concentrated in vacuo. The residue was triturated with diethyl ether to give the title compound as a red solid (4.0 g, 69%). $^1$H-NMR (300 MHz, CDCl$_3$) δ 8.78 (dd, 1H, J=9.0, 2.0 Hz), 8.51 (dd, 1H, J=4.4, 2.0 Hz), 8.47 (s, 1H), 7.35 (dd, 1H, J=9.0, 4.4 Hz), 2.63 (s, 3H); MS (ESI) (M+H)$^+$ 162.

d) 1-Aminopyridazinium iodide. Hydroxylamine-O-sulfonic acid (13.1 g, 115 mmol) was dissolved in water (25 mL) and the reaction flask was cooled in an icebath at 10° C. Aqueous KHCO$_3$ (48 mL, 2.4 M) was added until the solution was at pH 5.0. Pyridazine (6.2 g, 77 mmol) was added in one portion and the flask was heated to 70° C. for about 1 hour. The pH was adjusted to 7.0 by the addition of aqueous KHCO$_3$ (approx. 10 mL, 2.4M). The reaction was cooled to 40° C. and the mixture was allowed to stir for about 1 hour. Potassium iodide (12.8 g, 77 mmol) in water (25 mL) was added. The solvent was removed in vacuo followed by the addition of 5% methanol in ethanol (100 mL). The solids were collected by filtration and dried in vacuo to give the title compound as a yellow solid (10.5 g, 61%). $^1$H-NMR (300 MHz, d$^6$-DMSO) δ 8.85 (bs, 2H), 9.27 (d, 1H, J=5.2 Hz), 9.12 (d, 1H, J=6.3 Hz), 8.49 (ddd, 1H, J=8.1, 6.3, 2.1 Hz), 8.14 (dd, 1H, J=8.1, 5.2 Hz).

e) N-Cyclopropylguanidine.0.5H$_2$SO$_4$. To a solution of O-methylisourea hydrogensulfate (50.0 g, 290 mmol) in water (150 mL) was added cyclopropyl amine (33.0 g, 581 mmol). The mixture was heated at an oil bath temperature of 100° C. for about 14 hours. The water was removed in vacuo. Ethanol (150 mL) was added and the solids isolated by filtration. The solids were dried under vacuum (1 torr) for about 18 hours to give the title compound as a white powder (47.6 g, 42%). $^1$H-NMR (300 MHz, d$^6$-DMSO) δ 2.0 (m, 1H), 0.20 (m, 2H), 0.10 (m, 2H).

Example 2

N-Cyclopropyl-N-methyl-4-pyrazolo[1,5-b]pyridazin-3-yl-2-pyrimidinamine

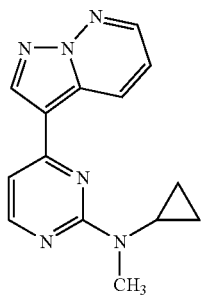

a). To a solution of N-cyclopropyl-4-pyrazolo[1,5-b]pyridazin-3-yl-2-pyrimidinamine (25 mg, 0.1 mmol) in DMF (2 mL) was added sodium hydride (6 mg, 0.25 mmol) and methyl iodide (0.013 mL, 0.15 mmol). The reaction was allowed to stir for about 1 hour. The reaction was concentrated in vacuo. Water (10 mL) was added and the aqueous layer was extracted with EtOAc (2×30 mL). The combined organic layers were dried (MgSO$_4$) filtered and concentrated in vacuo. The residue was triturated with diethylether to give the title compound as light orange solid (20 mg, 80%). $^1$H-NMR (400 MHz, CDCl$_3$) δ 9.07 (d, 1H, J=8.8 Hz), 8.46 (s, 1H), 8.35 (m, 2H) 7.12 (dd, 1H, J=8.8, 4.4 Hz), 6.89 (d, 1H, J=5.6 Hz), 3.23 (s, 3H), 2.85 (m, 1H), 0.94 (m, 2H), 0.73 (m, 2H); MS (ESI) (M+H)$^+$ 267.

Example 3

4-Pyrazolo[1,5-b]pyridazin-3-yl-N-(2,2,2-trifluoroethyl)-2-pyrimidinamine

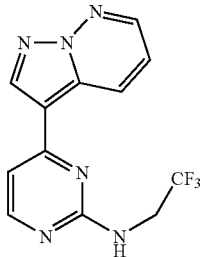

a) In a similar manner as described in Example 1a, from N-2,2,2-trifluoroethylguanidine.0.5H$_2$SO$_4$ was obtained the title compound as a yellow solid. $^1$H-NMR (400 MHz, d$^6$-DMSO) δ 8.81 (s, 1H), 8.54 (dd, 1H, J=4.4, 2.0 Hz), 8.31 (d, 1H, J=5.6 Hz), 7.80 (bm, 1H), 7.40 (dd, 1H, J=8.8, 4.4 Hz), 7.21 (d, 1H, J=4.4 Hz), 4.17 (m, 2H); MS (APCI) (M+H)$^+$ 295.

b) N-(2,2,2-Trifluoroethyl)guanidine.0.5H$_2$SO$_4$. In a similar manner as described in Example 1e, from 2,2,2-trifluroethyl amine was obtained the title compound (Tetrahedron Lett (1993), 34-(21), 3389) as a brown solid.

Example 4

N-Phenyl-4-pyrazolo[1,5-b]pyridazin-3-yl-2-pyrimidinamine

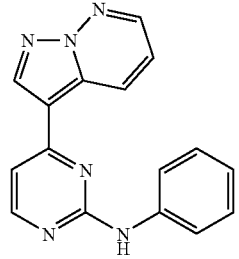

a) In a similar manner as described in Example 1a, from phenylguanidine.HNO$_3$ was obtained the title compound as a brown solid. $^1$H-NMR (300 MHz, d$^6$-DMSO) δ 9.61 (s, 1H), 9.2 (d. 1He J=9.0 Hz), 8.93 (s, 1H), 8.63 (d, 1H, J=2.9 Hz), 8.50 (d, 1H, J=5.2 Hz), 7.78 (d, 2H, J=8.1 Hz), 7.49 (dd, 1H, J=9.0, 4.1 Hz), 7.37 (m, 3H), 7.02 (t, 1H, J=7.3 Hz); MS (ESI) (M+H)$^+$ 289.

Example 5

N-(4-Chlorophenyl)pyrazolo[1,5-b]pyridazin-3-yl-2-pyrimidinamine

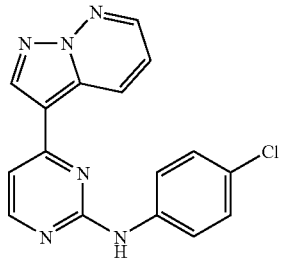

a) In a similar manner as described in Example 1a, from N-(4-chlorophenyl)guanidine.HNO$_3$ was obtained the title compound as a brown solid. $^1$H-NMR (300 MHz, d$^6$-DMSO) δ 9.76 (s, 1H), 9.19 (d, 1H, J=8.8 Hz), 8.94 (s, 1H), 8.64 (d, 1H, J=2.8 Hz), 8.51 (d, 1H, J=8.8 Hz), 7.84 (d, 2H, J=8.8 Hz), 7.53 (dd, 1H, J=9.2, 4.5 Hz), 7.42 (m, 3H); MS (ESI) (M+H)$^+$ 323.

Example 6

N-0Fluorophenyl)pyrazolo[1,5-b]pyridazin-3-yl-2-pyrimidinamine a) In a similar manner as described in Example 1a, from N-(4-fluorophenyl)guanidine.HNO$_3$ was obtained the title compound as a yellow solid. $^1$H-NMR (300 MHz, d6-DMSO) δ 9.63 (s, 1H), 9.15 (d, 1H, J=8.7 Hz), 8.92 (s, 1H), 8.64 (dd, 1H, J=4.5, 1.8 Hz), 8.48 (d, 1H, J=5.3 Hz), 7.78 (dd, 2H, J=9.0, 5.0 Hz), 7.50 (dd, 1H, J=9.1, 4.6 Hz), 7.40 (d, 1H, J=5.3 Hz), 7.21 (t, 2H, J=8.9 Hz); MS (ESI) (M+H)+ 307.

Example 7

3-[(4-Pyrazolo[1,5-b]pyridazin-3-yl-2-pyrimidinyl)amino]benzonitrile

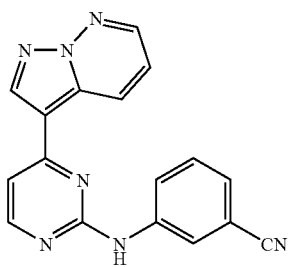

a) In a similar manner as described in Example 1a, from N-(3-cyanophenyl)guanidine.HNO3 was obtained the title compound as a yellow solid. 1H-NMR (300 MHz, d6-DMSO) δ 9.99 (s, 1H), 9.17 (d, 1H, J=9.0 Hz), 8.96 (s, 1H), 8.66 (dd, 1H, J=4.4, 1.6 Hz), 8.58 (d, 1H, J=5.3 Hz), 8.41 (s, 1H), 7.97 (d, 1H, J=8.2 Hz); 7.60-7.44 (m, 4H); MS (APCI) (M+H)+ 314.

b) N-((3-Cyanophenyl)guanidine.HNO3. To a solution of 3-aminobenzonitrile (3.31 g, 28 mmol) in ETOH (28 mL) was added cyanamide (2.5 mL of a 50% w/w solution in water). HNO3 (1.98 mL, 14.2 M) is added dropwise. The mixture was heated at an oil bath temperature of 100° C. for about 3 hours. The flask was allowed to cool to RT. Et2O (20 mL) was added and the solids isolated by filtration. The solids were dried under vacuum (1 torr) for about 18 hours to give the title compound as a beige powder (2.9 g, 46%). 1H-NMR (300 MHz, d6-DMSO) δ 9.80 (s, 1H), 7.77 (m, 2H), 7.69-7.57 (m, 6H); MS (ESI) (M+H)+ 161.

Example 8

4-[(4-Pyrazolo[1,5-b]pyridazin-3-yl-2-pyrimidinyl)amino]benzoic Acid

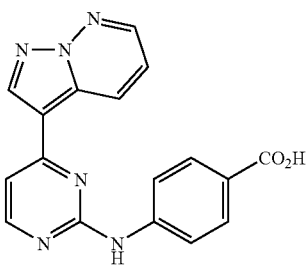

a) In a similar manner as described in Example 1a, 4-{[amino(imino)methyl]amino}benzoic acid.HCl was obtained the title compound as a yellow solid. 1H-NMR (300 MHz, d6-DMSO) δ 9.99 (s, 1H), 9.25 (d, 1H, J=9.0 Hz), 8.96 (s, 1H), 8.65 (dd, 1H, J=4.5, 2.6 Hz), 8.57 (d, 1H, J=5.2 Hz), 7.93 (m, 4H), 7.53 (dd, 1H, J=8.9, 4.4 Hz), 7.50 (d, 1H, J=5.5 Hz); MS (APCI) (M+H)+ 333.

Example 9

4-Pyrazolo[1,5-b]pyridazin-3-yl-N-[3-(trifluoromethyl)phenyl]-2-pyrimidinamine

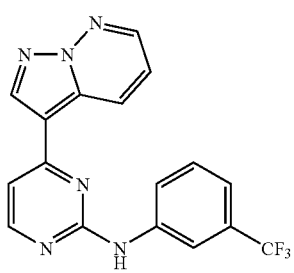

a) In a similar manner as described in Example 1a, from N-[3-(trifluoromethyl)phenyl]guanidine was obtained the title compound as a brown solid. 1H-NMR (300 MHz, d6-DMSO) δ 9.98 (s, 1H), 9.17 (d, 1H, J=8.9 Hz), 8.95 (s, 1H), 8.65 (bs, 1H), 8.57 (d, 1H, J=5.4 Hz), 8.32 (bs, 1H), 8.00 (d, 1H, J=8.1 Hz), 7.59 (t, 1H, J=8.0 Hz), 7.48 (m, 2H), 7.34 (d, 1H, J=8.1 Hz); MS (ESI) (M+H)+ 357.

Example 10

N-(3-Nitrophenyl)-4-pyrazolo[1,5-b]pyridazin-3-yl-2-pyrimidinamine

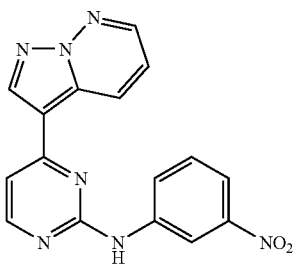

a) In a similar manner as described in Example 1a, from N-(3-nitrophenyl)guanidine was obtained the title compound as a brown solid. 1H-NMR (300 MHz, d6-DMSO) δ 10.15 (s, 1H), 9.18 (d, 1H, J=8.9 Hz), 8.97 (s, 1H), 8.93 (s, 1H), 8.66 (d, 1H, J=4.4 Hz), 8.60 (d, 1H, J=5.1 Hz), 8.11 (d, 1H, J=8.1 Hz), 7.85 (d, 1H, J=8.1 Hz), 7.64 (t, 1H, J=8.1 Hz), 7.50 (m, 2H); MS (ESI) (M+H)+ 357.

b) N-(3-Nitrophenyl)guanidine.HCl. In a similar manner as described in Example 1e, from 3-nitrophenyl aniline was obtained the title compound (Anal. Biochem. (1999), 276 (2), 251) as a brown solid.

Example 11

N-(2-Chlorophenyl)-4-pyrazolo[1,5-b]pyridazin-3-yl-2-pyrimidinamine

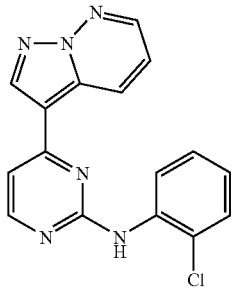

a) In a similar manner as described in Example 1a, from N-(2-chlorophenyl)guanidine was obtained the title compound as a brown solid. $^1$H-NMR (300 MHz, d$^6$-DMSO) δ 9.06 (s, 1H), 8.90 (s, 1H), 8.84 (d, 1H, J=9.0 Hz), 8.60 (bs, 1H), 8.44 (d, 1H, J=5.2 Hz), 7.81 (d, 1H, J=8.1 Hz), 7.59 (d, 1H, J=7.9 Hz), 7.39 (m, 3H), 7.26 (t, 1H, J=7.6 Hz); MS (ESI) (M+H)$^+$ 323.

b) N-(2-Chlorophenyl)guanidine.HCl. Prepared from 2-chlorophenyl aniline as described in (J. Med. Chem. (1996), 39(20), 4017).

Example 12

N-(4-Methoxyphenyl)-4-pyrazolo[1,5-b]pyridazin-3-yl-2-pyrimidinamine

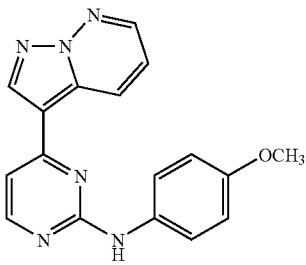

a) In a similar manner as described in Example 1a, from N-(4-methoxyphenyl)guanidine was obtained the title compound as a brown solid. $^1$H-NMR (300 MHz, d$^6$-DMSO) δ 9.41 (s, 1H), 9.15 (bs; 1H), 8.90 (s, 1H), 8.62 (d, 1H, J=2.6 Hz), 8.44 (d, 1H, J=5.3 Hz), 7.64 (d, 2H, J=8.9 Hz), 7.47 (dd, 1H, J=9.1, 4.5 Hz), 733 (d, 1H, J=5.2 Hz), 6.95 (d, 1H, J=8.9 Hz), 3.78 (s, 3H); MS (ESI) (M+H)$^+$ 319.

Example 13

4-Pyrazolo[1,5-b]pyridazin-3-yl-N-(3,4,5-trimethoxyphenyl)-2-pyrimidinamine

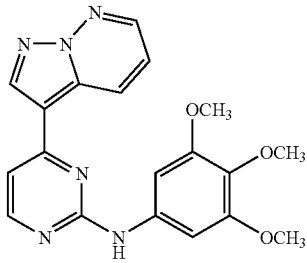

a) In a similar manner as described in Example 1a, from N-(3,4,5-trimethoxyphenyl)guanidine was obtained the title compound as a brown solid. $^1$H-NMR (300 MHz, d$^6$-DMSO) δ 9.50 (s, 1H), 9.21 (d, 1H, J=9.7 Hz), 8.92 (s, 1H), 8.63 (d, 1H, J=2.7 Hz), 8.50 (d, 1H, J=5.2 Hz), 7.47 (dd, 1H, J=9.1, 4.5 Hz), 7.38 (d, 1H, J=5.2, 4.5 Hz), 7.18 (s, 2H); MS (ESI) (M+H)$^+$ 379.

b) N-(3,4,5-Trimethoxyphenyl)guanidine.HNO$_3$. In a similar manner as described in Example 7b, from 3,4,5-trimethoxy aniline was obtained the title compound (J. Med. Chem. (1975), 18(11), 1077) as a brown solid.

Example 14

N-[3-(1,3-Oxazol-5-yl)phenyl]-4-pyrazolo[1,5-b]pyridazin-3-yl-2-pyrimidinamine

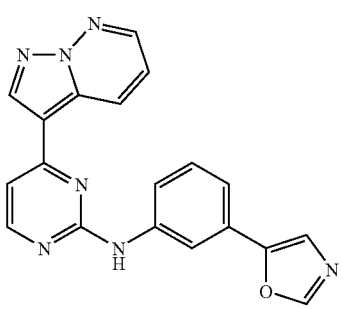

a) In a similar manner as described in Example 1a, from N-[3-(1,3-oxazol-5-yl)phenyl]guanidine was obtained the title compound as a brown solid. $^1$H-NMR (300 MHz, d$^6$-DMSO) δ 9.78 (s, 1H), 9.18 (d, 1H, J=8.9 Hz), 8.95 (s, 1H), 8.64 (d, 1H, J=3.1 Hz), 8.55 (d, 1H, J=5.2 Hz), 8.46 (s, 1H), 8.24 (s, 1H), 7.75 (d, 1H, J=7.9 Hz), 7.67 (s, 1H), 7.49-7.39 (m, 3H), 7.35 (dd, 1H, J=9.0, 4.5 Hz); MS (ESI) (M+H)$^+$ 356.

b) N[3-(1,3-Oxazol-5-yl)phenyl]guanidine.HNO$_3$. In a similar manner as described in Example 7b, from 3-(1,3-oxazol-5-yl)aniline was obtained the title compound as a brown solid. $^1$H-NMR (300 MHz, d$^6$-DMSO) δ 9.70 (s, 1H), 8.52 (s, 1H), 7.80 (s, 1H), 7.70-7.43 (m, 7H), 7.27 (d, 1H, J=7.9 Hz); MS (ESI) (M+H)$^+$ 203.

Example 15

N-(4-Pyrazolo[1,5-b]pyridazin-3-yl-2-pyrimidinyl)-1H-benzimidazol-6-amine

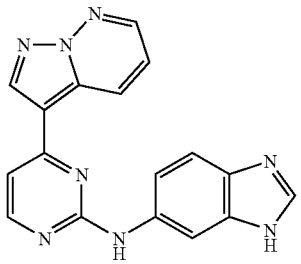

a) In a similar manner as described in Example 1a, from N-(1H-benzimidazol-6-yl)guanidine.HNO$_3$ was obtained the title compound as a brown solid. $^1$H-NMR (300 MHz, d$^6$-DMSO) δ 12.35 (bs, 1H), 9.59 (s, 1H), 9.21 (d, 1H, J=9.2 Hz), 8.93 (s, 1H), 8.64 (d, 1H, J=2.7 Hz), 8.50 (d, 1H, J=5.2 Hz), 8.18 (s, 1H), 8.16 (s, 1H), 7.58 (d, 1H, J=8.5 Hz), 7.45-7.41 (m, 2H), 7.37 (d, 1H, J=5.2 Hz); MS (ESI) (M+H)$^+$ 329.

b) N-(1H-Benzimidazol-6-yl)guanidine.HNO$_3$. In a similar manner as described in Example 7b, from 1H-benzimidazol-6-amine was obtained the title compound as a brown solid. $^1$H-NMR (400 MHz, d$^6$-DMSO) δ 9.76 (s, 1H), 9.40 (s, 1H), 7.85 (d, 1H, J=8.8 Hz), 7.69 (d, 1H, J=1.8 Hz), 7.42 (bs, 4H), 7.37 (dd, 1H, J=8.8, 1.8 Hz); MS (ESI) (M+H)$^+$ 176.

Example 16

N-(4Pyrazolo[1,5-b]pyridazin-3-yl-2-pyrimidinyl)-1,3-benzoxazol-2-amine

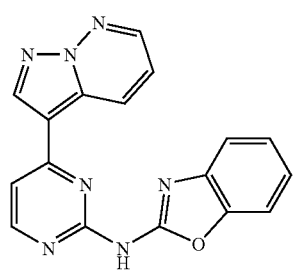

a) In a similar manner as described in Example 1a, from N(1,3-benzoxazol-2-yl)guanidine was obtained the title compound as a brown solid. $^1$H-NMR (300 MHz, d$^6$-DMSO) δ 11.68 (s, 1H), 10.23 (d, 1H, J=9.1 Hz), 9.02 (s, 1H), 8.68-8.65 (m, 2H), 7.73-7.62 (m, 4H), 7.38-7.25 (m, 2H); MS (ESI) (M+H)$^+$ 0.330.

Example 17

N-(6-Chloro-1H-benzimidazol-2-yl)-N-(4-pyrazolo[1,5-b]pyridazin-3-yl-2-pyrimidinyl)amine

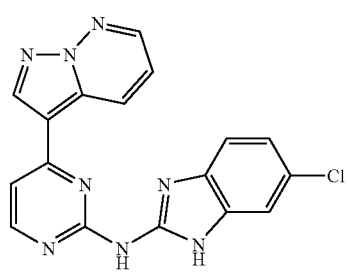

a) In a similar manner as described in Example 1a, from N-(6-Chloro-1H-benzimidazol-2-yl)guanidine was obtained the title compound as a brown solid. $^1$H-NMR (400 MHz, d$^6$-DMSO) δ 12.20 (s, 1H), 11.32 (s, 1H), 9.50 (d, 1H, J=8.0 Hz), 8.96 (s, 1H), 8.62 (dd, 1H, J=4.4, 1.8 Hz), 8.59 (d, 1H, J=5.5 Hz), 7.56 (d, $_1$H, J=5.5 Hz), 7.48 (dd, 1H, J=9.0, 4.4 Hz), 7.53 (m, 1H), 7.40 (m, 1H), 7.06 (m, 1H); MS (ESI) (M+H)$^+$ 363.

Example 18

N-(4-Chlorobenzyl)-pyrazolo[1,5-b]pyridazin-3-yl-2-pyrimidinamine

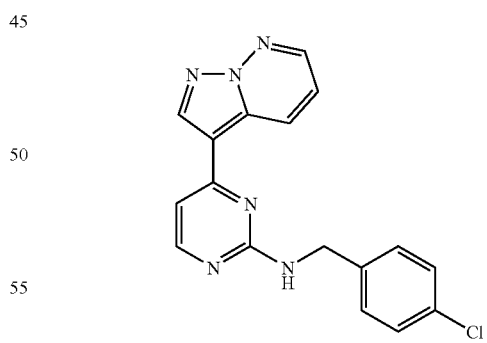

a) In a similar manner as described in Example 1a, from N-(4-chlorobenzyl)guanidine was obtained the title compound as a brown solid. $^1$H-NMR (400 MHz, d$^6$-DMSO) δ 9.20 (bs, 1H), 8.78 (bs, 1H), 8.54 (bs, 1H), 8.27 (d, 1H, J=5.1 Hz), 7.82 (m, 1H), 7.39 (m; 5H), 7.12 (d, 1H, J=5.4 Hz), 4.54 (s, 2H); MS (ESI) (M+H)$^+$ 337.

b) N-(4-Chlorobenzyl)guanidine.HO$_2$-CCF$_3$. Prepared from 4-chlorobenzylamine as described in (J. Med. Chem. (1975), 18(3), 304).

Example 19

N¹,N¹-Dimethyl-N³-(4-pyrazolo[1,5-b]pyridazin-3-yl-2-pyrimidinyl)-1,3-propanediamine

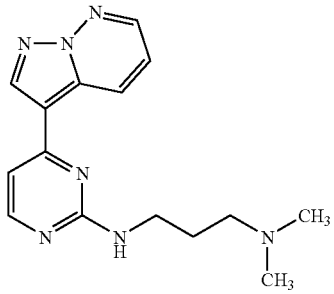

a) In a similar manner as described in Example 1a, from N-[3-(dimethylamino)propyl]guanidine.0.5H$_2$SO$_4$ was obtained the title compound as a yellow solid. $^1$H-NMR (400 MHz, d$^6$-DMSO) δ 9.10 (bs, 1H), 8.76 (s, 1H), 8.53 (dd, 1H, J=4.4, 2.0 Hz), 8:21 (d, 1H, J=5.2 Hz), 7.38 (dd, 1H, J=9.2, 4.4 Hz), 7.21 (bs, 1H), 7.05 (d, 1H, J=5.2 Hz), 2.87 (m, 2H), 2.50 (m. 2H), 2.27 (bs, 6H), 1.73 (m, 2H); MS (APCI) (M+H)$^+$ 298.

b) N-[3-(Dimethylamino)propyl]guanidine.0.5H$_2$SO$_4$. In a similar manner as described in Example 1e, from N-3-(dimethylamino)propylamine was obtained the title compound as a white solid. $^1$H-NMR (300 MHz, D$_2$O) δ 3.19 (t, 2H, J=6.6 Hz), 3.04 (m, 2H), 2.75 (s, 6H), 1.93 (m, 2H).

Example 20

N-[3-(4Morpholinyl)propyl]-4-pyrazolo[1,5-b]pyridazin-3-yl-2-pyrimidinamine

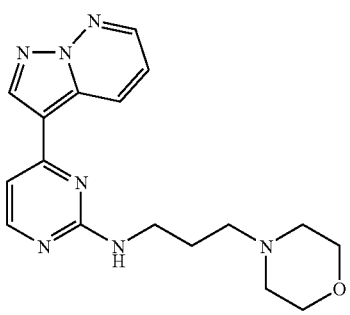

a) In a similar manner as described in Example 1a, from N-[3-(4-morpholinyl)propyl]guanidine.0.5H$_2$SO$_4$ was obtained the title compound as a yellow solid. $^1$H-NMR (300 MHz, d$^6$-DMSO) δ 9.10 (bs, 1H), 8.84 (s, 1H), 8.61 (dd, 1H, J=4.2, 2.0 Hz), 8.29 (d, 1H, J=5.1 Hz), 7.46 (dd, 1H, J=9.0, 4.2 Hz), 7.27 (bs, 1H), 7.11 (d, 1H, J=5.1 Hz), 3.58 (m, 2H), 3.40 (m, 2H), 3.31 (m, 2H), 2.54 (m, 2H), 2.40 (m, 4H), 1.78 (m, 2H); MS (APCI) (M+H)$^+$ 340.

b) N-[3-(4-Morpholinyl)propyl]guanidine.0.5H$_2$SO$_4$. In a similar manner as described in Example 1e, from N-3-(4-morpholinyl)propylamine was obtained the title compound (Bioorg. Med. Chem. Lett (1997), 7(6), 675) as a white solid. $^1$H-NMR (400 MHz, d$^6$-DMSO) δ 3.58 (bm, 4H), 3.15 (m, 4H), 3.05 (m, 4H), 1.85 (m, 2H).

Example 21

N-[3-(4Methyl-1-piperazinyl)propyl-4-pyrazolo[1,5-b]pyridazin-3-yl-2-pyrimidinamine

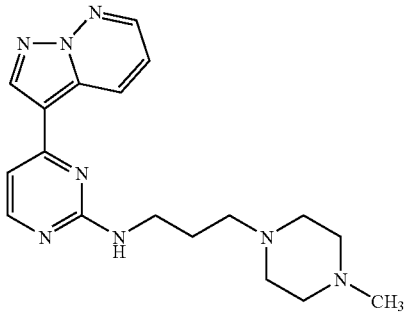

a) In a similar manner as described in Example 1a, from N-[3-(4-methyl-1-piperazinyl)propyl]guanidine.0.5H$_2$SO$_4$ was obtained the title compound as a yellow solid. $^1$H-NMR (400 MHz, d$^6$-DMSO) δ 9.00 (bs, 1H), 8.76 (s, 1H), 8.53 (dd, 1H, J=4.4, 2.0 Hz), 8.21 (d, 1H, J=5.6 Hz), 7.37 (dd, 1H, J=8.8, 4.0 Hz), 7.20 (bs, 1H), 7.03 (d, 1H, J=5.2 Hz), 3.32 (m, 6H), 2.34 (m, 6H), 2.11 (m, 3H), 1.68 (m, 2H); MS (APCI) (M+H)$^+$353.

b) N-[3-(4-Methyl-1-piperazinyl)propyl]guanidine.0.5H$_2$SO$_4$ In a similar manner as described in Example 1e, from N-3-(4-methyl-1-piperazinyl)propylamine was obtained the title compound (Bioorg. Med. Chem. Lett. (1997), 7(6), 675) as a white solid.

Example 22

1-{3-[(Pyrazolo[1,5-b]pyridazin-3-yl-2-pyrimidinyl)amino]propyl}-2-pyrrolidinone

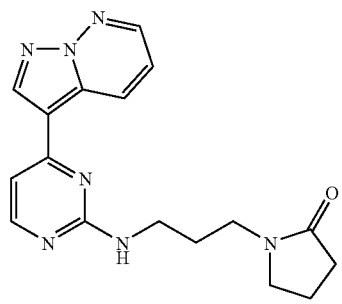

a) In a similar manner as described in Example 1a, from N-[3-(2-oxo-1-pyrrolidinyl)propyl]guanidine.HO$_2$-CCF$_3$ was obtained the title compound as a yellow solid. $^1$H-NMR (300 MHz, d$^6$-DMSO) δ 9.08 (bs, 1H), 8.84 (s, 1H), 8.61 (m, 1H), 8.30 (d, 1H, J=5.1 Hz), 7.47 (dd, 1H, J=8.9, 4.4 Hz), 7.22 (bs, 1H), 7.13 (d, 1H, J=5.3 Hz), 3.35 (m, 4H), 2.52 (m, 2H), 2.23 (m, 2H), 1.95 (m, 2H), 1.79 (m, 2H); MS (ESI) (M+H)$^+$338.

b) N-[3-(2-Oxo-1-pyrrolidinyl)propyl]guanidine.HO$_2$CCF$_3$. In a similar manner as described in Example 1e, from 1-(3-aminopropyl)-2-pyrrolidinone was obtained the title compound as a white solid.

Example 23

N-[3-Chloro-4-(4-methyl-1-piperazinyl)phenyl]-4-pyrazolo[1,5-b]pyridazin-3-yl-2-pyrimidinamine

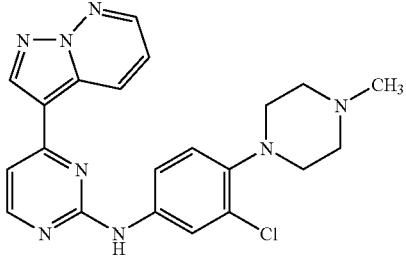

a) In a similar manner as described in Example 1a, from N-[3-chloro-4-(4-methyl-1-piperazinyl)phenyl]guanidine-.HNO$_3$ was obtained the title compound as a yellow solid. $^1$H-NMR (300 MHz, d$^6$-DMSO) δ 9.95 (s, 1H), 9.16 (d, 1H, J=8.6 Hz), 8.93 (s, 1H), 8.64 (m, 1H), 8.50 (d, 1H, J=2.4 Hz), 7.54 (dd, 1H, J=8.6, 2.4 Hz), 7.49 (dd, 1H, J=9.1, 4.4 Hz), 7.41 (d, 1H, J=5.2 Hz), 7.19 (d, 1H, J=8.8 Hz), 2.95 (m, 4H), 2.51 (m, 4H), 2.28 (s, 3H); MS (ESI) (M+H)$^+$ 421.

b) N[3-Chloro-4-(4-methyl-1-piperazinyl)phenyl]guanidine.HNO$_3$. In a similar manner as described in Example 7b, from 3-chloro-4-(4-methyl-1-piperazinyl)aniline was obtained the title compound as a white solid.

Example 24

N-[4-(4-Methyl-1-piperazinyl)phenyl]-4-pyrazolo[1,5-b]pyridazin-3-yl-2-pyrimidinamine

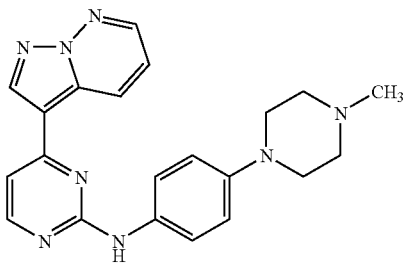

a) In a similar manner as described in Example 1a, from N-[4-(4-methyl-1-piperazinyl)phenyl]guanidine.HCl was obtained the title compound as a yellow solid. $^1$H-NMR (300 MHz, CDCl$_3$) δ 8.89 (d, 1H, J=9.0 Hz), 8.52 (s, 1H), 8.40 (m, 2H), 7.49 (d, 2H, J=8.8 Hz), 7.30 (s, 1H), 7.12 (dd, 1H, J=9.0, 4.3 Hz), 7.04 (m, 2H), 6.95 (m, 1H), 3.26 (m, 4H), 2.66 (m, 4H), 2.42 (s, 3H); MS (ESI) (M+H)$^+$ 387.

b) N-[4-(4-Methyl-1-piperazinyl)phenyl]guanidine.HCl. Prepared from 4-(4-methyl-1-piperazinyl)aniline as described in (J. Med. Chem. (1993), 36(19), 2716).

Example 25

N-[3-Methyl-4-(4-methyl-1-piperazinyl)phenyl]-4-pyrazolo[1,5-b]pyridazin-3-yl-2-pyrimidinamine

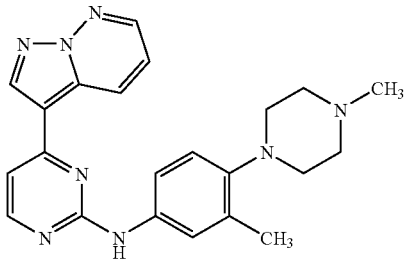

a) In a similar manner as described in Example 1a, from N-[3-methyl-4-(4-methyl-1-piperazinyl)phenyl]guanidine-.HNO$_3$ was obtained the title compound as a brown solid. $^1$H-NMR (400 MHz, d$^6$-DMSO) δ 9.35 (s, 1H), 9.11 (d, 1H, J=8.2 Hz), 8.86 (s, 1H), 8.58 (dd, 1H, J=4.6, 1.9 Hz), 8.41 (d, 1H, J=5.1 Hz), 7.55 (d, 1H, J=2.4 Hz), 7.43-7.40 (m, 2H), 7.30 (d, 1H, J=5.3 Hz), 7.00 (d, 1H, J=8.6 Hz), 2.83-2.81 (m, 4H), 2.50-2.48 (m, 4H), 2.24 (m, 6H); MS (ESI) (M+H)$^+$ 401.

b) N[3-Methyl-4-(4-methyl-1-piperazinyl)phenyl]guanidine.HNO$_3$. In a similar manner as described in Example 7b, from 3-methyl-4-(4-methyl-1-piperazinyl)aniline was obtained the title compound as a brown solid.

Example 26

N-[4-(4Methyl-1-piperazinyl)-3-(trifluoromethyl)phenyl]-4-pyrazolo[1,5-b]pyridazin-3-yl-2-pyrimidinamine

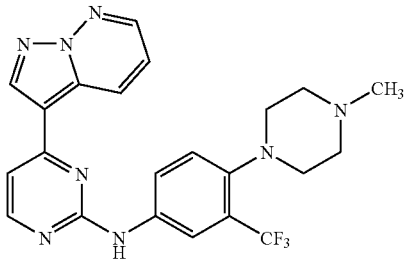

a) In a similar manner as described in Example 1a, from N-[4-(4-methyl-1-piperazinyl)-3-(trifluoromethyl)phenyl]guanidine.HNO$_3$ was obtained the title compound as a yellow solid. $^1$H-NMR (400 MHz, d$^6$-DMSO) δ 9.80 (s, 1H), 9.10 (d, 1H, J=8.1 Hz), 8.89 (s, 1H), 8.60 (dd, 1H, J=4.4, 2.0 Hz), 8.48 (d, 1H, J=5.3 Hz), 8.14 (d, 1H, J=2.4 Hz), 7.93 (d, 1H, J=8.8 Hz), 7.53 (d, 1H, J=8.8 Hz), 7.42 (m, 2H), 2.284 (m, 4H), 2.48 (m, 4H), 2.24 (s, 3H); MS (ESI) (M+H)$^+$ 455.

b) N-[4-(4-Methyl-1-piperazinyl)-3-(trifluoromethyl)phenyl] guanidine.HNO$_3$. In a similar manner as described in Example 7b, from 4-(4-methyl-1-piperazinyl)-3-(trifluoromethyl)phenylamine was obtained the title compound as a white solid.

Example 27

N-[3-Chloro-4-(4-morpholinyl)phenyl]-4-pyrazolo[1,5-b]pyridazin-3-yl-2-pyrimidinamine

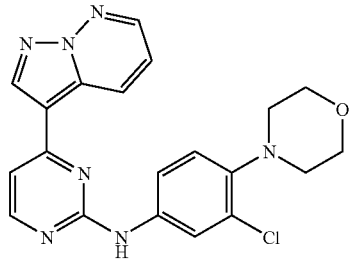

a) In a similar manner as described in Example 1a, from N-[3-chloro-4-(4-morpholinyl)phenyl]guanidine.HNO$_3$ was obtained the title compound as a yellow solid. $^1$H-NMR (300 MHz, d$^6$-DMSO) δ 9.67 (s, 1H), 9.17 (d, 1H, J=9.3 Hz), 8.93 (s, 1H), 8.64 (dd, 1H, J=4.4, 1.8 Hz), 8.51 (d, 1H, J=5.2 Hz), 8.06 (d, 1H, J=2.5 Hz), 7.58 (dd, 1H, J=8.7, 2.4 Hz), 7.50 (dd, 1H, J=9.1, 4.5 Hz), 7.42 (d, 1H, J=5.4 Hz), 7.21 (d, 1H, J=8.6 Hz), 3.77 (m, 4H), 2.97 (m, 4H); MS (ESI) (M+H)$^+$ 408.

b) N-[3-Chloro-4-(4-morpholinyl)phenyl]guanidine.HNO$_3$. In a similar manner as described in Example 7b, from 3-chloro-4-(4-morpholinyl)aniline was obtained the title compound as a brown solid. $^1$H-NMR (300 MHz, d$^6$-DMSO) δ 9.50 (s, 1H), 7.37 (bs, 5H), 7.23 (s, 2H), 3.77 (m, 4H), 2.99 (m, 4H); MS (ESI) (M+H)$^+$ 255.

Example 28

N-[{4-(Diethylamino)methyl]phenyl}-4-pyrazolo[1,5-b]pyridazin-3-yl-2-pyrimidinamine

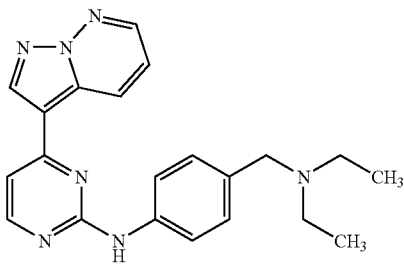

a) In a similar manner as described in Example 1a, from N-[4-(4-methyl-1-piperazinyl)-3-(trifluoromethyl)phenyl]guanidine.HNO$_3$ was obtained the title compound as a yellow solid. $^1$H-NMR (400 MHz, d$^6$-DMSO) δ 9.75 (bs, 1H), 9.40 (bs, 1H), 9.17 (d, 1H, J=8.8 Hz), 8.89 (s, 1H), 8.62 (d, 1H, J=2.7 Hz), 8.48 (d, 1H, J=5.1 Hz), 7.82 (bs, 2H), 7.45-7.39 (m, 3H), 4.24 (bs, 2H), 3.22 (bs, 4H), 1.20 (bs, 6H); MS (ESI) (M+H)$^+$ 374.

b) N-{4-[(Diethylamino)methyl]phenyl}guanidine.HNO$_3$. In a similar manner as described in Example 7b, from 4-[(diethylamino)methyl]aniline was obtained the title compound as a brown solid.

Example 29

N-[2-(Diethylamino)ethyl]-4-[(4-pyrazolo[1,5-b]pyridazin-3-yl-2-pyrimidinyl)amino]benzamide

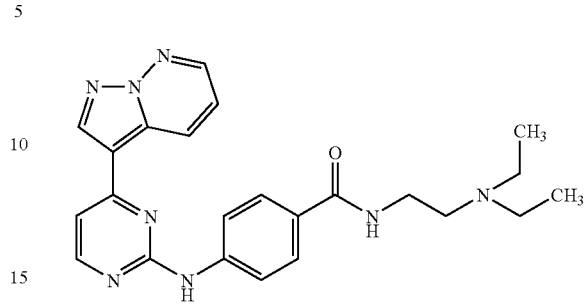

a) In a similar manner as described in Example 1a, from 4-{[amino(imino)methyl]amino}-N-[2-(diethylamino)ethyl]benzamide.HNO$_3$ was obtained the title compound as a yellow solid. $^1$H-NMR (300 MHz, d$^6$-DMSO) δ 9.89 (s, 1H), 9.24 (d, 1H, J=7.5 Hz), 8.95 (s, 1H), 8.66 (dd, 1H, J=4.5, 1.9 Hz), 8.56 (d, 1H, J=5.2 Hz), 7.90-7.83 (m, 4H), 7.52 (dd, 1H, J=9.0, 4.5 Hz), 7.47 (d, 1H, J=5.4 Hz), 5.42 (bs, 2H), 3.35 (bs, 2H), 2.60 (bs, 4H), 1.02 (bs, 6H); MS (ESI) (M+H)$^+$ 431.

b) 4-{[Amino(imino)methyl]amino}-N-[2-(diethylamino)ethyl] benzamide.HNO$_3$. In a similar manner as described in Example 7b, from 4-amino-N-[2-(diethylamino)ethyl]benzamide was obtained the title compound as a brown solid.

Example 30

N-Cyclopropyl(2-methylpyrazolo[1,5-b]pyridazin-3-yl)-2-pyrimidinamine

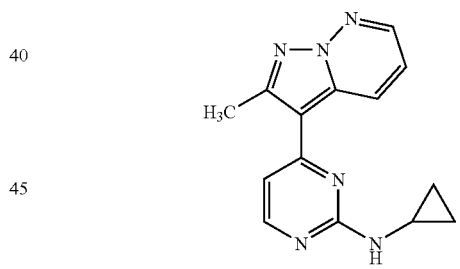

a) To a solution (2E)-3-(dimethylamino)-1-(2-methylpyrazolo[1,5-b]pyridazin-3-yl)-2-propen-1-one (50 mg, 0.22 mmol) in DMF (2.5 mL) was added N-cyclopropylguanidine.0.5H$_2$SO$_4$ (130 mg, 0.66 mmol) and potassium carbonate (152 mg, 1.10 mmol). The reaction was heated at an oil bath temperature of 135° C. for about 18 hours. The mixture was cooled to RT and the solvent was removed in vacuo. The residue was dissolved in chloroform and filtered. The filtrate was concentrated in vacuo then disolved in CH$_2$Cl$_2$ and triturated with diethylether to give the title compound as a yellow solid (22 mg, 38%). $^1$H-NMR (300 MHz, CDCl$_3$) δ 9.02 (d, 1H, J=8.8 Hz), 8.39 (d, 1H, J=5.2 Hz), 8.35 (dd, 1H, J=4.4, 2.0 Hz), 7.15 (dd, 1H, J=8.8, 4.4 Hz), 6.94 (d, 1H, J=5.3 Hz), 5.45 (s, 1H), 2.89 (m, 1H), 2.83 (s, 3H), 0.91 (m, 2H), 0.68 (m, 2H); MS (ESI) (M+H)$^+$ 267.

b) (2E)-3-(Dimethylamino)-1-(2-methylpyrazolo[1,5-pyridazin-3-yl)-2-propen-1-one. 1-(2-Methylpyrazolo[1,5-b]

pyridazin-3-yl)ethanone (165 mg, 0.95 mmol) was added to DMF dimethylacetal (6.0 mL). The reaction was heated at an oil bath temperature of 120° C. for about 3 days. The solvent was removed in vacuo. The residue was triturated with diethylether to give the title compound as a brown solid (60 mg, 26%). $^1$H-NMR (300 MHz, CDCl$_3$) δ 8.68 (dd, 1H, J=9.1, 2.0 Hz), 8.32 (dd, 1H, J=4.5, 2.0 Hz), 7.83 (d, 1H, J=12.4 Hz), 7.14 (dd, 1H, J=9.1, 4.5 Hz), 5.59 (d, 1H, J=12.4 Hz), 2.91-3.10 (bm, 6H), 2.81 (s, 3H); MS (APCI) (M+H)$^+$ 231.

c) 1-(2-Methylpyrazolo[1,5-b]pyridazin-3-yl)ethanone. To a slurry of 1-aminopyridazinium iodide (709 mg, 3.2 mmol) in DMSO (6.0 mL) was added 3-pentyne-2-one (1.45 g, 6.4 mmol) as a solution (2:1 by $^1$H NMR) in THF. The reaction flask was cooled in an ice bath at 4° C. then KOH (178 mg, 3.2 mmol) and K$_2$-CO$_3$ (219 mg, 1.59 mmol) were added in one portion. The bath was removed and the mixture was stirred at RT for about 4 hours. Water was added (20 mL). The organic layer was separated and the aqueous layer was extracted with CH$_2$Cl$_2$ (3×20 mL). The combined organic layers were dried (MgSO$_4$), filtered and concentrated in vacuo. The residue was triturated with diethyl ether and EtOAc to give the title compound as a red solid (165 mg, 29%). $^1$H-NMR (300 MHz, CDCl$_3$) δ 8.69 (dd, 1H, J.=9.1, 2.0 Hz), 8.42 (dd, 1H, J=4.7, 2.0 Hz), 7.29 (dd, 1H, J=9.1, 4.7 Hz), 2.82 (s, 3H), 2.62 (s, 3H).

d) 3-Pentyn-2-one. Propyne was condensed in THF at −78° C. until saturated. nBuLi (10 mL 25 mmol) was added in one portion. The reaction mixture was stirred for 10 minutes then dimethylacetamide (2.3 mL, 25 mmol) was added. The cooling bath was removed an the mixture was stirred at RT for about 1 hour. Water was added (100 mL) followed by the addition of diethylether (200 mL). The combined organic layers were dried (MgSO$_4$), filtered and concentrated in vacuo to about 2 mL. The THF solution was used in the next step.

Example 31

N-Cyclopropyl-4-(2-ethylpyrazolo[1,5-b]pyridazin-3-yl)-2-pyrimidinamine

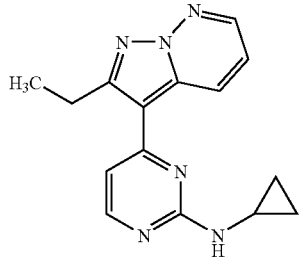

a) To a solution (2E)-3-(dimethylamino)-1-(2-ethylpyrazolo[1,5-b]pyridazin-3-yl)-2-propen-1-one (75 mg, 0.31 mmol) in DMF (2.0 mL) was added N-cyclopropylguanidine.0.5H$_2$SO$_4$ (181 mg, 0.92 mmol) and potassium carbonate (212 mg, 1.54 mmol). The reaction was heated at an oil bath temperature of 135° C. for about 18 hours. The mixture was cooled to RT and the solvent was removed in vacuo. The residue was dissolved in chloroform and filtered. The filtrate was concentrated in vacuo then disolved in CH$_2$Cl$_2$ and triturated with diethylether and hexanes to give the title compound as an orange solid (32 mg, 360% o). $^1$H-NMR (300 MHz, CDCl$_3$) δ 8.96 (d, 1H, J=8.7 Hz), 8.38 (d, 1H, J=5.4 Hz), 8.34 (dd, 1H, J=4.4, 1.9 Hz), 7.14 (dd, 1H, J=9.0, 4.5 Hz), 6.92 (d, 1H, J=5.4 Hz), 5.47 (s, 1H), 3.23 (q, 2H, J=7.5 Hz), 2.88 (m, 1H), 1.50 (t, 3H, J=7.5 Hz), 0.91 (m, 2H), 0.67 (m, 2H); MS (ESI) (M+H)$^+$ 281.

b) (2E)-3-(Dimethylamino)-1-(2-ethylpyrazolo[1,5-b]pyridazin-3-yl)-2-propen-1-one. 1-(2-Ethylpyrazolo[1,5-b]pyridazin-3-yl)ethanone (350 mg, 1.85 mmol) was added to DMF dimethylacetal (9.0 mL). The reaction was heated at an oil bath temperature of 120° C. for about 3 days. The solvent was removed in vacuo. The residue was triturated with diethylether to give the title compound as a brown solid (75 mg, 17%). The crude material was used without purification in the next step.

c) 1-(2-Ethylpyrazolo[1,5-b]pyridazin-3-yl)ethanone. To a slurry of 1-aminopyridazinium iodide (1.60 g, 7.2 mmol) in DMSO (14.0 mL) was added 3-hexyne-2-one (1.57 mL, 14.4 mmol). The reaction flask was cooled in an ice bath at 4° C. then KOH (403 mg, 7.2 mmol) and K$_2$-CO$_3$ (500 mg, 3.6 mmol) were added in one portion. The bath was removed and the mixture was stirred at RT for about 1 hour. Water was added (60 mL). The organic layer was separated and the aqueous layer was extracted with CH$_2$Cl$_2$ (3×50 mL). The combined organic layers were dried (MgSO$_4$), filtered and concentrated in vacuo. The residue was triturated with diethyl ether and EtOAc to give the title compound as a red solid (350 mg, 26%). $^1$H-NMR (300 MHz, CDCl$_3$) δ 8.67 (dd, 1H, J=9.0, 2.0 Hz), 8.42 (dd, 1H, J=4.5, 2.0 Hz), 7.29 (dd, 1H, J=9.0, 4.5 Hz), 3.23 (q, 2H, J=7.5 Hz), 2.66 (s, 3H), 1.50 (t, 3H, J=7.5 Hz); MS (ESI) (M+H)$^+$ 245.

Example 32

4-(2-Butylpyrazolo[1,5-b]pyridazin-3-yl)-N-cyclopropyl-2-pyrimidinamine

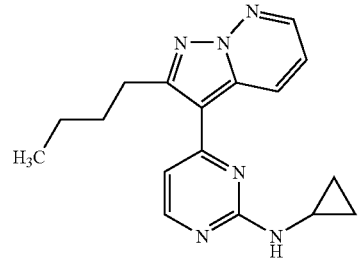

a) To a solution (2E)-3-(dimethylamino)-1-(2-methylpyrazolo[1,5-b]pyridazin-3-yl)-2-propen-1-one (50 mg, 0.22 mmol) in DMF (2.5 mL) was added N-cyclopropylguanidine.0.5H$_2$SO$_4$ (130 mg, 0.66 mmol) and potassium carbonate (152 mg, 1.10 mmol). The reaction was heated at an oil bath temperature of 135° C. for about 18 hours. The mixture was cooled to RT and the solvent was removed in vacuo. The residue was dissolved in chloroform and filtered. The filtrate was concentrated in vacuo then disolved in CH$_2$Cl$_2$ and triturated with diethylether to give the title compound as a yellow solid (22 mg, 38%). $^1$H-NMR (400 MHz, CDCl$_3$) δ 8.87 (d, 1H, J=7.2 Hz), 8.30 (d, 1H, J=5.2 Hz), 8.24 (dd, 1H, J=4.4, 2.0 Hz), 7.03 (dd, 1H, J=9.0, 4.4 Hz), 6.81 (d, 1H, J=5.3 Hz), 5.43 (s, 1H), 3.10 (t, 2H, J=7.5 Hz), 2.79 (m, 1H), 1.79 (m, 2H), 1.45 (m, 2H), 0.92 (t, 3H, J=7.5 Hz), 0.81 (m, 2H), 0.58 (m, 2H); MS (ESI) (M+H)$^+$ 309.

b) (2E)-1-(2-Butylpyrazolo[1,5-b]pyridazin-3-yl)-3-(dimethylamino)-2-propen-1-one. 1-(2-Methylpyrazolo[1,5-b]pyridazin-3-yl)ethanone (165 mg, 0.95 mmol) was added to DMF dimethylacetal (6.0 mL). The reaction was heated at an oil bath temperature of 120° C. for about 3 days. The solvent was removed in vacuo. The residue was triturated with diethylether to give the title compound as a brown solid (60 mg, 26%). The crude material was used without purification in the next step.

c) 1-(2-Butylpyrazolo[1,5-b]pyridazin-3-yl)ethanone. To a slurry of 1-aminopyridazinium iodide (1.60 g, 7.2 mmol) in DMSO (14.0 mL) was added 3-hexyne-2-one (1.57 mL, 14.4 mmol). The reaction flask was cooled in an ice bath at 4° C. then KOH (403 mg, 7.2 mmol) and K$_2$CO$_3$ (500 mg, 3.6 mmol) were added in one portion. The bath was removed and the mixture was stirred at RT for about 1 hour. Water was added (60 mL). The organic layer was separated and the aqueous layer was extracted with CH$_2$Cl$_2$ (3×50 mL). The combined organic layers were dried (MgSO$_4$), filtered and concentrated in vacuo. The residue was triturated with diethyl ether and EtOAc to give the title compound as a red solid (350 mg, 26%). $^1$H-NMR (300 MHz, CDCl$_3$) δ 8.65 (dd, 1H, J=9.0, 1.5 Hz), 8.42 (dd, 1H, J=4.4, 1.5 Hz), 7.29 (dd, 1H, J=9.0, 4.4 Hz), 3.18 (t, 2H, J=7.5 Hz), 2.65 (s, 3H), 1.88 (m, 2H), 1.54 (m, 2H), 1.02 (t. 3H, J=7.5 Hz); MS (APCI) (M+H)$^+$ 218.

d) 3-Octyn-2-one. To a solution of hexyne (2.3 mL, 20.0 mmol) in THF (20.0 mL) at −78° C. was added nBuLi (8.0 mL, 20 mmol) in one portion. The reaction mixture was stirred for 10 minutes then dimethylacetamide (1.85 mL, 20 mmol) was added. The cooling bath was removed an the mixture was stirred at RT for about 1 hour. Water was added (100 mL) followed by the addition of diethylether (200 mL). The combined organic layers were dried (MgSO$_4$), filtered and concentrated in vacuo to give the title compound as an oil. The crude material was used without purification in the next step.

Example 33

N-[4-(4Methyl-1-piperazinyl)phenyl]-4-(2-methylpyrazolo[1,5-b]pyridazin-3-yl)-2-pyrimidinamine

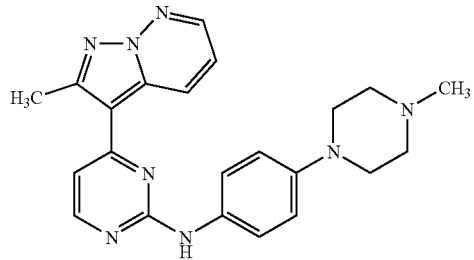

a) In a similar manner as described in Example 30a, from N-[4-(4-methyl-1-piperazinyl)phenyl]guanidine.HCl was obtained the title compound as a yellow solid. $^1$H-NMR (300 MHz, CDCl$_3$) δ 8.65 (dd, 1H, J=9.0, 1.8 Hz), 8.40 (d, 1H, J=5.2 Hz), 8.29 (dd, 1H, J=4.4, 2.0 Hz), 7.47 (d, 2H, J=8.9 Hz), 7.01 (dd, 1H, J=9.1, 4.6 Hz), 6.95 (m, 3H), 3.23 (m, 4H), 2.78 (s, 3H), 2.66 (m, 4H), 2.40 (s, 3H); MS (APCI) (M+H)$^+$ 401.

Example 34

4-(2-Ethylpyrazolo[1,5-b]pyridazin-3-yl)-N-[4-(4-methyl-1-piperazinylphenyl]-2-pyrimidinamine

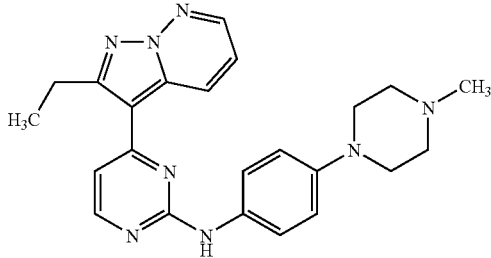

a) In a similar manner as described in Example 31a, from N-[4-(4-methyl-1-piperazinyl)phenyl]guanidine.HCl was obtained the title compound as a yellow solid. $^1$H-NMR (300 MHz, CDCl$_3$) δ 8.66 (dd, 1H, J=9.1, 1.9 Hz), 8.43 (d, 1H, J=5.2 Hz), 8.31(dd, 1H, J=4.4, 1.9 Hz), 7.51 (d, 2H, J=8.9 Hz), 6.9-7.1 (, 5H), 3.25 (m, 4H), 3.16 (q, 2H, J=7.5 Hz), 2.65 (m, 4H), 2.42 (s, 3H), 1.49 (t, 3H, J=7.5 Hz); MS (ESI) (M+H)$^+$ 415.

Example 35

4-(2-Butylpyrazolo[1,5-b]pyridazin-3-yl)-N-[4-(4-methyl-1-piperazinyl]phenyl]-2-pyrimidinamine

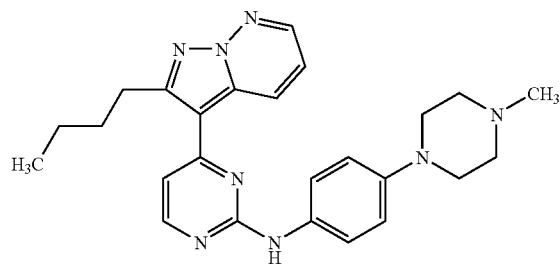

a) In a similar manner as described in Example 32a, from N-[4-(4-methyl-1-piperazinyl)phenyl]guanidine.HCl was obtained the title compound as a yellow solid. $^1$H-NMR (400 MHz, CDCl$_3$) δ 8.57 (dd, 1H, J=9.0, 1.9 Hz), 8.36 (d, 1H, J=5.3 Hz), 8.24 (dd, 1H, J=4.4, 2.0 Hz), 7.43 (d, 2H, J=8.9 Hz), 6.95 (dd, 1H, J=9.0, 4.4 Hz), 6.91 (d, 2H, J=8.9 Hz), 6.88 (d, 1H, J=5.2 Hz), 3.17 (m, 4H), 3.09 (t, 2H, J=7.5 Hz), 2.58 (m, 4H), 2.34 (s, 3H), 1.82 (m, 2H), 1.44 (m, 2H), 0.93 (t, 3H, J=7.5 Hz); MS (ESI) (M+H)$^+$ 443.

Example 36

N-Cyclopropyl-4-(6-methoxypyrazolo[1,5-b]pyridazin-3-yl)-2-pyrimidinamine

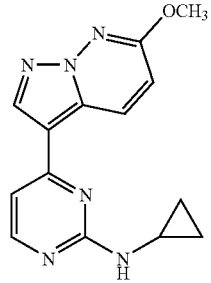

a) In a similar manner as described in Example 1a, from (2E)-3-(dimethylamino)-1-(6-methoxypyrazolo[1,5b]pyridazin-3-yl)-2-propen-1-one was obtained the title compound as a brown solid. $^1$H-NMR (300 MHz, CDCl$_3$) δ 8.95 (d, 1H, J=9.5 Hz), 8.30 (d, 1H, J=5.1 Hz), 8.28 (s, 1H), 6.91 (d, 1H, J=5.2 Hz), 6.83 (d, 1H, J=9.4 Hz), 5.39 (s, 1H), 4.09 (s, 3H), 2.88 (m, 1H), 0.87 (m, 2H), 0.64 (m, 2H); MS (ESI) (M+H)$^+$ 283.

b) (2E)-3-(Dimethylamino)-1-(6-methoxypyrazolo[1,5-b]pyridazin-3-yl)-2-propen-1-one. In a similar manner as described in Example 30b, from 1-(6-methoxypyrazolo[1,5-b]pyridazin-3-yl)ethanone was obtained the title compound as a brown solid. $^1$H-NMR (300 MHz, d$^6$ DSMO) δ 8.53 (d, 1H, J=9.5 Hz), 8.47 (s, 1H), 7.63 (d, 1H, J=12.4 Hz), 7.06 (d, 1H, J=9.5 Hz), 5.76 (d, 1H, J=12.4 Hz), 3.96 (s, 3H), 3.10 (bs, 3H), 2.90 (bs, 3H); MS (ESI) (M+H)$^+$ 247.

c) 1-(6-Methoxypyrazolo[1,5-b]pyridazin-3-yl)ethanone. 3-Methoxypyridazine.HCl (16.6 g, 151 mmol) was added to pH 8.0 buffer (250 mL) and heated at 70° C. HOSA (25.6 g, 227 mmol) in water (10 mL) was neutralized to about pH 7.5 by the addition of aqueous KHCO$_3$ (110 mL, 2.4 M). The HOSA solution was added dropwise via addition funnel over one hour. The reaction was cooled to RT and CH$_2$Cl$_2$ (250 mL) was added. The reaction mixture was cooled in an ice bath and 3-butyne-2-one (5.3 mL, 75 mmol) was added in one portion follwed by the dropwise addition of KOH (9.52 g, 169 mmol) in water (25 mL). The reaction mixture was allowed to warm to RT and stirred for about 2 hours. The aqueous layer was extracted with EtOAc (2×300 mL). The combined organic layers were washed with water (100 mL), dried. (MgSO$_4$), and concentrated in vacuo. The residue was triturated with EtOAc and hexanes to give the title compound as a red solid (5.6 g, 39%) $^1$H-NMR (300 MHz, CDCl$_3$) δ 8.54 (d, 1H, J=9.5 Hz), 8.24 (s, 1H), 6.95 (d, 1H, J=9.5 Hz), 4.09 (s, 3H), 2.55 (s, 3H); MS (ESI) (M+H)$^+$ 192.

d) 3-Methoxypyridazine.HCl. To a solution of 3-chloro-6-methoxypyridazine (2.9 g, 20.0 mmol) in methanol (30 mL) was added Pd/C (145 mg, 10% w/w). Hydrogen gas was bubbled through the solution and then a balloon of hydrogen gas was left over the reaction for about 12 hours. The reaction was filtered through Celite and the filtrate collected and concentrated in vacuo. The oil was used without further purification. $^1$H-NMR (300 MHz, CDCl$_3$) δ 9.47 (d, 1H, J=5.0 Hz), 8.26 (dd, 1H, J=9.1, 4.8 Hz), 7.70 (d, 1H, J=8.9 Hz), 4.19 (s, 3H).

Example 37

4-(6-Methoxypyrazolo[1,5-b]pyridazin-3-yl)-N-[4-(4-methyl-1-piperazinyl)phenyl]-2-pyrimidinamine

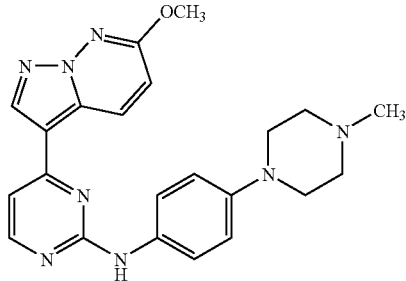

a) To a solution (2E)-3-(dimethylamino)-1-(6-methoxy-pyrazolo[1,5-b]pyridazin-3-yl)-2-propen-1-one (40 mg, 0.16 mmol) in DMF (2.0 mL) was added N-[4-((methyl-1-piperazinyl)phenyl]guanidine.HCl (99 mg, 0.32 mmol) and potassium carbonate (112 mg, 0.80 mmol). The reaction was heated at an oil bath temperature of 130° C. for about 18 hours. The mixture was cooled to RT and the solvent was removed in vacuo. The residue was dissolved in chloroform and filtered. The filtrate was concentrated in vacuo then disolved in CH$_2$Cl$_2$ and triturated, with diethylether to give the title compound as a yellow solid (12 mg, 18%). $^1$H-NMR (400 MHz, CDCl$_3$) δ 8.67 (d, 1H, J=9.5 Hz), 8.35 (d, 1H, J=5.2 Hz), 8.29 (s, 1H), 7.46 (d, 2H, J=8.9 Hz), 6.98 (m, 3H), 6.90 (s, 1H), 6.75 (d, 1H, J=9.5 Hz), 4.09 (s, 3H), 3.23 (m, 4H), 2.64 (m, 4H), 2.39 (s, 3H); MS (ESI) (M+H)$^+$ 417.

Example 38

3-[2-(Cyclopropylamino)-4-pyrimidinyl]pyrazolo[1,5-b]pyridazin-6-ol

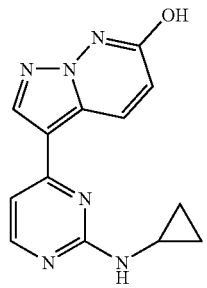

a) A solution of N-cyclopropyl-4-(6-methoxypyrazolo[1,5-b]pyridazin-3-yl)-2-pyrimidinamine (510 mg, 1.81 mmol) in morpholine (15 mL) was heated at an oil bath temperature of 130° C. for about 16 hours. The reaction mixture was cooled and the solvent removed in vacuo. The residue was disolved in CH$_2$Cl$_2$ and triturated with diethylether to give the title compound as a yellow solid (400 mg, 82%). $^1$H-NMR (300 MHz, d$^6$-DMSO) δ 8.96 (d, 1H, J=9.7 Hz), 8.49 (s, 1H), 8.23 (d, 1H, J=5.0 Hz), 7.35 (s, 1H), 7.06 (d, 1H, J=5.1 Hz), 6.97 (d, 1H, J=9.5 Hz), 2.74 (m, 1H), 0.73 (m, 2H), 0.49 (bs, 2H); MS (ESI) (M+H)$^+$ 269.

Example 39

N-Cyclopropyl-4-(6-isopropoxyppyrazolo[1,5-b]pyridazin-3-yl)-2-pyrimidinamine

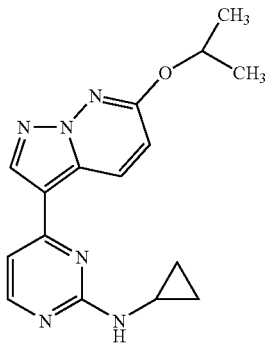

a) In a similar manner as described in Example 1a, from (2E)-3-(dimethylamino)-1-(6-isopropoxypyrazolo[1,5-b]pyridazin-3-yl)-2-propen-1-one was obtained the title compound as a brown solid. $^1$H-NMR (300 MHz, CDCl$_3$) δ 8.91 (d, 1H, J=9.5 Hz), 8.29 (d, 1H, J=5.2 Hz), 8.25 (s, 1H), 6.90 (d, 1H, J=5.3 Hz), 6.76 (d, 1H, J=9.7 Hz), 5.41 (septet, 1H, J=6.2 Hz), 5.35 (bs, 1H), 2.85 (m, 1H), 1.43 (d, 6H, J=6.2 Hz), 0.87 (m, 2H), 0.63 (m, 2H); MS (ESI) (M+H)$^+$ 311.

b) (2E)-3-(Dimethylamino)-1-(6-isopropoxypyrazolo[1,5-b]pyridazin-3-yl)-2-propen-1-one. In a similar manner as described in Example 30b, from 1-(6-isopropoxypyrazolo[1,5-b]pyridazin-3-yl)ethanone (150 mg, 0.7 mmol) was obtained the title compound as a brown solid. This material was used in the next step without further purification. MS (ESI) (M+H)$^+$ 275.

c) 1-(6-Isopropoxypyrazolo[1.5-b]pyridazin-3-yl)ethanone. To a solution of 1-(6-hydroxypyrazolo[1,5-b]pyridazin-3-yl)ethanone (200 mg, 1.13 mmol) in THF (8.0 mL) was added PPh$_3$ (445 mg, 1.70 mmol), DEAD (296 mg, 1.70 mmol) and iPrOH (0.432 mL, 5.65 mmol). The mixture was stirred at RT for about 14 hours. Water (20 mL) was added and the aqueous layer was washed with EtOAc (3×40 mL). The combined organic layers were dried (MgSO$_4$) and concentrated in vacuo to give the title compound as a white solid. This material was used in the next step without further purification. MS (ESI) (M+H)$^+$ 220.

d) 1-(6-Hydroxypyrazolo[1,5-b]pyridazin-3-yl)ethanone. To 1-(6-methoxypyrazolo[1,5-b]pyridazin-3-yl)ethanone (600 mg, 3.14 mmol) was added HI (10.0 mL, 57% in water). The reaction mixture was heated at an oil bath temperature of 90° C. for about 12 hours. The mixture was cooled to RT, the water layer was brought to pH 8.0 and washed with EtOAc (3×100 mL). The combined organic layers were dried (MgSO$_4$) and concentrated in vacuo to give the title compound as a yellow amorphous solid (365 mg, 63%). $^1$H-NMR (300 MHz, dr DMSO) δ 12.25 (bs, 1H),8.48 (s, 1H), 8.43 (d, 1H, J=9.5 Hz), 7.07 (d, 1H, J=9.5 Hz), 2.47 (s, 3H); MS (ESI) (M+H)$^+$ 178.

Example 40

N-[4-(6-Isopropoxypyrazolo[1,5-b]pyridazin-3-yl)-2-pyrimidinyl]-N-[4-(methyl-1-piperazinyl)phenyl]amine

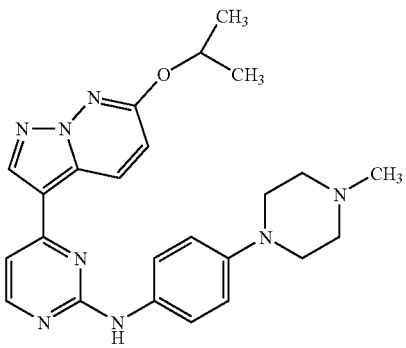

a) In a similar manner as described in Example 37a, from (2E)-3-(dimethylamino)-1-(6-isopropoxypyrazolo[1,5-b]pyridazin-3-yl)-2-propen-1-one was obtained the title compound as a brown solid. $^1$H-NMR (300 MHz, CDCl$_3$) δ 8.64 (d, 1H. J=9.6 Hz), 8.34 (d, 1H, J=5.2 Hz), 8.26 (s, 1H), 7.46 (d, 2H, J=8.8 Hz), 6.97 (m, 3H), 6.87 (s, 1H), 6.67 (d, 1H, J=9.6 Hz), 5.41 (m, 1H), 3.23 (m, 4H), 2.64 (m, 4H), 2.40 (s, 3H), 1.43 (d, 6H, J=6.1 Hz); MS (ESI) (M+H)$^+$ 445.

Example 41

3-[2-(Cyclopropylamino)-4-pyrimidinyl]pyrazolo[1,5-b]pyridazin-6-yl trifluoromethanesulfonate

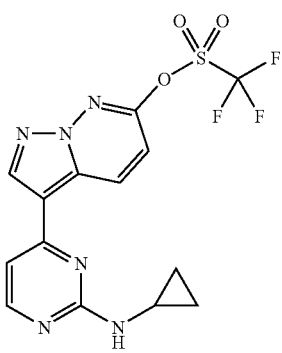

a) To a solution of 3-[2-(cyclopropylamino)-4-pyrimidinyl]pyrazolo[1.5-b]pyridazin-6-ol (10.0 g, 37.3 mmol) in DMF. (100 mL) was added N-phenyltrifluoromethylsulfonimide (15.0 g, 42.0 mmol) and DIEA (13 mL, 80 mmol). The reaction mixture was stirred at RT for about 2 hours. Water (500 mL) was added and the aqueous layer was washed with EtOAc (3×1 L). The combined organic layers were dried (MgSO$_4$) and concentrated in vacuo to give the a yellow amorphous solid. The solid was dissolved in CH$_2$Cl$_2$ and purified by slica-gel column, chromatography (gradient, 0-10% MeOH in CH$_2$Cl$_2$) to give the title compound as a white solid (7.4 g, 50%). $^1$H-NMR (300 MHz, CDCl$_3$) δ 9.36 (d, 1H, J=9.5 Hz), 8.54 (s, 1H), 8.35 (bs, 1H). 7.17 (d, 1H, J=9.4 Hz), 6.98 (d, 1H, J=5.3 Hz), 5.65 (bs, 1H), 2.85 (m, 1H), 0.90 (m, 2H), 0.67 (m, 2H); MS (ESI) (M+H)$^+$ 401.

Example 42

4-[6-(2-Chlorophenyl)pyrazolo[1,5-b]pyridazin-3-yl]-N-cyclopropyl-2-pyrimidinamine

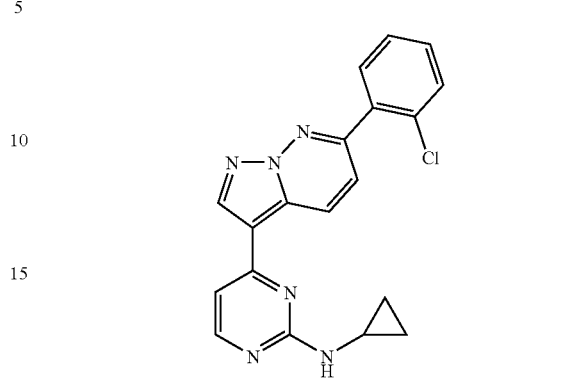

a) To a solution of 3-[2-(cyclopropylamino)-4-pyrimidinyl]pyrazolo[1,5-b]pyridazin-6-yl trifluoromethanesulfonate (21.0 mg, 0.08 mmol) in DMF (1 mL) was added Pd(PPh$_3$)$_2$Cl$_2$ (5 mg, 0.007 mmol), 2-chlorophenyl boronic acid (15 mg, 0.096 mmol), and Na$_2$-CO$_3$ (21.0 mg in 0.5 mL water). The reaction mixture was heated at an oil bath temperature of 100° C. for about 12 hours. The mixture was cooled to RT and water (20 mL) was added. The aqueous layer was washed with EtOAc (3×50 mL). The combined organic layers were dried (MgSO$_4$) and concentrated in vacuo and purified by silica-gel column chromatography (30% EtOAc/hexanes) to give the title compound as a brown solid (15 mg, 55%). $^1$H-NMR (300 MHz, CDCl$_3$) δ 9.14 (d, 1H, J=9.2 Hz), 8.52 (s, 1H), 8.32 (d, 1H, J=5.3 Hz), 7.74-7.71 (m, 1H), 7.56-7.52 (m, 2H), 7.46-7.42 (m, 2H), 5.61 (bs, 1H), 2.88 (m, 1H), 0.89 (m, 2H), 0.66 (m, 2H); MS (ESI) (M+H)$^+$ 363.

Example 43

N-Cyclopropyl-4-[6-(2-thienyl)pyrazolo[1,5-b]pyridazin-3-yl]-2-pyrimidinamine

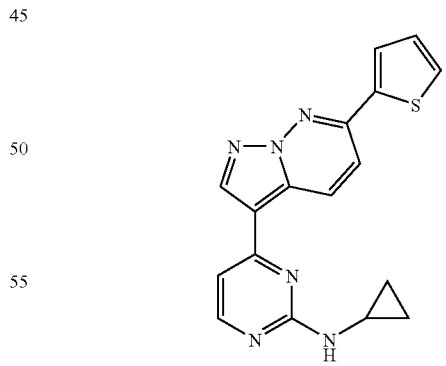

a) In a similar manner as described in Example 42a, from thiophene-2-boronic acid was obtained the title compound as a brown solid. $^1$H-NMR (300 MHz, CDCl$_3$) δ 9.09 (d, 1H, J=9.3 Hz), 8.48 (s, 1H), 8.20 (d, 1H, J=5.5 Hz), 7.76 (d, 1H, J=3.3 Hz), 7.63 (d, 1H, J=9.5 Hz), 7.54 (d. 1H, J=4.9 Hz), 7.19 (t, 1H, J=4.4 Hz), 6.99 (d, 1H, J=5.8 Hz), 2.91 (m, 1H), 0.95 (m, 2H), 0.74 (m, 2H); MS (ESI) (M+H)$^+$ 335.

Example 44

N-Cyclopropyl-4-[6-(4-fluorophenyl)pyrazolo[1,5-b]pyridazin-3-yl]-2-pyrimidinamine

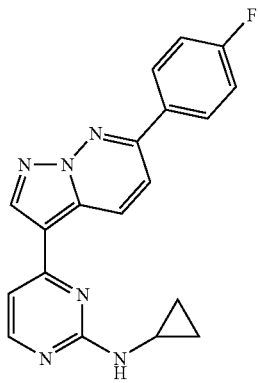

a) In a similar manner as described in Example 42a, from 4-fluorophenyl boronic acid was obtained the title compound as a brown solid. $^1$H-NMR (300 MHz, CDCl$_3$) δ 9.16 (d, 1H, J=9.3 Hz), 8.48 (s, 1H), 8.33 (d, 1H, J=4.6 Hz), 8.09 (dd, 2H, J=8.8, 5.2 Hz), 7.60 (d, 1H, J=9.3 Hz), 7.22 (t, 2H, J=8.6 Hz), 6.96 (d, 1H, J=5.2 Hz), 5.47 (bs, 1H), 2.88 (m, 1H), 0.90 (m, 2H), 0.67 (m, 2H); MS (APCI) (M+H)$^+$ 347.

Example 45

N-Cyclopropyl-4-(6-vinylpyrazolo[1,5-b]pyridazin-3-yl)-2-pyrimidinamine

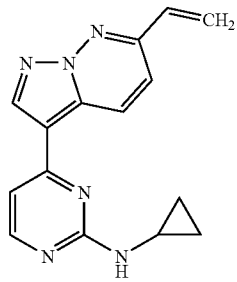

a) To a solution of 3-[2-(cyclopropylamino)-4-pyrimidinyl]pyrazolo[1,5-b]pyridazin-6-yl trifluoromethanesulfonate (100 mg, 0.25 mmol) in DMF (3 mL) was added Pd$_2$(dba)$_3$ (12 mg, 0.0125 mmol), LiCl (32 mg, 0.75 mmol), AsPh$_3$ (31 mg, 0.10 mmol), and vinyl-tributylstannane (120 mg, 0.375 mmol). The reaction mixture was heated at an oil bath temperature of 60° C. for about 4 hours. The mixture was cooled to RT and water (20 mL) was added. The aqueous layer was washed with EtOAc (3×50 mL). The combined organic layers were dried (MgSO$_4$) and concentrated in vacuo and purified by silica-gel column chromatography (gradient, 10-80% EtOAc in hexanes) to give the title compound as an off-white solid (26 mg, 37%). $^1$H-NMR (300 MHz, CDCl$_3$). δ 9.05 (d, 1H, J=9.3 Hz), 8.44 (s, 1H), 8.30 (d, 1H, J=5.3 Hz), 7.40 (d, 1H, J=9.4 Hz), 6.92 (m, 2H), 6.22 (d, 1H, J=17.7 Hz), 5.75 (d, 1H, J=11.2 Hz), 5.48 (bs, 1H), 2.86 (m, 1H), 0.90 (m, 2H), 0.66 (m, 2H); MS (ESI) (M+H)$^+$ 279.

Example 46

N-Cyclopropyl-4-[6-(4-morphoinyl)pyrazolo[1,5-b]pyridazin-3-yl]-2-pyrimidinamine

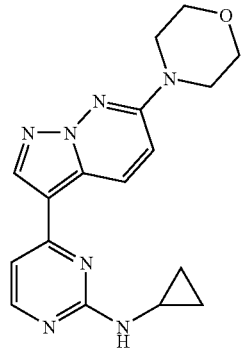

a) This product is isolated by silica-gel column chromatography from Example 41a. $^1$H-NMR (300 MHz, d$^6$-DMSO) δ 8.88 (d, 1H, J=9.8 Hz), 8.47 (s, 1H), 8.22 (d, 1H, J=5.0 Hz), 7.37 (m, 2H), 7.04 (d, 1H, J=5.2 Hz), 3.73 (t, 4H, J=4.6 Hz), 3.49 (t, 4H, J=4.7 Hz), 2.74 (m, 1H), 0.73 (m, 2H), 0.50 (m, 2H); MS (ESI) (M+H)$^+$ 338.

Example 47

N-Cyclopentyl-3-[2-(cyclopropylamino)-4-pyrimidinyl]pyrazolo[1,5-b]pyridazin-6-amine

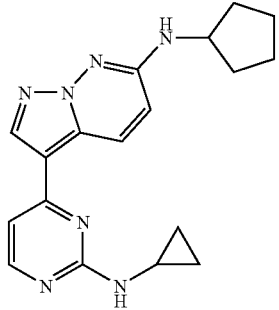

a) To a solution of 3-[2-(cyclopropylamino)-4-pyrimidinyl]pyrazolo[1,5-b]pyridazin-6-yl trifluoromethanesulfonate (107 mg, 0.268 mmol) in DMF (2 mL) was added DIEA (0.093 mL, 0.536 mmol) and cyclopentylamine (0.026 mL, 0.268 mmol). The reaction mixture was heated at an oil bath temperature of 50° C. for about 1 hour at which point N-phenyltrifluoromethylsulfonimide (95 mg, 0.268 mmol) was added followed by an additional portion (equivalent) of cyclopentylamine and DIEA This was repeated two more times. The mixture was cooled to RT and water (20 mL) was added. The aqueous layer was washed with EtOAc (3×50 mL). The combined organic layers were dried (MgSO$_4$) and concentrated in vacuo and purified by silica-gel column 0.15 chromatography (gradient, 0-10% MeOH in CH$_2$Cl$_2$). The residue was suspended in EtOAc and triturated with hexanes to give the title compound as a yellow solid (26 mg, 29%). $^1$H-NMR (300 MHz, CDCl$_3$) 8.71 (d, 1H, J=9.5 Hz), 8.17 (s, 2H), 6.89 (d, 1H, J=5.7 Hz), 6.55 (d, 1H, J=9.3 Hz), 5.92 (bs, 1H), 4.43 (m, 1H), 4.30 (m, 1H), 2.84 (m, 1H), 2.16 (m, 2H), 1.71 (m, 4H), 1.50 (m, 2H), 0.87 (m, 2H), 0.66 (m, 2H); MS (APCI) (M+H)$^+$ 336.

Example 48

N-Cyclopropyl-4-[6-(1-pyrrolidinyl)pyrazolo[1,5-b]pyridazin-3-yl]-2-pyrimidinamine

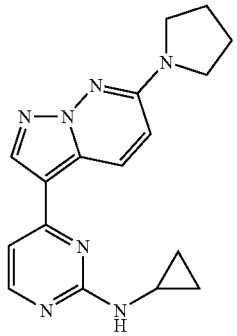

a) In a similar manner as described in Example 47a, from pyrrolidine was obtained the title compound as a yellow solid. $^1$H-NMR (300 MHz, CDCl$_3$) δ 8.83 (d, 1H, J=9.5 Hz), 8.29 (d, 1H, J=5.4 Hz), 8.20 (s, 1H), 6.92 (d, 1H, J=5.4 Hz), 6.74 (d, 1H, J=9.6 Hz), 5.36 (s, 1H), 3.60 (m, 4H), 2.88 (m, 1H), 2.09 (m, 4H), 0.90 (m, 2H), 0.67 (m, 2H); MS (ESI) (M+H)$^+$ 322.

Example 49

N-Cyclopropyl-4-[6-(2-fluoro-4-pyridinyl)pyrazolo[1,5-b]pyridazin-3-yl]-2-pyrimidinamine

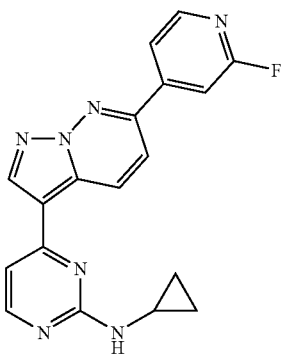

a) In a similar manner as described in Example 42a, from 2-fluoropyridyl-4-boronic acid was obtained the title compound as a brown solid. $^1$H-NMR (400 MHz, CDCl$_3$) δ 9.29 (bs, 1H), 8.56 (s, 1H), 8.42 (d, 1H, J=5.3 Hz), 8.37 (dd, 1H, J=9.5, 5.0 Hz), 7.90 (d, 1H, J=5.1 Hz), 7.63 (m, 2H), 6.98 (d, 1H, J=5.1 Hz), 5.41 (s, 1H), 2.88 (m, 1H), 0.91 (m, 2H), 0.67 (m, 2H); MS (ESI) (M+H)$^+$ 348.

Example 50

N-Cyclopropyl-4-[6-(phenylsulfanyl)pyrazolo[1,5-b]pyridazin-3-yl]-2-pyrimidinamine

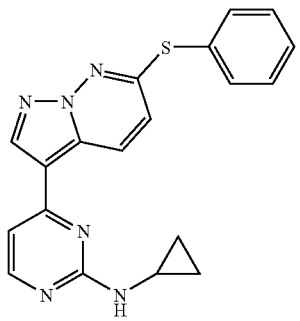

a) To a solution of 3-[2-(cyclopropylamino)-4-pyrimidinyl]pyrazolo[1,5-b]pyridazin-6-yl trifluoromethanesulfonate (250 mg, 0.625 mmol) in DMSO (8 mL) was added Pd(PPh$_3$)$_4$ (29 mg, 0.025 mmol), benzene thiol (0.064 mL, 0.625 mmol), and NaO$^t$Bu (120 mg, 1.31 mmol). The reaction mixture was heated at an oil bath temperature of 100° C. for about 2 hours. The mixture was cooled to RT and water (40 mL) was added. The aqueous layer was washed with EtOAc (3×60 mL). The combined organic layers were dried (MgSO$_4$) and concentrated in vacuo and purified by silica-gel column chromatography (gradient 50-100% EtOAc in hexanes) to give the title compound as a yellow solid (80 mg, 36%). $^1$H-NMR (400 MHz, CDCl$_3$) δ 8.90 (d, 1H, J=9.1 Hz), 8.34 (s, 1H), 8.29 (bs, 1H), 7.67 (m, 2H), 7.47 (m, 3H), 6.92 (d, 1H, J=5.3 Hz), 6.88 (d, 1H, J=9.4 Hz), 5.38 (s, 1H), 2.82 (m, 1H), 0.85 (m, 2H), 0.61 (m, 2H); MS (ESI) (M+H)$^+$ 361.

Example 51

4-[6-(4-Fluorophenyl)pyrazolo[1,5-b]pyridazin-3-yl]-N-(4-methoxyphenyl)-2-pyrimidinamine

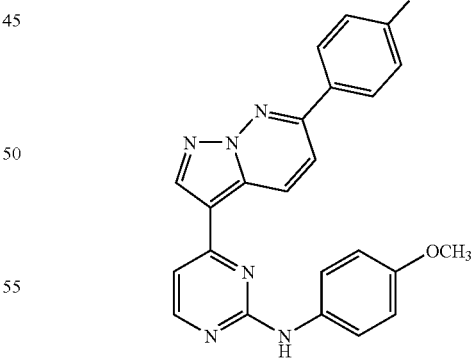

a) To a solution of 6-(4-fluorophenyl)-3-[2-(methylthio)pyrimidin-4-yl]pyrazolo[1,5-b]pyridazine (42 mg, 0.124 mmol) in MeOH (2 mL) was added Oxone (77 mg, 0.124 mmol) in water (1 mL). The reaction mixture was stirred for about 2 hours then water (10 mL) was added. The aqueous layer was washed with EtOAc (3×40 mL) and aqueous NaHCO$_3$ (1×20 mL). The combined organic layers were dried (MgSO$_4$) and concentrated in vacuo to give a brown solid. This solid was added to iPrOH (1.0 mL) and 4-methoxyaniline (20 mg, 0.162 mmol) in a sealed tube. The reaction mixture was heated at an oil bath temperature of 130° C. for about 16 hours. The mixture was cooled to RT and the solid collected by filtration to give the title compound as a brown solid (17 mg, 339% b). $^1$H-NMR (300 MHz, d$^6$-DMSO) δ 9.41 (s, 1H), 9.14 (d, 1H, J=9.1 Hz), 8.88 (s, 1H), 8.41 (d, 1H, J=5.1 Hz), 8.22 (dd, 2H, J=8.5, 5.6 Hz), 8.02 (d, 1H, J=9.3 Hz), 7.62 (d, 2H, J=8.8 Hz), 7.42 (t, 2H, J=8.8 Hz), 7.30 (d, 1H, J=5.2 Hz), 6.94 (d, 2H, J=8.8 Hz), 3.75 (s, 3H); MS (ESI) (M+H)$^+$ 413.

b) 6-(4-Fluorophenyl)-3-[2-(methylthio)pyrimidin-4-yl]pyrazolo[1,5-b]pyridazine. In a similar manner as described in Example 44-a, from 3-[2-(methylthio)pyrimidin-4-yl]pyrazolo[1,5-b]pyridazin-6-yl trifluoromethanesulfonate was obtained the title compound as a brown solid. $^1$H-NMR (300 MHz, CDCl$_3$) δ 9.02 (d, 1H, J=9.3 Hz), 8.54 (m, 2H), 8.10 (m, 2H), 7.69 (d, 1H, J=9.4 Hz), 7.31 (d, 1H, J=5.4 Hz), 7.21 (m, 2H), 2.71 (s, 3H); MS (ESI) (M+H)$^+$ 338.

c) 3-[2-(Methylthio)pyrimidin-4-yl]pyrazolo[1,5-b]pyridazin-6-yl trifluoromethanesulfonate. In a similar manner as described in Example 41a, from 3-[2-(methylthio)pyrimidin-4-yl]pyrazolo[1,5-b]pyridazin-6-ol was obtained the title compound as a brown solid. $^1$H-NMR (300 MHz, DMSO d$^6$) δ 8.62 (d, 1H, J=9.9 Hz), 8.62 (s, 1H), 8.52 (d, 1H, J=5.4 Hz), 7.60 (d, 1H, J=5.4 Hz), 7.46 (d, 1H, J=9.9 Hz), 2.58 (s, 3H); MS (ESI) (M+H)$^+$ 392.

d) 3-[2-(Methylthio)pyrimidin-4-yl]pyrazolo[1,5-b]pyridazin-6-ol. In a similar manner as described in Example 38a, from 6-methoxy-3-[2-(methylthio)pyrimidin-4-yl]pyrazolo[1,5-b]pyridazine was obtained the title compound as a brown solid. $^1$H-NMR (300 MHz, DMSO d$^6$) δ 8.57 (d, 1H, J=9.6 Hz), 8.53 (s, 1H), 8.49 (d, 1H, J=5.5 Hz), 7.57 (d, 1H, J=5.5 Hz), 6.91 (d, 1H, J=9.6 Hz), 2.57 (s, 3H); MS (ESI) (M+H)$^+$ 260.

e) 6-Methoxy-3-[2-(methylthio)pyrimidin-4-yl]pyrazolo[1,5-b]pyridazine. In a similar manner as described in Example 36c, from 4-ethynyl-2-(methylthio)pyrimidine was obtained the title compound as a brown solid. $^1$H-NMR (300 MHz, CDCl$_3$) δ 8.79 (d, 1H, J=9.6 Hz), 8.45 (d, 1H, J=5.3 Hz), 8.30 (s, 1H), 7.21 (d, 1H, J=5.4 Hz), 6.88 (d, 1H, J=9.4 Hz), 4.08 (s, 3H), 2.63 (s, 3H); MS (APCI) (M+H)$^+$ 274.

f) 4-Ethynyl-2-(methylthio)pyrimidine. To a solution of 4-iodo-2-(methylthio)pyrimidine (9.0 g, 35.7 mmol) in DMF (150 mL) was added TMS-acetylene (7.0 g, 71;43 mmol), TEA (15 mL, 107 mmol), CuI (0.70 g, 3.57 mmol), and Pd(PPh$_3$)$_2$Cl$_2$ (1.25 g, 1.79 mmol). The reaction mixture was heated at an oil bath temperature of 50° C. for about 1 hour. The mixture was cooled to RT and water (40 mL) was added. The aqueous layer was washed with EtOAc (3×60 mL). The combined organic layers were dried (MgSO$_4$) and concentrated in vacuo and purified by silica-gel column chromatography (gradient 10-40% EtOAc in hexanes) to give a yellow oil. The oil was dissolved in MeOH (20 mL) and cooled to 4° C. followed by addition of KF (2.0 g, 35 mmol). The mixture was stirred for about 5 minutes and poured onto a pad of silica-gel. The pad was washed with 50% EtOAc in hexanes. The fractions containing product were concentrated in vacuo to give the title compound as a yellow solid (4.0 g, 75%). $^1$H-NMR (300 MHz, CDCl$_3$) δ 8.51 (d, 1H, J=5.0 Hz), 7.07 (d, 1H, J=5.0 Hz), 3.34 (s, 1H), 2.57 (s, 3H); MS (ESI) (M+H)$^+$ 151.

g) 4-Iodo-2-(methylthio)pyrimidine. 4-Chloro-2-(methylthio)pyrimidine (24.5 g, 153 mmol) was added slowly to HI (100 mL, 30% in H$_2$O). The reaction was stirred at RT for about 14 hours. The mixture was neutralized with aqueous NaHCO$_3$. The solid was collected by filtration and dried under vacuum to give the title compound as a white solid (35 g, 91%).

Example 52

4-[6-(4-Fluorophenyl)pyrazolo[1,5-b]pyridazin-3-yl]-N-[4-(4-methyl-1-piperazinyl)phenyl]-2-pyrimidinamine

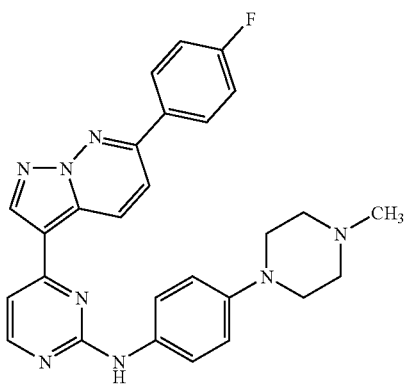

a) In a similar manner as described in Example 51a, from 4-(4-methylpiperazin-1-yl)aniline was obtained the title compound as a brown solid. $^1$H-NMR (400 MHz, CDCl$_3$) δ 8.88 (d, 1H, J=9.3 Hz), 8.48 (s, 1H), 8.38 (d, 1H, J=5.1 Hz), 8.07 (dd, 2H, J=8.8, 5.3 Hz), 7.50 (t, 3H, J=8.4 Hz), 7.22 (t, 2H, J=8.7 Hz), 7.02-6.98 (m, 3H), 6.94 (s, 1H), 3.23 (t, 4H, J=4.9 Hz), 2.63 (m, 4H), 2.38 (s, 3H); MS (ESI) (M+H)$^+$ 481.

Example 53

N-$^1$-N$^1$-Dimethly-N$^4$-{4-[6-(4-morpholinyl)pyrazolo[1,5-b]pyridazin-3-yl]-2-pyrimidinyl}-1,4-benzenediamine

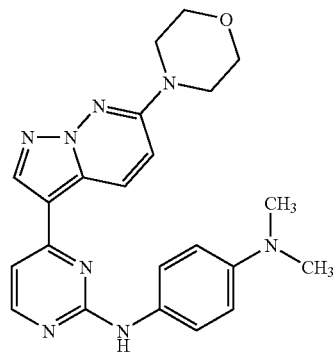

a) To a solution 3-[2-(methylthio)pyrimidin-4-yl]-6-morpholin-4-ylpyrazolo[1,5-b]pyridazine (116 mg, 0.354 mmol) in MeOH (10 mL) was added Oxone (456 mg, 0.741 mmol) in water (4 mL). The reaction mixture was stirred for about 2 hours then water (20 mL) was added. The aqueous layer was washed with EtOAc (3×80 mL) and aqueous NaHCO$_3$ (1×30 mL). The combined organic layers were dried (MgSO$_4$) and concentrated in vacuo to give a brown solid. This solid was added to iPrOH (2.0 mL) and N,N-dimethylbenzene-1,4-diamine (72 mg, 0.53 mmol) in a sealed tube. The reaction mixture was heated at an oil bath temperature of 130° C. for about 16 hours. The mixture was cooled to RT and the solid collected by filtration to give the title compound as a brown solid (18.6 mg, 13%). $^1$H-NMR (300 MHz, CDCl$_3$) δ 8.65 (d, 1H, J=9.8 Hz), 8.35 (d, 1H, J=5.4 Hz), 8.27 (s, 1H), 7.46 (d, 2H, J=8.9 Hz), 6.97 (d, 1H, J=5.2 Hz), 6.88-6.82 (m, 4H), 3.90 (t, 4H, J=4.8 Hz), 3.61 (t, 4H, J=4.9 Hz), 3.01 (s, 6H); MS (ESI) (M+H)$^+$ 417.

b) 3-[2-(Methylthio)pyrimidin-4-yl]-6-morpholin-4-ylpyrazolo[1,5-b]pyridazine. To a solution of 3-[2-(methylthio)pyrimidin-4-yl]pyrazolo[1,5-b]pyridazin-6-yl trifluoromethanesulfonate (165 mg, 0.635 mmol) in DMF (2 mL) was added morpholine (60 mg, 0.697 mmol). The reaction was stirred for about 12 hours then water (40 mL) was added. The aqueous layer was washed with EtOAc (3×60 mL). The combined organic layers were dried (MgSO$_4$) and concentrated in vacuo and purified by trituration with EtOAc/hexanes to give the title compound as a white solid (85 mg, 41%).

Example 54

1-(Dimethylamino)-3-[4-({4-[6-(4-morpholinyl)pyrazolo[1,5-b]pyridazin-3-yl]-2-pyrimidinyl}amino)phenoxy]-2-propanol

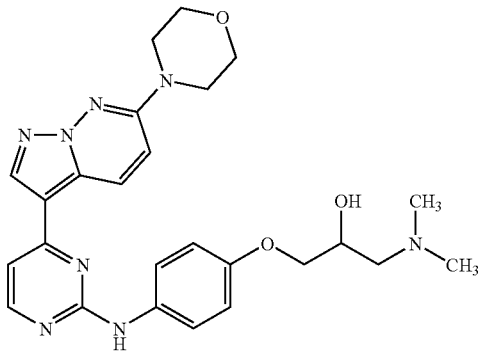

a) In a similar manner as described in Example 53a, from 1-(4-aminophenoxy)-3-(dimethylamino)propan-2-ol was obtained the title compound as a brown solid. $^1$H-NMR (400 MHz, d$^6$-DMSO) δ 9.31 (s, 1H), 8.78 (bd, 1H, J=9.1 Hz), 8.52 (s, 1H), 8.34 (d, 1H, J=5.3 Hz), 7.58 (d, 2H, J=9.0 Hz), 7.35 (d, 1H, J=9.9 Hz), 7.19 (d, 1H, J=5.3 Hz), 6.91 (d, 2H, J=9.0 Hz), 4.81, (d, 1H, J=4.4 Hz), 3.94-3.80 (m, 3H), 3.74 (t, 4H, J=4.8 Hz), 3.50 (t, 4H, J=4.7 Hz), 2.38 (dd, 1H, J=12.3, 5.6 Hz), 2.27 (dd, 1H, J=12.4, 6.5 Hz); MS (ESI) (M+H)$^+$ 491.

Example 55

N-(1,3-benzodioxol-5-yl)pyrazolo[1,5-b]pyridazin-3-yl-2-pyrimidinamine

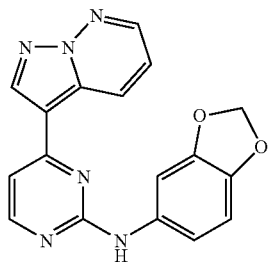

In a similar manner as described in Example 51, from 1,3-benzodioxolan-6-amine was obtained the title compound. $^1$H-NMR (300 MHz, d$^6$-DMSO) δ 9.47 (s, 1H), 9.17 (d, 1H, J=9.1 Hz), 8.90 (s, 1H), 8.64 (d, 1H, J=1.8 Hz), 8.46 (d, 1H, J=5.3 Hz), 7.46 (m, 2H), 7.36 (d 1H, J=5.2 Hz), 7.15 (d, 1H, J=8.6 Hz), 6.93 (d, 1H, J=8.4 Hz), 6.02 (s, 2H); MS (ESI) (M+H)$^+$ 333.

Example 56

N-(2,3-Dihydro-1,4-benzodioxin-6-yl)-4-pyrazolo[1,5-b]pyridazin-3-yl-2-pyrimidinamine

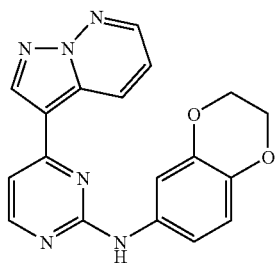

In a similar manner as described in Example 51, from 1,4-benzodioxan-6-amine was obtained the title compound. $^1$H-NMR (300 MHz, d$^6$-DMSO) δ 9.52 (s, 1H), 9.20 (d, 1H, J=9.6 Hz), 8.92 (s, 1H), 8.64 (s 1H), 8.49 (d, 1H, J=5.1 Hz), 7.57 (s, 1H), 7.51 (m, 1H), 7.39 (d, 1H, J=5.2 Hz), 7.27 (d, 1H, J=8.2 Hz), 6.99 (d, 1H, 8.7 Hz), 4.17 (m, 2H), 2.12 (m, 2H); MS (ESI) (M+H)$^+$ 347.

Example 57

N-[3-Methoxy-5-(trifluoromethylphenyl]-4-pyrazolo[1,5-b]pyridazin-3-yl-2-pyrimidinamine

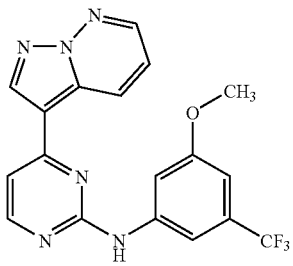

a) In a similar manner as described in Example 1a, from N-(3-methoxy-(5-trifluoromethyl)phenyl)guanidine nitrate was obtained the title compound. $^1$H-NMR (300 MHz, d$^6$-DMSO) δ 9.89 (s, 1H), 9.14 (d, 1H, J=8.8 Hz), 8.90 (s, 1H), 8.62 (s 1H), 8.53 (d, 1H, J=5.2 Hz), 7.82 (s, 1H), 7.65 (s, 1H), 7.45 (m, 2H), 6.83 (s, 1H), 3.31 (s, 3H) MS (ESI) (M+H)$^+$ 388.

b) N-(3-Methoxy-(5-trifluoromethyl)phenyl)guanidine nitrate.

In a similar manner as described in Example 7b, from 3-methoxy-(5-trifluoromethyl)phenylguanidine nitrate was obtained the title compound. $^1$H-NMR (300 MHz, d$^6$-DMSO) δ 9.75 (s, 1H), 7.54 (br s, 3H), 7.49-7.09 (m, 3H), 3.83 (s, 3H); MS (ESI) (M+H)$^+$ 234.

Example 58

4-[(4-Pyrazolo[1,5-b]pyridazin-3-yl-2-pyrimidinyl)amino]benzonitrile

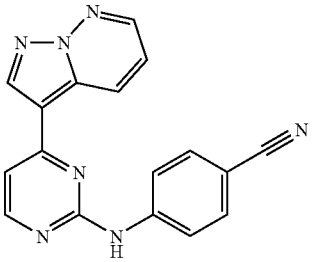

a) In a similar manner as described in Example 1a, from N-(4-cyanophenyl)guanidine nitrate was obtained the title compound. $^1$H-NMR (300 MHz, d$^6$-DMSO) δ 10.09 (s, 1H), 9.15 (d, 1H, J=8.6 Hz), 8.91 (s, 1H), 8.61 (s 1H), 8.54 (d, 1H, J=4.7 Hz), 7.97 (d, 2H, J=8.1 Hz), 7.76 (d, 2H, J=8.2 Hz), 7.48 (s, 2H); MS (ESI) (M+H)$^+$ 314.

b) N-(4-Cyanophenyl)guanidine nitrate

In a similar manner as described in Example 7b, from 4-aminobenzonitrile was obtained the title compound. $^1$H-NMR (300 MHz, d$^6$-DMSO) δ 10.0 (s, 1H), 7.87 (d, 2H, J=9.3 Hz), 7.73 (br s, 3H), (d, 2H, J=8.5 Hz); MS (ESI) (M+H)$^+$ 161.

Example 59

N-(4-Nitrophenyl)-4-pyrazolo[1,5-b]pyridazin-3-yl-2-pyrimidinamine

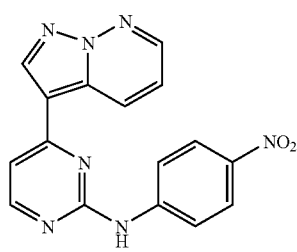

In a similar manner as described in Example 1a, from N-(4-nitrophenyl)guanidine nitrate was obtained the title compound. $^1$H-NMR (300 MHz, d$^6$-DMSO) δ 10.32 (s, 1H), 9.17 (d, 1H, J=9.0 Hz), 8.91 (s, 1H), 8.62 (d 1H, J=4.0 Hz), 8.57 (d, 1H, J=5.3 Hz), 8.22 (d, 2H, J=8.9 Hz), 8.02 (d, 2H, J=9.0 Hz), 7.52 (m, 2H); MS (ESI) (M+H)$^+$ 334.

Example 60

N-(3-Methoxyphenyl)-4-pyrazolo[1,5-b]pyridazin-3-yl-2-pyrimidinamine

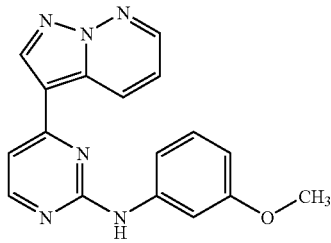

In a similar manner as described in Example 51a, from 3-methoxyaniline was obtained the title compound. $^1$H-NMR (300 MHz, d$^6$-DMSO) δ 9.56 (s, 1H), 9.21 (d, 1H. J=9.1 Hz), 8.89 (s, 1H), 8.62 (m, 1H), 8.49 (d, 1H, J=5.3 Hz), 7.47-7.20 (m, 5H), 3.75 (s, 3H); MS (ESI) (M+H)$^+$ 319.

Example 61

N-(3,5-Dimethylphenyl)-4-pyrazolo[1,5-b]pyridazin-3-yl-2-pyrimidinamine

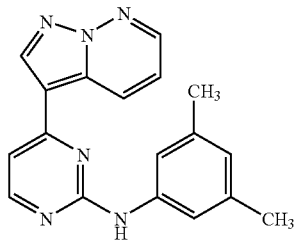

a) In a similar manner as described in Example 1a, from N-(3,5-dimethylphenyl)guanidine nitrate was obtained the title compound. $^1$H-NMR (300 MHz, d$^6$-DMSO) δ 9.47 (s, 1H), 9.18 (d, 1H, J=8.8 Hz), 8.92 (s, 1H), 8.62 (m, 1H), 8.50 (d, 1H, J=5.1 Hz), 7.48-7.37 (m, 4H), 6.67 (s, 1H), 2.29 (s, 6H); MS (ESI) (M+H)$^+$317.

b) N-(3,5-Dimethylphenyl)guanidine nitrate

In a similar manner as described in Example 7b, from 3,5-dimethylaniline was obtained the title compound.

Example 62

N-(4-aminosulfonylphenyl)-4-pyrazolo[1,5-b]pyridazin-3-yl-2-pyrimidinamine

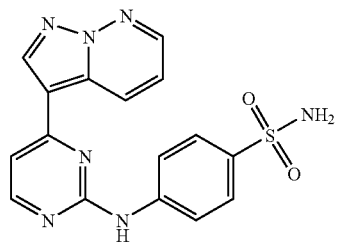

a) In a similar manner as described in Example 1a except the reaction was performed using n-butoxyethanol as solvent and was heated in a microwave at 180° C. for 20 minutes, from N-(4-aminosulfonylphenyl)guanidine carbonate was obtained the title compound as a light yellow solid. $^1$H-NMR (400 MHz, d$^6$-DMSO) δ 10.0 (s, 1H), 9.20 (d, 1H, J=9.2 Hz), 8.94 (s, 1H), 8.64 (dd, 1H, J=2.0, 4.4 Hz), 8.55 (d, 1H, J=5.6 Hz), 7.94 (d, 2H, J=8.8 Hz), 7.78 (d, 1H, J=8.8 Hz), 7.53-7.47 (m, 2H) 7.21 (s, 2H); MS (ESI) (M+H)$^+$ 368.

b) N-(4-aminosulfonylphenyl)guanidine carbonate: To a solution of sulfanilamide (0.26 g, 1.5 mmol) in conc. HCl (0.4 mL) was added cyanamide (0.6 mL of a 50% w/w solution in water) The mixture was heated at an oil bath temperature of 100° C. for about 20 min. The flask was allowed to cool to RT. The resulting oil was transferred to a beaker containing ice-cold sat. NaHCO$_3$. The solution was allowed to cool in the freezer overnight. The resulting precipitate was filtered and the solids were dried under vacuum (1 torr) for about 18 hours to give the title compound as a white powder (0.32 g, 77%). $^1$H-NMR (400 MHz, d$^6$-DMSO) δ 7.59 (d, 2H, J=8.5 Hz), 6.88 (d, 2H, J=8.0 Hz); MS (ESI) (M+H)$^+$ 215.

Example 63

N-(4-methylsulfonylphenyl)-4-pyrazolo[1,5-b]pyridazin-3-yl-2-pyrimidinamine

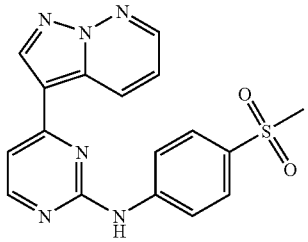

a) In a similar manner as described in Example 62a from N-(4-methylsulfonylphenyl)guanidine carbonate was obtained the title compound as an off-white solid $^1$H-NMR (400 MHz, d$^6$-DMSO) δ 10.13 (s, 1H), 9.21 (d, 1H, J=8.8 Hz), 8.95 (s, 1H), 8.65 (dd, 1H, J=2.0, 4.4 Hz), 8.57 (d, 1H, J=5.6 Hz), 8.04 (d, 2H, J=8.8 Hz), 7.87 (d, 1H, J=8.8 Hz), 7.54-7.49 (m, 2H) 3.18 (s, 3H); MS (ESI) (M+H)$^+$ 366.

b) N-(4-methylsulfonylphenyl)guanidine carbonate: In a similar manner as described in Example 62b, from 4-(methylsulfonyl)aniline was obtained the title compound.

Biological Data

The compounds of the present invention have valuable pharmacologic properties. Different compounds from this class are particularly effective at inhibiting CDK2 and/or CDK4 enzymes at concentrations, which range from 0.0001 to 1 µM and additionally show specificity relative to other kinases. Representative data is shown in Table 2 following. Substrate phosphorylation assays were carried out as follows.

CDK4

Cyclin D1 and cyclin-dependent kinase 4 were expressed utilizing a baculovirus expression system. The catalytic activity of CDK4 protein was assayed by measuring the phosphorylation of Rb protein. A truncated Rb protein (residues 773-928 of the native retinoblastoma protein, fused to glutathione S-transferase to facilitate purification) was used as the phosphoryl acceptor. The assay conditions were 100 mM HEPES (N-[2-hydroxyethyl]piperzine-N'-[2-ethanesulfonic acid]), pH 7.5, 0.5 µM GST-Rb protein, 1 µCi/mL [$^{33}$P]-ATP (1 nM-20 µM), 5-20 mM MgCl$_2$, 2.5 mM EDTA, 1 mM dithiothreitol, 0.2 mg/mL bovine serum albumin, 2% (v/v) dimethyl sulfoxide (DMSO), CDK4 enzyme (5-50 nM) in a final volume of 50 µL Reactions were incubated for time periods of 10-60 min at 30° C. and terminated by the addition of 50 µL quench (1 mM ATP/100 mM EDTA, pH 7.0). Detection of protein phosphorylation was accomplished by scintillation counting following collection of protein in 96 well plates coated with Glutathione or trapping of protein onto phosphocellulose filters. Counts detected by these methodologies minus the appropriate background were assumed to be proportional to the reaction initial rates. IC$_{50}$ values were determined by measuring enzyme activity in the presence of different inhibitor concentrations (0.1 nM to 50 µM). IC$_{50}$s were determined by a least squares fit to the equation CPM=Vmax*(1-([I]/(K+[I])))+nsb, or pIC50s were determined by a fit to the equation CPM=nsb+(Vmax−nsb)/(1+(x/10$^x$−pIC50)), where nsb are the background counts.

CDK2

Cyclin dependent protein kinase 2 assays utilized the peptide Biotin-aminohexyl-ARRPMSPKKKA-NH$_2$ as phosphoryl group acceptor. CDK2 was expressed utilizing a baculovirus expression system and was partially purified to comprise 20-80% of total protein, with no detectable competing reactions present. Typically, assays were performed by incubating enzyme (0.2-10 nM), with and without inhibitor, peptide substrate (1-10 nM), [g-$^{32}$P]ATP (1-20 nM), and 10-20 mM Mg$^{2+}$ for periods of time generally within the range 10-120 minutes Reactions were terminated with 0.2-2 volumes of either 20% acetic acid or 50-100 mM EDTA buffered to pH 7 (substrate consumption <20%). The buffer employed in enzyme assay was 100 mM HEPES pH 7.5 containing 0.1 mg/mL BSA and 5% DMSO. Inhibitors were diluted in 100% DMSO prior to addition into the assay. Detection of peptide phosphorylation was accomplished by scintillation counting following either collection of peptide onto phosphocellulose filters (for reactions stopped with acetic acid), collection of peptide in wells of 96 well plates coated with Streptavidin (Pierce) (reactions were stopped with EDTA), or addition of Avidin coated Scintillant impregnated beads (Scintillation Proximity Assays from Amersham, reactions were stopped with EDTA). Counts detected by any of these methodologies minus the appropriate background (assays with additional 40 mM EDTA or lacking peptide substrate) were assumed to be proportional to the reaction initial rates, and IC50s were determined by a least squares fit to the equation CPM=V$_{max}$*(1-([I]/(K+[I])))+nsb, or −pIC50s were determined by a fit to the equation CPM=nsb+(V$_{max}$−nsb)/(1+(x/10$^x$−pIC50)), where nsb are the background counts, filters and washed four times with 75 mM phosphoric acid. Radioactivity was determined by liquid scintillation counting.

TABLE 2

| Example # | CDK4 inhibition | CDK2 inhibition |
|---|---|---|
| 1 | +++ | ++ |
| 5 | +++ | +++ |
| 7 | +++ | +++ |
| 9 | +++ | +++ |
| 10 | +++ | +++ |
| 14 | +++ | +++ |
| 22 | +++ | +++ |

TABLE 2-continued

| Example # | CDK4 inhibition | CDK2 inhibition |
|---|---|---|
| 23 | +++ | +++ |
| 25 | +++ | +++ |
| 36 | ++ | ++ |
| 42 | ++ | ++ |
| 53 | +++ | ++ |
| 62 | | +++ |

Scale
+++ = <0.1 μM
++ = <1.0 μM
+ = <10 μM

Animal Model for Chemoprotection

Neonatal rat model of chemotherapy-induced alopecia: Time-pregnant female Sprague Dawley rats were purchased from Charles River Breeding Laboratories. Rat pups born on the same day were randomized at birth to 15 or 16 pups/mom/cage and were housed with moms during the study period. Each experimental group consisted of either 5 or 8 rats. For the etoposide model of CIA, rat pups received etoposide (VePesid, Bristol Laboratories Oncology Products, Princeton, N.J.) 6 mg/kg, ip, at 13 days of age (23). Compounds (0.05-50 mg/mL) were formulated in 100% DMSO and applied topically to the scalp 4 hours and 2 hours prior to etoposide injection. For the cyclophosphamide/doxorubicin model of CIA, pups received cyclophosphamide (Cytoxan, Mead Johnson Oncology Products, Princeton, N.J.) 35 mg/kg, ip, on day 12 and doxorubicin (Adriamycin, PharmaciaEtUpjohn Co., Kalamazoo, Mich.) 2.25 mg/kg, ip, on days 12 and 13. Compounds were formulated in 100% DMSO and applied topically to the scalp, 50 μL per application. Pups were treated with two topical applications of compounds 10 hours and 4 hours (t=−10, −4 hours) on both days 12 and 13 prior to chemotherapy administration. Pups were separated from mom during the topical application dosing period to prevent grooming and removal of compound. Cytotoxic-treated rats experienced whole body alopecia by 21 days of age. Inhibitor efficacy data was analyzed by comparing the % of drug-treated responders and the % of vehicle-treated responders. The amount of hair present on rat scalp at day 21 were scored and averaged for each inhibitor treated rat and ranked as +, ++ and +++.

| Example # | Rank |
|---|---|
| 7 | +++ |
| 9 | ++ |
| 14 | + |
| 23 | +++ |
| 26 | +++ |
| 57 | + |

Wherein:
+ is slight hair coverage
++ is moderate hair coverage
+++ is complete hair coverage Wherein:
+ is slight hair coverage
++ is moderate hair coverage
+++ is complete hair coverage

We claim:
1. A compound of Formula (I):

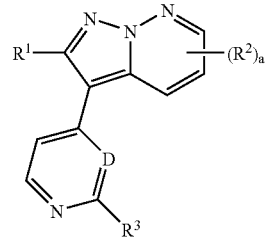

or a salt thereof:
wherein:
D is N or CH
$R^1$ is hydrogen, $C_1$-$C_6$ alkyl, $C_2$-$C_4$ alkenyl, $C_2$-$C_4$ alkynyl, $C_1$-$C_3$ alkoxy, halogen, —$CF_3$, hydroxy, cyano, —S(O)$_y$C$_1$-C$_3$ alkyl, or —NR$^4$R$^5$;
y is 0, 1, or 2;
a is 1 or 2;
$R^2$ is hydrogen, $C_1$-$C_6$ alkyl, $C_2$-$C_6$ alkenyl, $C_2$-$C_6$ alkynyl, $C_1$-$C_6$ haloalkyl, $C_3$-$C_7$ cycloalkyl, halogen, heterocyclyl, aryl, heteroaryl, cyano, azido, nitro, —OR$^8$, —OR$^6$R$^8$, —R$^6$R$^7$, —R$^6$R", —OS(O)$_2$R$^9$, —S(O)$_y$R$^{10}$, —C(O)R$^7$, —C(O)OR$^7$, —C(O)NR$^4$R$^5$, —N(H)R'C(=NR$^4$)NR$^4$R$^5$, —OC(O)NR$^4$R$^5$, —OC(O)OR$^7$, —C(=NR$^4$)NR$^4$R$^5$, —NR$^4$R$^5$, OC(O)R$^7$, or —N(R$^8$)C(O)R$^8$;
$R^3$ is -(Q)$_p$-(Q$^1$)
where
Q is O, N(R$^8$) or S(O)$_y$, p is 0 or 1, y is 0, 1, or 2 and
Q$^1$ is $C_1$-$C_6$ alkyl, $C_3$-$C_7$ cycloalkyl, $C_1$-$C_6$ haloalkyl, aryl, aryl substituted with —C(O)N(H)R$^6$NR$^4$R$^5$ or —OC(H)(OH)R$^6$NR$^4$R$^5$, heteroaryl, aralkyl, or —R$^6$NR$^4$R$^5$;
$R^4$ and $R^5$ are independently hydrogen, $C_1$-$C_3$ alkyl, $C_3$-$C_7$ cycloalkyl, —C(O)R$^9$, or $R^4$ and
$R^5$, together with the nitrogen atom to which they are bound, form a heterocyclyl;
$R^6$ is alkylene, arylene, heteroarylene, $C_3$-$C_7$ cycloalkylene, alkenylene, $C_3$-$C_7$ cycloalkenylene, or alkynylene;
$R^7$ is hydrogen, $C_1$-$C_6$ alkyl, $C_2$-$C_6$ alkenyl, $C_2$-$C_6$ alkynyl, —NR$^4$R$^5$, aryl, aralkyl, heteroaryl, cycloalkyl, heterocyclyl, —S(O)$_y$R$^{10}$, —C(O)R$^8$, —C(O)OR$^8$, —C(O)NR$^4$R$^5$, —S(O)$_2$NR$^4$R$^5$, —N(H)R'C(=NR$^4$)NR$^4$R$^5$, —OC(O)NR$^4$R$^5$, —OC(O)OR$^8$, —C(=NR$^4$)NR$^4$R$^5$, —NR$^4$R$^5$, or —N(R$^8$)C(O)R$^8$;
$R^8$ is hydrogen, $C_1$-$C_6$ alkyl, $C_2$-$C_6$ alkenyl, $C_2$-$C_6$ alkynyl, —NR$^4$R$^5$, aryl, aralkyl, heteroaryl, cycloalkyl, heterocyclyl, or —S(O)$_2$R$^9$;
$R^9$ is $C_1$-$C_6$ alkyl or $C_1$-$C_6$ haloalkyl;
$R^{10}$ is hydrogen, $C_1$-$C_6$ alkyl, $C_2$-$C_6$ alkenyl, $C_2$-$C_6$ alkynyl, —NR$^4$R$^5$, aryl, aralkyl, heteroaryl, cycloalkyl, heterocyclyl, —C(O)R$^8$, —C(O)OR$^8$, —C(O)NR$^4$R$^5$, —N(H)R'C(=NR$^4$)NR$^4$R$^5$, —OC(O)NR$^4$R$^5$, —OC(O)OR$^8$, —C(=NR$^4$)NR$^4$R$^5$, —NR$^4$R$^5$, or —N(R$^8$)C(O)R$^8$;
R' is $C_1$-$C_3$ alkylene; and
R" is —OR$^7$, —OC(O)NR$^4$R$^5$, —OC(O)OR$^7$, or —OC(O)R$^7$.

2. A compound of Formula (II):

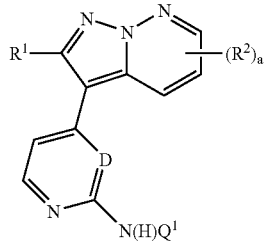

(II)

or a salt thereof:

wherein:

D is N or CH;

$R^1$ is hydrogen, $C_1$-$C_6$ alkyl, $C_2$-$C_4$ alkenyl, $C_2$-$C_4$ alkynyl, $C_1$-$C_3$ alkoxy, —$CF_3$, halogen, hydroxy, cyano, —$S(O)_y C_1$-$C_3$ alkyl, or —$NR^4R^5$;

y is 0, 1, or 2;

a is 1 or 2;

$R^2$ is hydrogen, $C_1$-$C_6$ alkyl, $C_2$-$C_6$ alkenyl, $C_2$-$C_6$ alkynyl, $C_1$-$C_6$ haloalkyl, $C_3$-$C_7$ cycloalkyl, halogen, heterocyclyl, aryl, heteroaryl, cyano, azido, nitro, —$OR^8$, —$OR^6R^8$, —$R^6R^7$, —$R^6R''$, —$OS(O)_2R^9$, —$S(O)_y R^{10}$, —$C(O)R^7$—$C(O)OR^7$, —$C(O)NR^4R^5$, —$N(H)R'C(=NR^4)NR^4R^5$, —$OC(O)NR^4R^5$, —$OC(O)OR^7$, —$C(=NR^4)NR^4R^5$—$NR^4R^5$, —$OC(O)R^7$, or —$N(R^8)C(O)R^8$;

$Q^1$ is $C_1$-$C_6$ alkyl, $C_3$-$C_7$ cycloalkyl, $C_1$-$C_6$ haloalkyl, aryl, aryl substituted with —$C(O)N(H)R^6NR^4R^5$ or —$OC(H)(OH)R^6NR^4R^5$, heteroaryl, aralkyl, or —$R^6NR^4R^5$;

$R^4$ and $R^5$ are independently hydrogen, $C_1$-$C_3$ alkyl, $C_3$-$C_7$ cycloalkyl, —$C(O)R^9$, or $R^4$ and $R^5$, together with the nitrogen atom to which they are bound, form a heterocyclyl;

$R^6$ is alkylene, arylene, heteroarylene, $C_3$-$C_7$ cycloalkylene, alkenylene, $C_3$-$C_7$ cycloalkenylene, or alkynylene;

$R^7$ is hydrogen, $C_1$-$C_6$ alkyl, $C_2$-$C_6$ alkenyl, $C_2$-$C_6$ alkynyl, —$NR^4R^5$, aryl, aralkyl, heteroaryl, cycloalkyl, heterocyclyl, —$S(O)_y R^{10}$, —$C(O)R^8$, —$C(O)OR^8$, —$C(O)NR^4R^5$, —$S(O)_2NR^4R^5$, —$N(H)R'C(=NR^4)NR^4R^5$, —$OC(O)NR^4R^5$, —$OC(O)OR^8$, —$C(=NR^4)NR^4R^5$, —$NR^4R^5$, or —$N(R^8)C(O)R^8$;

$R^8$ is hydrogen, $C_1$-$C_6$ alkyl, $C_2$-$C_6$ alkenyl, $C_2$-$C_6$ alkynyl, —$NR^4R^5$, aryl, aralkyl, heteroaryl, cycloalkyl, heterocyclyl, or —$S(O)_2R^9$;

$R^9$ is $C_1$-$C_6$ alkyl or $C_1$-$C_6$ haloalkyl;

$R^{10}$ is hydrogen, $C_1$-$C_6$ alkyl, $C_2$-$C_6$ alkenyl, $C_2$-$C_6$ alkynyl, —$NR^4R^5$, aryl, aralkyl, heteroaryl, cycloalkyl, heterocyclyl, —$C(O)R^8$, —$C(O)OR^8$, —$C(O)NR^4R^5$, —$N(H)R'C(=NR^4)NR^4R^5$, —$OC(O)NR^4R^5$, —$OC(O)OR^8$, —$C(=NR^4)NR^4R^5$, —$NR^4R^5$, or —$N(R^8)C(O)R^8$;

R' is $C_1$-$C_3$ alkylene; and

R" is —$OR^7$, —$OC(O)NR^4R^5$, —$OC(O)OR^7$, or —$OC(O)R^7$.

3. A compound of Formula (III):

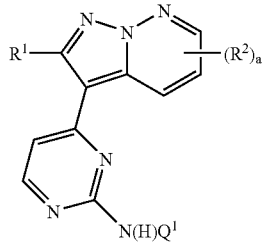

(III)

or a salt thereof:

wherein:

$R^1$ is hydrogen, $C_1$-$C_6$ alkyl, $C_2$-$C_4$ alkenyl, $C_2$-$C_4$ alkynyl, $C_1$-$C_3$ alkoxy, —$CF_3$, halogen, hydroxy, cyano, —$S(O)_y C_1$-$C_3$ alkyl, or —$NR^4R^5$;

y is 0, 1, or 2;

a is 1 or 2;

$R^2$ is hydrogen, $C_1$-$C_6$ alkyl, $C_2$-$C_6$ alkenyl, $C_2$-$C_6$ alkynyl, $C_1$-$C_6$ haloalkyl, —$CF_3$, $C_3$-$C_7$ cycloalkyl, halogen, heterocyclyl, aryl, heteroaryl, cyano, azido, nitro, —$OR^8$, —$OR^6R^8$, —$R^6R^7$, —$R^6R''$, —$OS(O)_2R^9$, —$S(O)_y R^{10}$, —$C(O)R^7$, —$C(O)OR^7$, —$C(O)NR^4R^5$, —$N(H)R'C(=NR^4)NR^4R^5$, —$OC(O)NR^4R^5$, —$OC(O)OR^7$, —$C(=NR^4)NR^4R^5$, —$NR^4R^5$, —$OC(O)R^7$, or —$N(R^8)C(O)R^8$;

$Q^1$ is $C_1$-$C_6$ alkyl, $C_3$-$C_7$ cycloalkyl, $C_1$-$C_6$ haloalkyl, aryl, aryl substituted with —$C(O)N(H)R^6NR^4R^5$ or —$OC(H)(OH)R^6NR^4R^5$, heteroaryl, aralkyl, or —$R^6NR^4R^5$;

$R^4$ and $R^5$ are independently hydrogen, $C_1$-$C_3$ alkyl, $C_3$-$C_7$ cycloalkyl, —$C(O)R^9$, or $R^4$ and $R^5$, together with the nitrogen atom to which they are bound, form a heterocyclyl;

$R^6$ is alkylene, arylene, heteroarylene, $C_3$-$C_7$ cycloalkylene, alkenylene, $C_3$-$C_7$ cycloalkenylene, or alkynylene;

$R^7$ is hydrogen, $C_1$-$C_6$ alkyl, $C_2$-$C_6$ alkenyl, $C_2$-$C_6$ alkynyl, —$NR^4R^5$, aryl, aralkyl, heteroaryl, cycloalkyl, heterocyclyl, —$S(O)_y R^{10}$, —$C(O)R^8$, —$C(O)OR^8$, —$C(O)NR^4R^5$, —$S(O)_2NR^4R^5$, —$N(H)R'C(=NR^4)NR^4R^5$, —$OC(O)NR^4R^5$, —$OC(O)OR^8$, —$C(=NR^4)NR^4R^5$, —$NR^4R^5$, or —$N(R^8)C(O)R^8$;

$R^8$ is hydrogen, $C_1$-$C_6$ alkyl, $C_2$-$C_6$ alkenyl, $C_2$-$C_6$ alkynyl, —$NR^4R^5$, aryl, aralkyl, heteroaryl, cycloalkyl, heterocyclyl, or —$S(O)_2R^9$;

$R^9$ is $C_1$-$C_6$ alkyl or $C_1$-$C_6$ haloalkyl;

$R^{10}$ is hydrogen, $C_1$-$C_6$ alkyl, $C_2$-$C_6$ alkenyl, $C_2$-$C_6$ alkynyl, —$NR^4R^5$, aryl, aralkyl, heteroaryl, cycloalkyl, heterocyclyl, —$C(O)R^8$, —$C(O)OR^8$, —$C(O)NR^4R^5$, —$N(H)R'C(=NR^4)NR^4R^5$, —$OC(O)NR^4R^5$, —$OC(O)OR^8$, —$C(=NR^4)NR^4R^5$, —$NR^4R^5$, or —$N(R^8)C(O)R^8$;

R' is $C_1$-$C_3$ alkylene; and

R" is —$OR^7$—$OC(O)NR^4R^5$, —$OC(O)OR^7$, or —$OC(O)R^7$.

4. A compound of Formula (IV):

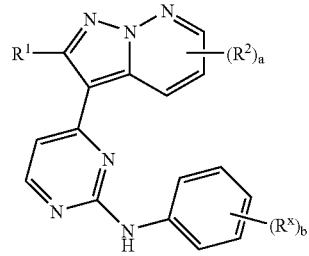

(IV)

or a salt thereof:
wherein:
R$^1$ is hydrogen, C$_1$-C$_6$ alkyl, C$_2$-C$_4$ alkenyl, C$_2$-C$_4$ alkynyl, C$_1$-C$_3$ alkoxy, C$_1$-C$_6$ haloalkyl, halogen, hydroxy, cyano, —S(O)$_y$C$_1$-C$_3$ alkyl, or —NR$^4$R$^5$;

y is 0, 1, or 2;

a is 1 or 2;

R$^2$ is hydrogen, C$_1$-C$_6$ alkyl, C$_2$-C$_6$ alkenyl, C$_2$-C$_6$ alkynyl, C$_1$-C$_6$ haloalkyl, C$_3$-C$_7$ cycloalkyl, halogen, heterocyclyl, aryl, heteroaryl, cyano, azido, nitro, —OR$^8$, —OR$^6$R$^8$, —R$^6$R$^7$, —R$^6$R", —OS(O)$_2$R$^9$, —S(O)$_y$R$^{10}$, —C(O)R$^7$, —C(O)OR$^7$—C(O)NR$^4$R$^5$, —N(H)R'C(=NR$^4$)NR$^4$R$^5$, —OC(O)NR$^4$R$^5$, —OC(O)OR$^7$, —C(=NR$^4$)NR$^4$R$^5$, —NR$^4$R$^5$, —OC(O)R$^7$, or —N(R$^8$)C(O)R$^8$;

b is 1, 2, or 3;

R$^x$ is independently selected from hydrogen, halogen, C$_1$-C$_6$ alkyl, C$_1$-C$_6$ hydroxyalkyl, —CN, —C(O)OH, —OC(O)R$^{11}$, C$_1$-C$_6$ haloalkyl, —NO$_2$, —OH, —OR$^9$, aryl, heteroaryl, heterocyclyl, —NR$^4$R$^5$, —R$^6$NR$^4$R$^5$, —C(O)N(H)R$^6$NR$^4$R$^5$, —S(O)$_y$R$^{10}$, —SO$_2$OH, or b is 2 and the two R$^x$ groups together with the phenyl group to which they are bound form a fused group selected from:

wherein R$_y$ and R$_z$ are independently selected from hydrogen and halogen, wherein R is selected from —CF3, halogen, or hydrogen;

R$^4$ and R$^5$ are independently hydrogen, C$_1$-C$_3$ alkyl, C$_3$-C$_7$ cycloalkyl, —C(O)R$^9$, or R$^4$ and R$^5$, together with the nitrogen atom to which they are bound, form a heterocyclyl;

R$^6$ is alkylene, arylene, heteroarylene, C$_3$-C$_7$ cycloalkylene, alkenylene, C$_3$-C$_7$ cycloalkenylene, or alkynylene;

R$^7$ is hydrogen, C$_1$-C$_6$ alkyl, C$_2$-C$_6$ alkenyl, C$_2$-C$_6$ alkynyl, —NR$^4$R$^5$, aryl, aralkyl, heteroaryl, cycloalkyl, heterocyclyl, —S(O)$_y$R$^{10}$, —C(O)R$^8$, —C(O)OR$^8$, —C(O)NR$^4$R$^5$, —S(O)$_2$NR$^4$R$^5$, —N(H)R'C(=NR$^4$)NR$^4$R$^5$, —OC(O)NR$^4$R$^5$, —OC(O)OR$^8$, —C(=NR$^4$)NR$^4$R$^5$, —NR$^4$R$^5$, or —N(R$^8$)C(O)R$^8$;

R$^8$ is hydrogen, C$_1$-C$_6$ alkyl, C$_2$-C$_6$ alkenyl, C$_2$-C$_6$ alkynyl, —NR$^4$R$^5$, aryl, aralkyl, heteroaryl, cycloalkyl, heterocyclyl, or —S(O)$_2$R$^9$;

R$^9$ is C$_1$-C$_6$ alkyl or C$_1$-C$_6$ haloalkyl;

R$^{10}$ is hydrogen, C$_1$-C$_6$ alkyl, C$_2$-C$_6$ alkenyl, C$_2$-C$_6$ alkynyl, —NR$^4$R$^5$, aryl, aralkyl, heteroaryl, cycloalkyl, heterocyclyl, —C(O)R$^8$, —C(O)OR$^8$, —C(O)NR$^4$R$^5$, —N(H)R'C(=NR$^4$)NR$^4$R$^5$, —OC(O)NR$^4$R$^5$, —OC(O)OR$^8$, —C(=NR$^4$)NR$^4$R$^5$, —NR$^4$R$^5$, or —N(R$^8$)C(O)R$^8$;

R$^{11}$ is C$_1$-C$_6$ alkyl;

R' is C$_1$-C$_3$ alkylene; and

R" is —OR$^7$, —OC(O)NR$^4$R$^5$, —OC(O)OR$^7$, or —OC(O)R$^7$.

5. A compound of Formula (IVa):

(IVa)

or a salt thereof:

b is 1, 2, or 3;

y is 0, 1, or 2;

R$^x$ is independently selected from hydrogen, halogen, C$_1$-C$_6$ alkyl, C$_1$-C$_6$ hydroxyalkyl, —CN, —C(O)OH, —OC(O)R$^{11}$, C$_1$-C$_6$ haloalkyl, —NO$_2$, —OH, —OR$^9$, aryl, heteroaryl, heterocyclyl, —NR$^4$R$^5$, —R$^6$NR$^4$R$^5$, —C(O)N(H)R$^6$NR$^4$R$^5$, —S(O)$_y$R$^{10}$, —SO$_2$OH, or b is 2 and the two R$^x$ groups together with the phenyl group to which they are bound form a fused group selected from:

wherein R$_y$ and Rz are independently selected from hydrogen and halogen,

-continued wherein R is selected from —CF3, halogen, or hydrogen;
$R^4$ and $R^5$ are independently hydrogen, $C_1$-$C_3$ alkyl, $C_3$-$C_7$ cycloalkyl, —C(O)$R^9$, or $R^4$ and
$R^5$, together with the nitrogen atom to which they are bound, form a heterocyclyl;
$R^6$ is alkylene, arylene, heteroarylene, $C_3$-$C_7$ cycloalkylene, alkenylene, $C_3$-$C_7$ cycloalkenylene, or alkynylene;
$R^9$ is $C_1$-$C_6$ alkyl or $C_1$-$C_6$ haloalkyl;
$R^{10}$ is $NH_2$, $C_1$-$C_6$ alkyl, $C_1$-$C_6$ hydroxyalkyl, aryl, heteroaryl, or heterocyclyl; and
$R^{11}$ is $C_1$-$C_6$ alkyl.

6. A compound of Formula (IVa):

(IVa)

or a salt thereof:
b is 1, 2, or 3;
y is 0, 1, or 2;
$R^x$ is independently selected from hydrogen, halogen, $C_1$-$C_6$ alkyl, $C_1$-$C_6$ hydroxyalkyl, —CN, —C(O)OH, —OC(O)$R^{11}$, $C_1$-$C_6$ haloalkyl, —$NO_2$, —OH, —$OR^9$, aryl, heteroaryl, heterocyclyl, —$NR^4R^5$, —$R^6NR^4R^5$, —C(O)N(H)$R^6NR^4R^5$, —S(O)$_y R^{10}$, —$SO_2$OH;
$R^4$ and $R^5$ are independently hydrogen, $C_1$-$C_3$ alkyl, $C_3$-$C_7$ cycloalkyl, —C(O)$R^9$, or $R^4$ and
$R^5$, together with the nitrogen atom to which they are bound, form a heterocyclyl;
$R^6$ is alkylene, arylene, heteroarylene, $C_3$-$C_7$ cycloalkylene, alkenylene, $C_3$-$C_7$ cycloalkenylene, or alkynylene;
$R^9$ is $C_1$-$C_6$ alkyl or $C_1$-$C_6$ haloalkyl;
$R^{10}$ is $NH_2$, $C_1$-$C_6$ alkyl, $C_1$-$C_6$ hydroxyalkyl, aryl, heteroaryl, or heterocyclyl; and
$R^{11}$ is $C_1$-$C_6$ alkyl.

7. A compound as claimed in claim 1, wherein D is N.
8. A compound as claimed in claims 1, wherein $R^1$ is hydrogen or $C_1$-$C_6$ alkyl.
9. A compound as claimed in claim 1, wherein $R^1$ is hydrogen.
10. A compound as claimed in claim 1, wherein $R^1$ is $C_1$-$C_6$ alkyl.
11. A compound as claimed in claim 1, wherein $R^2$ is hydrogen, $C_1$-$C_6$ alkenyl, heterocyclyl, aryl, heteroaryl, —$OR^8$, S(O)$_y R^7$, and —$NR^4R^5$.
12. A compound as claimed in claim 1, wherein $R^2$ is hydrogen, heterocyclyl, aryl, heteroaryl, or —$OR^8$.

13. A compound as claimed in claim 1, wherein $R^2$ is hydrogen.
14. A compound as claimed in claim 1, wherein $R^2$ is —$OR^8$ where $R^8$ is hydrogen, methyl and isopropyl.
15. A compound as claimed in claim 1, wherein $R^2$ is heterocyclyl, aryl, or heteroaryl.
16. A compound as claimed in claim 1, wherein Q is $N(R^8)$, p is 1, and $Q^1$ is $C_1$-$C_6$ alkyl, $C_3$-$C_7$ cycloalkyl, $C_1$-$C_6$ haloalkyl, or aryl.
17. A compound as claimed in claim 1, wherein Q is $N(R^8)$, p is 1, and $Q^1$ is $C_3$-$C_7$ cycloalkyl.
18. A compound as claimed in claim 1, wherein Q is $N(R^8)$, p is 1, and $Q^1$ is cyclopropyl.
19. A compound as claimed in claim 1, wherein Q is $N(R^8)$, p is 1, and $Q^1$ is aryl.
20. A compound as claimed in claim 1, wherein Q is $N(R^8)$, p is 1, and $Q^1$ is phenyl or phenyl substituted with at least one of $C_1$-$C_6$ alkyl, halo, cyano, carboxy, $C_1$-$C_6$ haloalkyl, $C_1$-$C_6$ alkoxy, nitro, heteroaryl, or heterocyclyl.
21. A compound as claimed in claim 4, wherein b is 1, 2, or 3 and $R^x$ is hydrogen, halogen, $C_1$-$C_6$ alkyl, $C_1$-$C_6$ hydroxyalkyl, —CN, —C(O)OH, —OC(O)$R^{11}$, $C_1$-$C_6$ haloalkyl, —$NO_2$, —OH, —$OR^9$, aryl, heteroaryl, heterocyclyl, —$NR^4R^5$, —$R^6NR^4R^5$, —C(O)N(H)$R^6NR^4R^5$, —S(O)$_y R^{10}$, or —$SO_3$H.
22. A compound as claimed in claim 4, wherein; b is 1 or 2 and $R^x$ is halogen, $C_1$-$C_6$ alkyl, $C_1$-$C_6$ hydroxyalkyl, —CN, $C_1$-$C_6$ haloalkyl, —$NO_2$, heterocyclyl, or —$NR^4R^5$.
23. A compound as claimed in claim 4, wherein b is 1 and $R^x$ is —$CH_3$, —$CH_2CH_3$, —$CF_3$, —CN, or —$NO_2$.
24. A compound as claimed in claim 4, wherein b is 2 and the two $R^x$ groups together with the phenyl group to which they are bound form a fused group selected from:

wherein Ry and Rz are independently selected from hydrogen and halogen, wherein R is selected from —CF3, halogen, or hydrogen.
25. A compound as claimed in claim 6, wherein b is 1, 2, or 3; y is 0, 1, or 2; and $R^x$ is independently selected from hydrogen, halogen, $C_1$-$C_6$ alkyl, $C_1$-$C_6$ hydroxyalkyl, —CN, —C(O)OH, —OC(O)R$^{11}$, C$_1$-C$_6$ haloalkyl, —NO$_2$, —OH, —OR$^9$, aryl, heteroaryl, heterocyclyl, —NR$^4$R$^5$, —R$^6$NR$^4$R$^5$, —C(O)N(H)R$^6$NR$^4$R$^5$, —S(O)$_j$R$^{10}$, or —SO$_3$H.

26. A compound as claimed in claim 6, wherein b is 1 or 2 and R$^x$ is independently selected from hydrogen, halogen, C$_1$-C$_6$ alkyl, —CN, —C(O)OH, —C$_1$-C$_6$ haloalkyl, —NO$_2$, —OH, or —OR$^9$.

27. A compound as claimed in claim 6, wherein b is 1 or 2 and R$^x$ is independently selected from hydrogen, halogen, —CN, —C$_1$-C$_6$ haloalkyl, or —NO$_2$.

28. A compound as claimed in claim 6, wherein b is 1 and R$^x$ is selected from —F, —CH$_3$, —CN, —CF$_3$, or —NO$_2$.

29. A compound as claimed in claim 1, selected from the group consisting of:

N-cyclopropyl-4-pyrazolo[1,5-b]pyridazin-3-yl-2-pyrimidinamine;
N-cyclopropyl-N-methyl-4-pyrazolo[1,5-b]pyridazin-3-yl-2-pyrimidinamine;
4-pyrazolo[1,5-b]pyridazin-3-yl-N-(2,2,2-trifluoroethyl)-2-pyrimidinamine;
N-phenyl-4-pyrazolo[1,5-b]pyridazin-3-yl-2-pyrimidinamine;
N-(4-chlorophenyl)-4-pyrazolo[1,5-b]pyridazin-3-yl-2-pyrimidinamine;
N-(4-fluorophenyl)-4-pyrazolo[1,5-b]pyridazin-3-yl-2-pyrimidinamine;
3-[(4-pyrazolo[1,5-b]pyridazin-3-yl-2-pyrimidinyl)amino]benzonitrile;
4-[(4-pyrazolo[1,5-b]pyridazin-3-yl-2-pyrimidinyl)amino]benzoic acid;
4-pyrazolo[1,5-b]pyridazin-3-yl-N-[3-(trifluoromethyl)phenyl]-2-pyrimidinamine;
N-(3-nitrophenyl)-4-pyrazolo[1,5-b]pyridazin-3-yl-2-pyrimidinamine;
N-(2-chlorophenyl)-4-pyrazolo[1,5-b]pyridazin-3-yl-2-pyrimidinamine;
N-(4-methoxyphenyl)-4-pyrazolo[1,5-b]pyridazin-3-yl-2-pyrimidinamine;
4-pyrazolo[1,5-b]pyridazin-3-yl-N-(3,4,5-trimethoxyphenyl)-2-pyrimidinamine;
N-[3-(1,3-oxazol-5-yl)phenyl]-4-pyrazolo[1,5-b]pyridazin-3-yl-2-pyrimidinamine;
N-(4-pyrazolo[1,5-b]pyridazin-3-yl-2-pyrimidinyl)-1H-benzimidazol-6-amine;
N-(4-pyrazolo[1,5-b]pyridazin-3-yl-2-pyrimidinyl)-1,3-benzoxazol-2-amine;
N-(6-chloro-1H-benzimidazol-2-yl)-N-(4-pyrazolo[1,5-b]pyridazin-3-yl-2-pyrimidinyl)amine;
N-(4-chlorobenzyl)-4-pyrazolo[1,5-b]pyridazin-3-yl-2-pyrimidinamine;
N$^1$,N$^1$-dimethyl-N$^3$-(4-pyrazolo[1,5-b]pyridazin-3-yl-2-pyrimidinyl)-1,3-propanediamine methanesulfonate;
N-[3-(4-morpholinyl)propyl]-4-pyrazolo[1,5-b]pyridazin-3-yl-2-pyrimidinamine;
N-[3-(4-methyl-1-piperazinyl)propyl]-4-pyrazolo[1,5-b]pyridazin-3-yl-2-pyrimidinamine;
1-{3-[(4-pyrazolo[1,5-b]pyridazin-3-yl-2-pyrimidinyl)amino]propyl}-2-pyrrolidinone;
N-[3-chloro-4-(4-methyl-1-piperazinyl)phenyl]-4-pyrazolo[1,5-b]pyridazin-3-yl-2-pyrimidinamine;
N-[4-(4-methyl-1-piperazinyl)phenyl]-4-pyrazolo[1,5-b]pyridazin-3-yl-2-pyrimidinamine;
N-[3-methyl-4-(4-methyl-1-piperazinyl)phenyl]-4-pyrazolo[1,5-b]pyridazin-3-yl-2-pyrimidinamine;
N-[4-(4-methyl-1-piperazinyl)-3-(trifluoromethyl)phenyl]-4-pyrazolo[1,5-b]pyridazin-3-yl-2-pyrimidinamine;
N-[3-chloro-4-(4-morpholinyl)phenyl]-4-pyrazolo[1,5-b]pyridazin-3-yl-2-pyrimidinamine;
N-{4-[(diethylamino)methyl]phenyl}-4-pyrazolo[1,5-b]pyridazin-3-yl-2-pyrimidinamine;
N-[2-(diethylamino)ethyl]-4-[(4-pyrazolo[1,5-b]pyridazin-3-yl-2-pyrimidinyl)amino]benzamide;
N-cyclopropyl-4-(2-methylpyrazolo[1,5-b]pyridazin-3-yl)-2-pyrimidinamine;
N-cyclopropyl-4-(2-ethylpyrazolo[1,5-b]pyridazin-3-yl)-2-pyrimidinamine;
4-(2-butylpyrazolo[1,5-b]pyridazin-3-yl)-N-cyclopropyl-2-pyrimidinamine;
N-[4-(4-methyl-1-piperazinyl)phenyl]-4-(2-methylpyrazolo[1,5-b]pyridazin-3-yl)-2-pyrimidinamine;
4-(2-ethylpyrazolo[1,5-b]pyridazin-3-yl)-N-[4-(4-methyl-1-piperazinyl)phenyl]-2-pyrimidinamine;
4-(2-butylpyrazolo[1,5-b]pyridazin-3-yl)-N-[4-(4-methyl-1-piperazinyl)phenyl]-2-pyrimidinamine;
N-cyclopropyl-4-(6-methoxypyrazolo[1,5-b]pyridazin-3-yl)-2-pyrimidinamine;
4-(6-methoxypyrazolo[1,5-b]pyridazin-3-yl)-N-[4-(4-methyl-1-piperazinyl)phenyl]-2-pyrimidinamine;
3-[2-(cyclopropylamino)-4-pyrimidinyl]pyrazolo[1,5-b]pyridazin-6-ol;
N-cyclopropyl-4-(6-isopropoxypyrazolo[1,5-b]pyridazin-3-yl)-2-pyrimidinamine;
N-[4-(6-isopropoxypyrazolo[1,5-b]pyridazin-3-yl)-2-pyrimidinyl]-N-[4-(4-methyl-1-piperazinyl)phenyl]amine;
3-[2-(cyclopropylamino)-4-pyrimidinyl]pyrazolo[1,5-b]pyridazin-6-yl trifluoromethanesulfonate;
4-[6-(2-chlorophenyl)pyrazolo[1,5-b]pyridazin-3-yl]-N-cyclopropyl-2-pyrimidinamine;
N-cyclopropyl-4-[6-(2-thienyl)pyrazolo[1,5-b]pyridazin-3-yl]-2-pyrimidinamine;
N-cyclopropyl-4-[6-(4-fluorophenyl)pyrazolo[1,5-b]pyridazin-3-yl]-2-pyrimidinamine;
N-cyclopropyl-4-(6-vinylpyrazolo[1,5-b]pyridazin-3-yl)-2-pyrimidinamine;
N-cyclopropyl-4-[6-(4-morpholinyl)pyrazolo[1,5-b]pyridazin-3-yl]-2-pyrimidinamine;
N-cyclopentyl-3-[2-(cyclopropylamino)-4-pyrimidinyl]pyrazolo[1,5-b]pyridazin-6-amine;
N-cyclopropyl-4-[6-(1-pyrrolidinyl)pyrazolo[1,5-b]pyridazin-3-yl]-2-pyrimidinamine;
N-cyclopropyl-4-[6-(2-fluoro-4-pyridinyl)pyrazolo[1,5-b]pyridazin-3-yl]-2-pyrimidinamine;
N-cyclopropyl-4-[6-(phenylsulfanyl)pyrazolo[1,5-b]pyridazin-3-yl]-2-pyrimidinamine;
4-[6-(4-fluorophenyl)pyrazolo[1,5-b]pyridazin-3-yl]-N-(4-methoxyphenyl)-2-pyrimidinamine;
4-[6-(4-fluorophenyl)pyrazolo[1,5-b]pyridazin-3-yl]-N-[4-(4-methyl-1-piperazinyl)phenyl]-2-pyrimidinamine;
N$^1$,N$^1$-dimethyl-N$^4$-{4-[6-(4-morpholinyl)pyrazolo[1,5-b]pyridazin-3-yl]-2-pyrimidinyl}-1,4-benzenediamine;
1-(dimethylamino)-3-[4-({4-[6-(4-morpholinyl)pyrazolo[1,5-b]pyridazin-3-yl]-2-pyrimidinyl}amino)phenoxy]-2-propanol;
N-(1,3-benzodioxol-5-yl)-4-pyrazolo[1,5-b]pyridazin-3-yl-2-pyrimidinamine;
N-(2,3-dihydro-1,4-benzodioxin-6-yl)-4-pyrazolo[1,5-b]pyridazin-3-yl-2-pyrimidinamine;
N-[3-methoxy-5-(trifluoromethyl)phenyl]-4-pyrazolo[1,5-b]pyridazin-3-yl-2-pyrimidinamine;

4-[(4-pyrazolo[1,5-b]pyridazin-3-yl-2-pyrimidinyl)amino]benzonitrile;

N-(4-nitrophenyl)-4-pyrazolo[1,5-b]pyridazin-3-yl-2-pyrimidinamine;

N-(3-methoxyphenyl)-4-pyrazolo[1,5-b]pyridazin-3-yl-2-pyrimidinamine;

N-(3,5-dimethylphenyl)-4-pyrazolo[1,5-b]pyridazin-3-yl-2-pyrimidinamine;

N-(4-aminosulfonylphenyl)-4-pyrazolo[1,5-b]pyridazin-3-yl-2-pyrimidinamine; and

N-(4-methylsulfonylphenyl)-4-pyrazolo[1,5-b]pyridazin-3-yl-2-pyrimidinamine; or a salt thereof.

30. A pharmaceutical composition, comprising: a therapeutically effective amount of a compound as claimed in claim 1, or a salt thereof and one or more of pharmaceutically acceptable carriers, diluents and excipients.

31. The pharmaceutical composition of claim 30, further comprising at least one anti-neoplastic agent.

32. A method of treating breast cancer in a mammal, including administering to said mammal a therapeutically effective amount of a compound as claimed in claim 1, or salt thereof.

33. A method of treating breast cancer in a mammal, including administering to said mammal therapeutically effective amounts of (i) a compound as claimed in claim 1, or salt thereof and (ii) at least one additional anti-cancer therapy.

34. A process for preparing a compound of formula (Q)

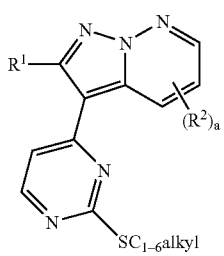
(Q)

comprising, the step of:

(i) reacting in the presence of a base a compound of formula (U)

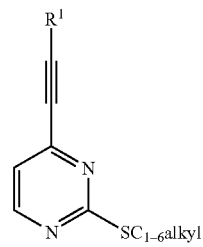
(U)

with a compound of formula (E)

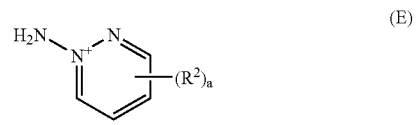
(E)

wherein $R^1$ is hydrogen, $C_1$-$C_6$ alkyl, $C_1$-$C_4$ alkenyl, $C_1$-$C_4$ alkynyl, $C_1$-$C_3$ alkoxy, halogen, hydroxy, cyano, —S(O)$_y$ $C_1$-$C_3$ alkyl, —NR$^4$R$^5$;

a is 1 or 2; and $R^2$ is hydrogen, $C_1$-$C_6$ alkyl, $C_1$-$C_6$ alkenyl, $C_1$-$C_6$ alkynyl, $C_1$-$C_6$ haloalkyl, $C_3$-$C_7$ cycloalkyl, halogen, heterocyclyl, aryl, heteroaryl, cyano, azido, nitro, —OR$^8$, —OR$^6$R$^8$, —R$^6$R$^7$, —R$^6$R", S(O)$_y$R$^7$, —C(O)R$^7$, —C(O)OR$^7$, —C(O)NR$^4$R$^5$, —NR'(C=NR$^4$)NR$^4$R$^5$, —OC(O)NR$^4$R$^5$, —OC(O)OR$^7$, —C(=NR$^4$)NR$^4$R$^5$—NR$^4$R$^5$, —OC(O)R$^7$, —NR$^8$C(O)R$^8$;

$R^4$ and $R^5$ are independently hydrogen, $C_1$-$C_3$ alkyl, $C_3$-$C_7$ cycloalkyl, —C(O)R$^9$, or $R^4$ and $R^5$, together with the nitrogen atom to which they are bound, form a heterocyclyl;

$R^6$ is alkylene, arylene, heteroarylene, $C_3$-$C_7$ cycloalkylene, alkenylene, $C_3$-$C_7$ cycloalkenylene, or alkynylene;

$R^7$ is hydrogen, $C_1$-$C_6$ alkyl, $C_2$-$C_6$ alkenyl, $C_2$-$C_6$ alkynyl, —NR$^4$R$^5$, aryl, aralkyl, heteroaryl, cycloalkyl, heterocyclyl, —S(O)$_y$R$^{10}$, —C(O)R$^8$, —C(O)OR$^8$, —C(O)NR$^4$R$^5$, —S(O)$_2$NR$^4$R$^5$, —N(H)R'C(=NR$^4$)NR$^4$R$^5$, —OC(O)NR$^4$R$^5$, —OC(O)OR$^8$, —C(=NR$^4$)NR$^4$R$^5$, —NR$^4$R$^5$, or —N(R$^8$)C(O)R$^8$;

$R^8$ is hydrogen, $C_1$-$C_6$ alkyl, $C_2$-$C_6$ alkenyl, $C_2$-$C_6$ alkynyl, —NR$^4$R$^5$, aryl, aralkyl, heteroaryl, cycloalkyl, heterocyclyl, or —S(O)$_2$R$^9$;

$R^9$ is $C_1$-$C_6$ alkyl or $C_1$-$C_6$ haloalkyl;

$R^{10}$ is hydrogen, $C_1$-$C_6$ alkyl, $C_2$-$C_6$ alkenyl, $C_2$-$C_6$ alkynyl, —NR$^4$R$^5$, aryl, aralkyl, heteroaryl, cycloalkyl, heterocyclyl, —C(O)R$^8$, —C(O)OR$^8$, —C(O)NR$^4$R$^5$, —N(H)R'C(=NR$^4$)NR$^4$R$^5$, —OC(O)NR$^4$R$^5$, —OC(O)OR$^8$, —C(=NR$^4$)NR$^4$R$^5$, —NR$^4$R$^5$, or —N(R$^8$)C(O)R$^8$;

R' is $C_1$-$C_3$ alkylene; and

R" is —OR$^7$, —OC(O)NR$^4$R$^5$, —OC(O)OR$^7$, or —OC(O)R$^7$.

35. A process as claimed in claim 34, wherein the base is an amine.

36. A process as claimed in claim 34, wherein the base is an alkali metal hydroxide.

* * * * *